(12) United States Patent
Tangy et al.

(10) Patent No.: US 10,227,385 B2
(45) Date of Patent: Mar. 12, 2019

(54) CHIMERIC POLY PEPTIDES AND THE THERAPEUTIC USE THEREOF AGAINST A FLAVIVIRIDAE INFECTION

(71) Applicants: INSTITUT PASTEUR, Paris (FR); CENTRE NATIONAL DE LA RECHERCHE SCIENTIFIQUE, Paris (FR)

(72) Inventors: Frederic Tangy, Les Lilas (FR); Marianne Lucas-Hourani, Paris (FR); Erika Navarro-Sanchez, Montreuil-sous-Bois (FR); Marie-Pascale Frenkiel, Levallois-Perret (FR); Hugues Bedouelle, Paris (FR); Chantal Combredet, Paris (FR); Philippe Despres, La Garenne-Colombes (FR)

(73) Assignees: INSTITUT PASTEUR, Paris (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 15/409,210

(22) Filed: Jan. 18, 2017

(65) Prior Publication Data

US 2017/0121375 A1    May 4, 2017

Related U.S. Application Data

(60) Division of application No. 14/477,223, filed on Sep. 4, 2014, now Pat. No. 9,579,375, which is a continuation of application No. 13/089,705, filed on Apr. 19, 2011, now Pat. No. 8,853,379, which is a continuation of application No. 11/917,907, filed as application No. PCT/FR2006/001396 on Jun. 20, 2006, now Pat. No. 8,337,857.

(30) Foreign Application Priority Data

Jun. 20, 2005   (CA) ..................... 2508266

(51) Int. Cl.

| C07K 14/005 | (2006.01) |
|---|---|
| A61K 39/12 | (2006.01) |
| C12N 15/86 | (2006.01) |
| A61K 39/165 | (2006.01) |
| C12N 7/00 | (2006.01) |
| A61K 39/00 | (2006.01) |
| A61K 38/00 | (2006.01) |

(52) U.S. Cl.
CPC ........... *C07K 14/005* (2013.01); *A61K 39/12* (2013.01); *A61K 39/165* (2013.01); *C12N 7/00* (2013.01); *C12N 15/86* (2013.01); *A61K 38/00* (2013.01); *A61K 2039/5254* (2013.01); *A61K 2039/5256* (2013.01); *A61K 2039/53* (2013.01); *A61K 2039/545* (2013.01); *A61K 2039/55* (2013.01); *A61K 2039/55505* (2013.01); *C07K 2319/00* (2013.01); *C07K 2319/04* (2013.01); *C12N 2760/18434* (2013.01); *C12N 2760/18443* (2013.01); *C12N 2770/24122* (2013.01); *C12N 2770/24134* (2013.01); *C12N 2770/24171* (2013.01); *Y02A 50/386* (2018.01); *Y02A 50/388* (2018.01); *Y02A 50/39* (2018.01); *Y02A 50/394* (2018.01)

(58) Field of Classification Search
None
See application file for complete search history.

(56) References Cited

U.S. PATENT DOCUMENTS

| 8,337,857 B2 | 12/2012 | Tangy |
|---|---|---|
| 2005/0002953 A1 | 1/2005 | Jens |

FOREIGN PATENT DOCUMENTS

| WO | 0196376 A2 | 12/2001 |
|---|---|---|
| WO | 2004016586 A2 | 2/2004 |
| WO | 2004076619 A2 | 9/2004 |
| WO | 2004112694 A2 | 12/2004 |
| WO | 2005111221 A1 | 11/2005 |

OTHER PUBLICATIONS

Zuniga et al., Vaccine, vol. 25, pp. 2783-2794 (2007).
Mok et al., The Open Virology Journal, vol. 6, pp. 12-22 (2012).
Catteau, Adeline et al., "Dengue virus M protein contains a proapoptotic sequence referred to as ApoptoM", Journal of General Virology, vol. 84, pp. 2781-2793, 2003.
Catteau, Adeline et al., "Expression of dengue ApoptoM sequence results in disruption of mitochondrial potential and caspase activation", Biochimie, vol. 85, pp. 789-793, 2003.
Colombage, G. et al., "DNA-Based and alpha virus-Vectored Immunisation with PrM and E Proteins Elicits Long-Lived AT and protective Immunity against the Flavivirus, Murray Valley Encephalitis Virus", Virology, vol. 250, pp. 151-163, 1998.
Fonseca, Benedito A.L. et al., "Recombinant vaccinia viruses co-expression dengue-1 glycoproteins prM and E induce neutralizing antibodies in mice", Vaccine, vol. 12, No. 3, pp. 279-285,1994.

(Continued)

*Primary Examiner* — Stacy B Chen
(74) *Attorney, Agent, or Firm* — Arrigo, Lee, Guttman & Mouta-Bellum LLP

(57) ABSTRACT

The invention relates to building a chimeric polypeptide used for preventing or treating a Flaviviridae infection. The use of the inventive chimeric polypeptide for producing recombinant viral vectors such as a measles living viral vector is also disclosed.

12 Claims, 29 Drawing Sheets

Specification includes a Sequence Listing.

(56) References Cited

OTHER PUBLICATIONS

Crill, Wayne D. et al., "Monoclonal Antibodies That Bind to Domain III of Dengue Virus E Glycoprotein Are the Most AV Efficient Blockers of Virus Adsorption to Vero Cells", Journal of Virology. vol. 75, No. 16, pp. 7769-7773, 2001.

Despres, Philippe et al., "Live Measles Vaccine Expressing the Secreted Form of the West Nile Virus Envelope AW Glycoprotein Protects against West Nile Virus Encephalitis", Journal of Infectious Diseases, vol. 191, No. 2, pp. 207-214, 2005.

Mota, Javier et al., "Induction of protective antibodies against dengue virus by tetravalent DNA immunization of mice with domain III of the envelope protein", Vaccine, vol. 23, p. 3469-3476, 2005.

Wang, Songli et al., "PrM- and Cell-Binding Domains of the Dengue Virus E Protein", Journal of Virology, vol. 73, No. 3, pp. 2547-2551, 1999.

Hermida, Lisset et al., "A recombinant fusion protein containing the domain II I of the dengue-2 envelope protein is immunogenic and protective in o Additional References sheet(s) attached nonhuman primates", Vaccine, vol. 24, pp. 3165-3171, 2006.

Chávez, Juliana Helena, et al., "Domain III peptides from flavivirus envelope protein are useful antigens for serologic diagnosis and targets for immunization," Biologicals, vol. 38, pp. 613-618 (2010).

Tanaka, Mariko, et al., "Homology among Eleven Flavivirus by Comparative Nucleotide Sequence of Geomic RNAs and Deduced Amino Acid Sequences of Viral Proteins," Trop. Med., vol. 33 (1,2), pp. 23-33, Jun. 1991.

FIGURE 1 (SEQ ID NO : 1)
(SEQ ID NO : 2)

```
              M   L   L   S   V   P   L   L   L   G   L   L   G   L   A   V   16
cgt acg      ATG CTG CTA TCC GTG CCG TTG CTG CTC GGC CTC CTC GGC CTG GCC GTC  54

A   R   S   K   G   M   S   Y   V   M   C   T   G   S   F   K   L   E   34
    GCC AGA TCT AAA GGG ATG TCA TAT GTG ATG TGC ACA GGC TCA TTT AAG CTA GAG  108

K   E   V   A   E   T   Q   H   G   T   V   L   V   Q   V   K   Y   E   52
    AAG GAA GTG GCT GAG ACC CAG CAT GGG ACT GTC CTA GTG CAG GTT AAA TAC GAA  162

G   T   D   A   P   C   K   I   P   F   S   T   Q   D   E   K   G   V   70
    GGA ACA GAT GCG CCA TGC AAG ATC CCC TTT TCG ACC CAA GAT GAG AAA GGA GTG  216

T   Q   N   G   R   L   I   T   A   N   P   I   V   T   D   K   E   K   88
    ACC CAG AAT GGG AGA TTG ATA ACA GCC AAT CCC ATA GTT ACT GAC AAA GAA AAA  270

P   V   N   I   E   T   E   P   P   F   G   E   S   Y   I   I   V   G   106
    CCA GTC AAC ATT GAG ACA GAA CCA CCT TTT GGT GAG AGC TAC ATC ATA GTA GGG  324

A   G   E   K   A   L   K   L   S   W   F   K   R   *               119
    GCA GGT GAA AAA GCT TTG AAA CTA AGC TGG TTC AAG CGA tag cgg ccg cta taa  378 gcg cgc                                                                    384
``` ssCRT       aa 1-17
[EDIII]<sub>DV1</sub>   aa 19-121

FIGURE 2 (SEQ ID NO : 3)
(SEQ ID NO: 4)

|  |  | M | L | L | S | V | P | L | L | L | G | L | L | G | L | A | V | 16 |
|---|---|---|---|---|---|---|---|---|---|---|---|---|---|---|---|---|---|---|
| cgt | acg | ATG | CTG | CTA | TCC | GTG | CCG | TTG | CTG | CTC | GGC | CTC | CTC | GGC | CTG | GCC | GTC | 54 |

| A | R | S | K | G | M | S | Y | V | M | C | T | G | S | F | K | L | E | 34 |
|---|---|---|---|---|---|---|---|---|---|---|---|---|---|---|---|---|---|---|
| GCC | AGA | TCT | AAA | GGG | ATG | TCA | TAT | GTG | ATG | TGC | ACA | GGC | TCA | TTT | AAG | CTA | GAG | 108 |

| K | E | V | A | E | T | Q | H | G | T | V | L | V | Q | V | K | Y | E | 52 |
|---|---|---|---|---|---|---|---|---|---|---|---|---|---|---|---|---|---|---|
| AAG | GAA | GTG | GCT | GAG | ACC | CAG | CAT | GGG | ACT | GTC | CTA | GTG | CAG | GTT | AAA | TAC | GAA | 162 |

| G | T | D | A | P | C | K | I | P | F | S | T | Q | D | E | K | G | V | 70 |
|---|---|---|---|---|---|---|---|---|---|---|---|---|---|---|---|---|---|---|
| GGA | ACA | GAT | GCG | CCA | TGC | AAG | ATC | CCC | TTT | TCG | ACC | CAA | GAT | GAG | AAA | GGA | GTG | 216 |

| T | Q | N | G | R | L | I | T | A | N | P | I | V | T | D | K | E | K | 88 |
|---|---|---|---|---|---|---|---|---|---|---|---|---|---|---|---|---|---|---|
| ACC | CAG | AAT | GGG | AGA | TTG | ATA | ACA | GCC | AAT | CCC | ATA | GTT | ACT | GAC | AAA | GAA | AAA | 270 |

| P | V | N | I | E | T | E | P | P | F | G | E | S | Y | I | I | V | G | 106 |
|---|---|---|---|---|---|---|---|---|---|---|---|---|---|---|---|---|---|---|
| CCA | GTC | AAC | ATT | GAG | ACA | GAA | CCA | CCT | TTT | GGT | GAG | AGC | TAC | ATC | ATA | GTA | GGG | 324 |

| A | G | E | K | A | L | K | L | S | W | F | R | R | D | K | R | S | V | 124 |
|---|---|---|---|---|---|---|---|---|---|---|---|---|---|---|---|---|---|---|
| GCA | GGT | GAA | AAA | GCT | TTG | AAA | CTA | AGC | TGG | TTC | CGA | CGA | GAC | AAA | CGT | TCC | GTG | 378 |

| A | L | A | P | H | V | G | L | G | L | E | T | R | T | E | T | W | M | 142 |
|---|---|---|---|---|---|---|---|---|---|---|---|---|---|---|---|---|---|---|
| GCA | CTG | GCC | CCA | CAC | GTG | GGA | CTT | GGT | CTA | GAA | ACA | AGA | ACC | GAA | ACA | TGG | ATG | 432 |

| S | S | E | G | A | W | K | Q | I | Q | K | V | E | T | W | A | L | R | 160 |
|---|---|---|---|---|---|---|---|---|---|---|---|---|---|---|---|---|---|---|
| TCC | TCT | GAA | GGC | GCC | TGG | AAA | CAA | ATA | CAA | AAA | GTG | GAG | ACT | TGG | GCT | TTG | AGA | 486 |

| H | P | * |  |  |  |  |  | 170 |
|---|---|---|---|---|---|---|---|---|
| CAC | CCA | tga | tag | cgg | ccg | cta | taa | gcg cgc | 516 | ssCRT     aa 1-17
[EDIII]$_{DV1}$   aa 19-119
[M$^{1-40}$]$_{DV1}$   aa 125-172

FIGURE 6 (SEQ ID NO : 5)

```
CGTACGATGCTGCTATCCGTGCCGTTGCTGCTCGGCCTCCTCGGCCTGGC
CGTCGCCAGATCTAAAGGGATGTCATATGTGATGTGCACAGGCTCATTTA
AGCTAGAGAAGGAAGTGGCTGAGACCCAGCATGGGACTGTCCTAGTGCAG
GTTAAATACGAAGGAACAGATGCGCCATGCAAGATCCCCTTTTCGACCCA
AGATGAGAAAGGAGTGACCCAGAATGGGAGATTGATAACAGCCAATCCCA
TAGTTACTGACAAAGAAAAACCAGTCAACATTGAGACAGAACCACCTTTT
GGTGAGAGCTACATCATAGTAGGGCAGGTGAAAAAGCTTTGAAACTAAG
CTGGTTCCGACGAGACAAACGTTCCGTGGCACTGGCCCCACACGTGGGAC
TTGGTCTAGAAACAAGAACCGAAACATGGATGTCCTCTGAAGGCGCCTGG
AAACAAATACAAAAAGTGGAGACTTGGGCTTTGAGACACCCATGATAGCG
GCCGCTATAAGCGCGC
```

FIGURE 7 (SEQ ID NO : 6)
(SEQ ID NO : 7)

```
  R   T   M   L   L   S   V   P   L   L   L   G   L   L   G   L   A   V    18
CGT ACG ATG CTG CTA TCC GTG CCG TTG CTC CTC GGC CTC CTC GGC CTG GCC GTC    54

A   R   S   K   G   T   T   Y   G   M   C   T   E   K   F   S   F   A    36
GCC AGA TCT AAA GGC ACA ACC TAT GGC ATG TGC ACA GAA AAA TTC TCG TTC GCG   108

K   N   P   A   D   T   G   H   G   T   V   V   I   E   L   S   Y   S    54
AAA AAT CCG GCG GAC ACT GGT CAC GGA ACA GTT GTC ATT GAA CTT TCC TAC TCT   162

G   S   D   G   P   C   K   I   P   I   V   S   V   A   S   L   N   D    72
GGG AGT GAT GGC CCT TGC AAA ATT CCG ATT GTC TCC GTT GCG AGC CTC AAT GAC   216

M   T   P   V   G   R   L   V   T   V   N   P   F   V   A   T   S   S    90
ATG ACC CCC GTC GGG CGG CTG GTG ACA GTG AAC CCC TTC GTC GCG ACT TCC AGC   270

A   N   S   K   V   L   V   E   M   E   P   P   F   G   D   S   Y   I   108
GCC AAC TCA AAG GTG CTA GTC GAG ATG GAA CCC CCC TTC GGA GAC TCC TAC ATC   324

V   V   G   R   G   D   K   Q   I   N   H   H   W   H   K   K   R   S   126
GTA GTT GGA AGG GGA GAC AAG CAG ATC AAC CAC CAT TGG CAC AAA AAG CGA AGC   378

R   R   S   V   S   V   Q   T   H   G   E   S   S   L   V   N   K   K   144
AGG AGA TCC GTG TCG GTC CAA ACA CAT GGG GAG AGT TCA CTA GTG AAT AAA AAA   432

E   A   W   L   D   S   T   K   A   T   R   Y   L   M   K   T   E   N   162
GAG GCT TGG CTG GAT TCA ACG AAA GCC ACA CGA TAC CTC ATG AAA ACT GAG AAC   486

W   I   V   R   N   P   *   *   R   P   L   *   A   R                   176
TGG ATC GTA AGG AAT CCT TGA TAG CGG CCG CTA TAA GCG CGC                   528
```

FIGURE 8 (SEQ ID NO : 8)
(SEQ ID NO : 9)

```
  R   T   M   L   L   S   V   P   L   L   L   G   L   L   G   L   A   V    18
CGT ACG ATG CTG CTA TCC GTG CCG TTG CTG CTC GGC CTC CTC GGC CTG GCC GTC    54

A   R   S   K   G   M   S   Y   V   M   C   T   G   S   F   K   L   E    36
GCC AGA TCT AAA GGG ATG TCA TAT GTG ATG TGC ACA GGC TCA TTT AAG CTA GAG   108

K   E   V   A   E   T   Q   H   G   T   V   L   V   Q   V   K   Y   E    54
AAG GAA GTG GCT GAG ACC CAG CAT GGG ACT GTC CTA GTG CAG GTT AAA TAC GAA   162

G   T   D   A   P   C   K   I   P   F   S   T   Q   D   E   K   G   V    72
GGA ACA GAT GCG CCA TGC AAG ATC CCC TTT TCG ACC CAA GAT GAG AAA GGA GTG   216

T   Q   N   G   R   L   I   T   A   N   P   I   V   T   D   K   E   K    90
ACC CAG AAT GGG AGA TTG ATA ACA GCC AAT CCC ATA GTT ACT GAC AAA GAA AAA   270

P   V   N   I   E   T   E   P   P   F   G   E   S   Y   I   I   V   G   108
CCA GTC AAC ATT GAG ACA GAA CCA CCT TTT GGT GAG AGC TAC ATC ATA GTA GGG   324

A   G   E   K   A   L   K   L   S   W   F   K   K   G   S   S   I   G   126
GCA GGT GAA AAA GCT TTG AAA CTA AGC TGG TTC AAG AAA GGA AGC AGC ATA GGG   378

K   M   F   E   A   T   G   G   S   G   G   K   G   M   S   Y   S       144
AAA ATG TTC GAA GCA ACC GCC GGA GGA TCA GGA GGG AAA GGA ATG TCA TAC TCT   432

M   C   T   G   K   F   K   I   V   K   E   I   A   E   T   Q   H   G   162
ATG TGT ACA GGA AAG TTT AAA ATT GTG AAG GAA ATA GCA GAA ACA CAA CAT GGA   486

T   I   V   I   R   V   Q   Y   E   G   D   G   S   P   C   K   I   P   180
ACA ATA GTT ATC AGA GTA CAA TAT GAA GGG GAC GGC TCT CCA TGT AAG ATC CCT   540

F   E   I   M   D   L   E   K   R   H   V   L   G   R   L   I   T   V   198
TTT GAG ATA ATG GAT TTG GAA AAA AGA CAC GTC TTA GGT CGC CTG ATT ACA GTT   594

N   P   I   V   T   E   K   D   S   P   V   N   I   E   A   E   P   P   216
AAC CCG ATC GTA ACA GAA AAA GAT AGC CCA GTC AAC ATA GAA GCA GAA CCT CCA   648

F   G   D   S   Y   I   I   I   G   V   E   P   G   Q   L   K   L   N   234
TTC GGA GAC AGC TAC ATC ATC ATA GGA GTA GAG CCG GGA CAA TTG AAA CTC AAC   702

W   F   K   K   G   S   S   I   G   Q   M   F   E   T   T   M   S   G   252
TGG TTT AAG AAA GGA AGT TCC ATC GGC CAA ATG TTT GAG ACA ACA ATG AGC GGC   756

R   V   E   T   W   A   L   R   H   P   *   *   A   R                   266
CGC GTG GAG ACT TGG GCT TTG AGA CAC CCA TAG TAA GCG CGC                   798
```

FIGURE 9 (SEQ ID NO : 10)
(SEQ ID NO : 11)

```
  R   T   M   L   L   S   V   P   L   L   L   G   L   L   G   L   A   V    18
CGT ACG ATG CTG CTA TCC GTG CCG TTG CTC CTC GGC CTC CTC GGC CTG GCC GTC    54

A   R   S   K   G   M   S   Y   A   M   C   L   N   T   F   V   L   K    36
GCC AGA TCT AAG GGG ATG AGC TAT GCA ATG TGC TTG AAT ACC TTT GTG TTG AAG   108

K   E   V   S   E   T   Q   H   G   T   I   L   I   K   V   E   Y   K    54
AAA GAA GTC TCC GAA ACG CAG CAT GGG ACA ATA CTC ATT AAG GTT GAG TAC AAA   162

G   E   D   A   P   C   K   I   P   F   S   T   E   D   G   Q   G   K    72
GGG GAA GAT GCA CCT TGC AAG ATT CCT TTC TCC ACA GAG GAT GGA CAA GGG AAA   216

A   H   N   G   R   L   I   T   A   N   P   V   V   T   K   K   E   E    90
GCT CAC AAT GGT AGA CTG ATC ACA GCC AAC CCA GTG GTG ACC AAG AAG GAG GAG   270

P   V   N   I   E   A   E   P   P   F   G   E   S   N   I   V   I   G   108
CCT GTC AAC ATT GAG GCT GAA CCT CCT TTT GGG GAA AGT AAC ATA GTG ATT GGA   324

I   G   D   K   A   L   K   I   N   W   Y   K   K   G   S   S   I   G   126
ATT GGA GAC AAA GCC TTG AAA ATT AAC TGG TAC AAG AAG GGA AGC TCG ATT GGG   378

K   M   F   E   A   T   A   G   G   S   G   G   K   G   M   S   Y   T   144
AAG ATG TTC GAG GCC ACT GCC GGT GGT TCT GGT GGT AAG GGA ATG TCA TAC ACG   432

M   C   S   G   K   F   S   I   D   K   E   M   A   E   T   Q   H   G   162
ATG TGC TCA GGA AAG TTC TCA ATT GAT AAA GAG ATG GCA GAA ACA CAG CAT GGG   486

T   T   V   V   K   V   K   Y   E   G   A   G   A   P   C   K   V   P   180
ACA ACA GTG GTG AAA GTC AAG TAT GAG GGT GCT GGA GCT CCA TGT AAA GTT CCC   540

I   E   I   R   D   V   N   K   E   K   V   V   G   R   I   I   S   S   198
ATA GAG ATA AGA GAT GTG AAC AAG GAA AAA GTG GTT GGG CGT ATC ATC TCA TCT   594

T   P   F   A   E   N   T   N   S   V   T   N   I   E   L   E   P   P   216
ACC CCT TTT GCT GAG AAT ACC AAC AGT GTG ACC AAT ATA GAA TTG GAA CCC CCT   648

F   G   D   S   Y   I   V   I   G   V   G   D   S   A   L   T   L   H   234
TTT GGG GAT AGC TAC ATA GTA ATA GGT GTA GGA GAC AGT GCA TTA ACA CTC CAT   702

W   F   R   K   G   S   S   I   G   K   M   F   E   S   T   Y   S   G   252
TGG TTC AGG AAA GGG AGC TCC ATT GGC AAG ATG TTT GAG TCC ACA TAC AGC GGC   756

R   V   E   T   W   A   L   R   H   P   *   *   A   R                   266
CGC GTG GAG ACT TGG GCT TTG AGA CAC CCA TAG TAA GCG CGC                   798
```

FIGURE 10 (SEQ ID NO : 12)
(SEQ ID NO : 13)

| | | | | | | | | | | | | | | | | | |
|---|---|---|---|---|---|---|---|---|---|---|---|---|---|---|---|---|---|
| R | T | M | L | L | S | V | P | L | L | G | L | L | G | L | A | V | 18 |
| CGT | ACG | ATG | CTG | CTA | TCC | GTG | CCG | TTG | CTG | CTC | GGC | CTC | CTC | GGC | CTG | GCC | GTC | 54 |
| A | R | S | K | G | M | S | Y | V | M | C | T | G | S | F | K | L | E | 36 |
| GCC | AGA | TCT | AAA | GGG | ATG | TCA | TAT | GTG | ATG | TGC | ACA | GGC | TCA | TTT | AAG | CTA | GAG | 108 |
| K | E | V | A | E | T | Q | H | G | T | V | L | V | Q | V | K | Y | E | 54 |
| AAG | GAA | GTG | GCT | GAG | ACC | CAG | CAT | GGG | ACT | GTC | CTA | GTG | CAG | GTT | AAA | TAC | GAA | 162 |
| G | T | D | A | P | C | K | I | P | F | S | T | Q | D | E | K | G | V | 72 |
| GGA | ACA | GAT | GCG | CCA | TGC | AAG | ATC | CCC | TTT | TCG | ACC | CAA | GAT | GAG | AAA | GGA | GTG | 216 |
| T | Q | N | G | R | L | I | T | A | N | P | I | V | T | D | K | E | K | 90 |
| ACC | CAG | AAT | GGG | AGA | TTG | ATA | ACA | GCC | AAT | CCC | ATA | GTT | ACT | GAC | AAA | GAA | AAA | 270 |
| P | V | N | I | E | T | E | P | P | F | G | E | S | Y | I | I | V | G | 108 |
| CCA | GTC | AAC | ATT | GAG | ACA | GAA | CCA | CCT | TTT | GGT | GAG | AGC | TAC | ATC | ATA | GTA | GGG | 324 |
| A | G | E | K | A | L | K | L | S | W | F | K | R | G | R | I | E | T | 126 |
| GCA | GGT | GAA | AAA | GCT | TTG | AAA | CTA | AGC | TGG | TTC | AAG | CGC | GGC | CGC | ATT | GAA | ACC | 378 |
| W | I | L | R | H | P | * | * | A | R | | | | | | | | | 136 |
| TGG | ATC | TTG | AGA | CAT | CCA | TAG | TAA | GCG | CGC | | | | | | | | | 408 |

FIGURE 11 (SEQ ID NO : 14)
(SEQ ID NO : 15)

```
  R   T   M   L   L   S   V   P   L   L   L   G   L   L   G   L   A   V    18
CGT ACG ATG CTG CTA TCC GTG CCG TTG CTG CTC GGC CTC CTC GGC CTG GCC GTC    54

A   R   S   K   G   T   T   Y   G   M   C   T   E   K   F   S   F   A    36
GCC AGA TCT AAA GGC ACA ACC TAT GGC ATG TGC ACA GAA AAA TTC TCG TTC GCG   108

K   N   P   A   D   T   G   H   G   T   V   V   I   E   L   S   Y   S    54
AAA AAT CCG GCG GAC ACT GGT CAC GGA ACA GTT GTC ATT GAA CTT TCC TAC TCT   162

G   S   D   G   P   C   K   I   P   I   V   S   V   A   S   L   N   D    72
GGG AGT GAT GGC CCT TGC AAA ATT CCG ATT GTC TCC GTT GCG AGC CTC AAT GAC   216

M   T   P   V   G   R   L   V   T   V   N   P   F   V   A   T   S   S    90
ATG ACC CCC GTC GGG CGG CTG GTG ACA GTG AAC CCC TTC GTC GCG ACT TCC AGC   270

A   N   S   K   V   L   V   E   M   E   P   P   F   G   D   S   Y   I   108
GCC AAC TCA AAG GTG CTA GTC GAG ATG GAA CCC CCC TTC GGA GAC TCC TAC ATC   324

V   V   G   R   G   D   K   Q   I   N   H   H   W   H   K   *   R   P   126
GTA GTT GGA AGG GGA GAC AAG CAG ATC AAC CAC CAT TGG CAC AAA TAG CGG CCG   378

L   *   A   R                                                            130
CTA TAA GCG CGC                                                            390
```

(SEQ ID NO: 16)
(SEQ ID NO: 17)

```
  R   T   M   L   L   S   V   P   L   L   L   G   L   L   G   L   A   V    18
CGT ACG ATG CTG CTA TCC GTG CCG TTG CTG CTC GGC CTC CTC GGC CTG GCC GTC    54

A   R   S   K   G   M   S   Y   V   M   C   T   G   S   F   K   L   E    36
GCC AGA TCT AAA GGG ATG TCA TAT GTG ATG TGC ACA GGC TCA TTT AAG CTA GAG   108

K   E   V   A   E   T   Q   H   G   T   V   L   V   Q   V   K   Y   E    54
AAG GAA GTG GCT GAG ACC CAG CAT GGG ACT GTC CTA GTG CAG GTT AAA TAC GAA   162

G   T   D   A   P   C   K   I   P   F   S   T   Q   D   E   K   G   V    72
GGA ACA GAT GCG CCA TGC AAG ATC CCC TTT TCG ACC CAA GAT GAG AAA GGA GTG   216

T   Q   N   G   R   L   I   T   A   N   P   I   V   T   D   K   E   K    90
ACC CAG AAT GGG AGA TTG ATA ACA GCC AAT CCC ATA GTT ACT GAC AAA GAA AAA   270

P   V   N   I   E   T   E   P   P   F   G   E   S   Y   I   I   V   G   108
CCA GTC AAC ATT GAG ACA GAA CCA CCT TTT GGT GAG AGC TAC ATC ATA GTA GGG   324

A   G   E   K   A   L   K   L   S   W   F   K   K   G   S   S   I   G   126
GCA GGT GAA AAA GCT TTG AAA CTA AGC TGG TTC AAG AAA GGA AGC AGC ATA GGG   378

K   M   F   E   A   T   A   G   S   G   G   K   G   M   S   Y   S   144
AAA ATG TTC GAA GCA ACC GCC GGA GGA TCA GGA GGG AAA GGA ATG TCA TAC TCT   432

M   C   T   G   K   F   K   I   V   K   E   I   A   E   T   Q   H   G   162
ATG TGT ACA GGA AAG TTT AAA ATT GTG AAG GAA ATA GCA GAA ACA CAA CAT GGA   486

T   I   V   I   R   V   Q   Y   E   G   D   G   S   P   C   K   I   P   180
ACA ATA GTT ATC AGA GTA CAA TAT GAA GGG GAC GGC TCT CCA TGT AAG ATC CCT   540

F   E   I   M   D   L   E   K   R   H   V   L   G   R   L   I   T   V   198
TTT GAG ATA ATG GAT TTG GAA AAA AGA CAC GTC TTA GGT CGC CTG ATT ACA GTT   594

N   P   I   V   T   E   K   D   S   P   V   N   I   E   A   E   P   P   216
AAC CCG ATC GTA ACA GAA AAA GAT AGC CCA GTC AAC ATA GAA GCA GAA CCT CCA   648

F   G   D   S   Y   I   I   I   G   V   E   P   G   Q   L   K   L   N   234
TTC GGA GAC AGC TAC ATC ATC ATA GGA GTA GAG CCG GGA CAA TTG AAA CTC AAC   702

W   F   K   K   G   S   S   I   G   Q   M   F   E   T   T   M   G   G   252
TGG TTT AAG AAA GGA AGT TCC ATC GGC CAA ATG TTT GAG ACA ACA ATG GGA GGA   756

S   K   G   M   S   Y   A   M   C   L   N   T   F   V   L   K   K   E   270
TCT AAG GGG ATG AGC TAT GCA ATG TGC TTG AAT ACC TTT GTG TTG AAG AAA GAA   810

V   S   E   T   Q   H   G   T   I   L   I   K   V   E   Y   K   G   E   288
GTC TCC GAA ACG CAG CAT GGG ACA ATA CTC ATT AAG GTT GAG TAC AAA GGG GAA   864

D   A   P   C   K   I   P   F   S   T   E   D   G   Q   G   K   A   H   306
GAT GCA CCT TGC AAG ATT CCT TTC TCC ACA GAG GAT GGA CAA GGG AAA GCT CAC   918
```

*FIG. 12A*

(SEQ ID NO: 16)
(SEQ ID NO: 17)

```
  N   G   R   L   I   T   A   N   P   V   V   T   K   K   E   E   P   V    324
AAT GGT AGA CTG ATC ACA GCC AAC CCA GTG GTG ACC AAG AAG GAG GAG CCT GTC    972

N   I   E   A   E   P   P   F   G   E   S   N   I   V   I   G   I   G    342
AAC ATT GAG GCT GAA CCT CCT TTT GGG GAA AGT AAC ATA GTG ATT GGA ATT GGA   1026

D   K   A   L   K   I   N   W   Y   K   K   G   S   S   I   G   K   M    360
GAC AAA GCC TTG AAA ATT AAC TGG TAC AAG AAG GGA AGC TCG ATT GGG AAG ATG   1080

F   E   A   T   A   G   G   S   G   G   K   G   M   S   Y   T   M   C    378
TTC GAG GCC ACT GCC GGT GGT TCT GGT GGT AAG GGA ATG TCA TAC ACG ATG TGC   1134

S   G   K   F   S   I   D   K   E   M   A   E   T   Q   H   G   T   T    396
TCA GGA AAG TTC TCA ATT GAT AAA GAG ATG GCA GAA ACA CAG CAT GGG ACA ACA   1188

V   V   K   V   K   Y   E   G   A   G   A   P   C   K   V   P   I   E    414
GTG GTG AAA GTC AAG TAT GAG GGT GCT GGA GCT CCA TGT AAA GTT CCC ATA GAG   1242

I   R   D   V   N   K   E   K   V   V   G   R   I   I   S   S   T   P    432
ATA AGA GAT GTG AAC AAG GAA AAA GTG GTT GGG CGT ATC ATC TCA TCT ACC CCT   1296

F   A   E   N   T   N   S   V   T   N   I   E   L   E   P   P   F   G    450
TTT GCT GAG AAT ACC AAC AGT GTG ACC AAT ATA GAA TTG GAA CCC CCT TTT GGG   1350

D   S   Y   I   V   I   G   V   G   D   S   A   L   T   L   H   W   F    468
GAT AGC TAC ATA GTA ATA GGT GTA GGA GAC AGT GCA TTA ACA CTC CAT TGG TTC   1404

R   K   G   S   S   I   G   K   M   F   E   S   T   Y   S   G   R   V    486
AGG AAA GGG AGC TCC ATT GGC AAG ATG TTT GAG TCC ACA TAC AGC GGC CGC GTG   1458

E   T   W   A   L   R   H   P   *   *   A   R                            498
GAG ACT TGG GCT TTG AGA CAC CCA TAG TAA GCG CGC                           1494
```

FIG. 12B

FIGURE 13 (SEQ ID NO : 18)

```
CGTACGATGCTGCTATCCGTGCCGTTGCTGCTCGGCCTCCTCGGCCTGGC
CGTCGCCAGATCTAAGGGAACAACCTATGGCGTCTGTTCAAAGGCTTTCA
AGTTTCTTGGGACTCCCGCAGACACAGGTCACGGCACTGTGGTGTTGGAA
TTGCAGTACACTGGCACGGATGGACCTTGCAAAGTTCCTATCTCGTCAGT
GGCTTCATTGAACGACCTAACGCCAGTGGGCAGATTGGTCACTGTCAACC
CTTTTGTTTCAGTGGCCACGGCCAACGCTAAGGTCCTGATTGAATTGGAA
CCACCCTTTGGAGACTCATACATAGTGGTGGGCAGAGGAGAACAACAGAT
TAATCACCATTGGCACAAGTAGCGGCCGCTATAAGCGCGC
```

FIGURE 14 (SEQ ID NO : 19)

```
CGTACGATGCTGCTATCCGTGCCGTTGCTGCTCGGCCTCCTCGGCCTGGC
CGTCGCCAGATCTAAGGGAACAACCTATGGCGTCTGTTCAAAGGCTTTCA
AGTTTCTTGGGACTCCCGCAGACACAGGTCACGGCACTGTGGTGTTGGAA
TTGCAGTACACTGGCACGGATGGACCTTGCAAAGTTCCTATCTCGTCAGT
GGCTTCATTGAACGACCTAACGCCAGTGGGCAGATTGGTCACTGTCAACC
CTTTTGTTTCAGTGGCCACGGCCAACGCTAAGGTCCTGATTGAATTGGAA
CCACCCTTTGGAGACTCATACATAGTGGTGGGCAGAGGAGAACAACAGAT
TAATCACCATTGGCACAAGAGACGCAGTCGGAGGTCACTGACAGTGCAGA
CACACGGAGAAAGCACTCTAGCGAACAAGAAGGGGCTTGGATGGACAGC
ACCAAGGCCACAAGGTATTTGGTAAAAACAGAATCATGGATCTTGAGGAA
CCCTTGATAGCGGCCGCTATAAGCGCGC
```

FIGURE 15 (SEQ ID NO : 20)

```
MLLSVFLLLG LLCLAVADKL CLKGMSYVMC TGSFKLEKEV AETQHGTVLV QVKYEGTDAP    60
CKIPFSTQDE KGVTQNGRLI TANPIVTDKE KPVNIETEPP FGESYIIVGA GEKALKLSWF   120
RRCKRSVALA PHVGLGLETR TETWMSSEGA WKQIQKVETW ALRHPRRDKR DKLQLKGMSY   180
SMCTGKFKIV KEIAETQHGT IVIRVQYEGD GSFCKIPFEI TDLEKRHVLG RLITVNPIVT   240
EKDSPVNIEA EPPFGDSYII VGVEPGQLKL NWFRRDKRSV ALAPHVGLGL ETRTETWMSS   300
EGAWKQIQKV ETWALRHPRR DKRDKLKLKG MSYAMCLNTF VLKKEVSETQ HGTILIKVEY   360
KGEDAPCKIP FSTEDGQGKA HNGRLITANP VVTKKSEPVN IEAEPPFGES NIVIGIGDKA   420
LKINWYRRDK RSVALAPHVG LGLETRTETW MSSEGAWKQI QKVETWALRH PFRDKREKLR   480
IKGMSYTMCS GKFSIDKEMA ETQHGTTVVK VKYEGAGAPC KVPIEIRDVN KEKVVGRIIS   540
SCPLAENTNS VCNIELEPPF GDSYIVIGVG NSALTLHWFR RDKRSVALAP HVGLGLETRT   600
ETWMSSEGAW KQIQKVETWA LRHP                                          624
```

Signal peptide:                      aa 1 to 17

DV1 EDIII:                             aa 18 to 120
DV2 EDIII:                             aa 171 to 273
DV3 EDIII:                             aa 324 to 426
DV4 EDIII:                             aa 477 to 579 ectoM DV1:                            aa 126 to 165
                                            aa 279 to 318
                                            aa 432 to 471
                                            aa 585 to 624 binding segment:                 aa 121 to 125
                                            aa 166 to 170
                                            aa 274 to 278
                                            aa 319 to 323
                                            aa 427 to 431
                                            aa 472 to 476
                                            aa 580 to 584

FIGURE 16 (SEQ ID NO : 21)

```
KLLSVFLLLG LLGLAVADKL TLKGMSYVMC TGSFKLEKEV AETQHGTVLV QVKYEGTDAP    60
CKIPFSTQDE KGVTQNGRLI TANPIVTDKE KPVNIETEPP FGESYIIVGA GEKALKLSWF   120
SVALAPHVSM GLETRTETWM SSEGAWKQIQ KVETWALRHP RRDKRDKLQL KGMSYSMCTG   180
KFKIVKEIAE TQHGTIVIRV QYEGDGSPCK IPFEITDLEK RHVLGRLITV NPIVTEKDSP   240
VNIEAEPPFG DSYIIVGVEP GQLKLNWFSV ALAPHVGLGL ETRTETWMSS EGAWKQIQKV   300
ETWALRHPRR DKRDKLKLKG MSYAMCLNTF VLKKEVSETQ HGTILIKVEY KGEDAPCKIP   360
FSTEDGQGKA HNGRLITANP VVTKKEEPVN IEAEPPFGKS KIVIGIGDKA LKINNYSVAL   420
APHVGLGLET RTETWMSSEG AWKQICKVET WALRHPRRDK REKLRIKGMS YTMCSGKFSI   480
DKEMAETQHG TTVVKVKYEG AGAPCKVPIE IRDVNKEKVV GRIISSTPLA ENTNSVTNIE   540
LEPPFGDSYI VIGVGNSALT LHWFRRDKRS VALAPHVGLG LECRTETWMS SEGAWKQICK   600
VETWALRHP                                                          609
```

| | |
|---|---|
| Signal peptide: | aa 1 to 17 |
| DV1 EDIII: | aa 18 to 120 |
| DV2 EDIII: | aa 166 to 268 |
| DV3 EDIII: | aa 314 to 416 |
| DV4 EDIII: | aa 462 to 563 |
| ectoM DV1: | aa 121 to 160 |
| | aa 269 to 308 |
| | aa 417 to 456 |
| | aa 570 to 609 |
| binding segment: | aa 161 to 165 |
| | aa 309 to 313 |
| | aa 457 to 461 |
| | aa 564 to 569 |

FIGURE 17 (SEQ ID NO : 22)

```
MLLSVPLLLG LLGLAVADKL TLKGMSYVMC TGSFKLEKEV AETQHGTVLV QVKYEGTDAP    60
CKIPFSTQDE KGVTQNGRLI TANPIVTDKE KPVNIETEPP FGESYIIVGA GEKALKLSWF   120
RRDKRSVALA PHVGLGLETR TETWMSSEGA WKQIQKVETW ALRHPRRDKR DKLQLKGMSY   180
SMCTGKFKIV KEIAETQHGT IVIRVQYEGD GSPCKIPFEI TDLEKRHVLG RLITVNPIVT   240
EKDSPVNIEA EPPFGDSYII VGVEPGQLKL NWFRREKRSV ALVPHVGMGL ETRTETWMSS   300
EGAWKHVQRI ETWILRHPRR DKRDKLKLKG MSYAMCLNTF VLKKEVSETQ HGTILIKVEY   360
KGEDAPCKIP FSTEDGQGKA HNGRLITANP VVTKKEEPVN IEAEPPFGES NIVIGIGDKA   420
LKINWYRRDK RSVALAPHVG MGLDTRTQTW MSAEGAWRQV EKVETWALRH PRRDKREKLR   480
IKGMSYTMCS GKFSIDKEMA ETQHGTTVVK VKYEGAGAPC KVPIEIRDVN KEKVVGRIIS   540
STPLAENTNS VTNIELEPPF GDSYIVIGVG NSALTLHWFR REKRSVALTP HSGMGLETRA   600
ETWMSSEGAW KHAQRVESWI LRNP                                          624
```

| | |
|---|---|
| Signal peptide: | aa 1 to 17 |
| DV1 EDIII: | aa 18 to 120 |
| DV2 EDIII: | aa 171 to 273 |
| DV3 EDIII: | aa 324 to 426 |
| DV4 EDIII: | aa 477 to 579 |
| ectoM DV1: | aa 126 to 165 |
| ectoM DV2: | aa 279 to 318 |
| ectoM DV3: | aa 432 to 471 |
| ectoM DV4: | aa 585 to 624 |
| binding segment: | aa 121 to 125 |
| | aa 166 to 170 |
| | aa 274 to 278 |
| | aa 319 to 323 |
| | aa 427 to 431 |
| | aa 472 to 476 |
| | aa 580 to 584 |

FIGURE 18 (SEQ ID NO : 23)

```
MLLSVPLLLG LLGLAVADKL TLKGMSYVMC TGSFKLEKEV AETQHGTVLV QVKYEGTDAP    60
CKIPFSTQDE KGVTQNGRLI TANPIVTDKE KPVNIETEPP FGESYIIVGA GEKALKLSWF   120
RRDKRDKLQL KGMSYSMCTG KFKIVKEIAE TQHGTIVIRV QYEGDGSPCK IPFEITDLEK   180
RHVLGRLITV NPIVTEKDSP VNIEAEPPFG DSYIIVGVEP GQLKLNWFRR CKRDKLKLKG   240
MSYAMCLNTF VLKKEVSETQ HGTILIKVEY KGEDAPCKIP FSTEDGQGKA HNGRLITANP   300
VVTKKEEPVN IEAEPPFGES NIVIGIGDKA LKINWYRRDK REKLRIKGMS YTMCSGKFSI   360
DKEMAETQHG TTVVKVKYEG AGAPCKVPIE IRDVNKEKVV GRIISSTPLA ENTNSVTNIE   420
LEPPFGDSYI VIGVGNSALT LHWFRRDKRS VALAPHVGLG LETRTETWMS SEGAWKQICK   480
VETWALRHP                                                          489
```

| | |
|---|---|
| Signal peptide: | aa 1 to 17 |
| DV1 EDIII: | aa 18 to 120 |
| DV2 EDIII: | aa 126 to 228 |
| DV3 EDIII: | aa 234 to 336 |
| DV4 EDIII: | aa 342 to 444 |
| ectoM DV1: | aa 450 to 489 |
| binding segment: | aa 121 to 125 |
| | aa 229 to 233 |
| | aa 337 to 341 |
| | aa 445 to 449 |

FIGURE 19 (SEQ ID NO : 24)

```
MLLSVPLLLG LLGLAVADKL TLKGMSYVMC TGSFKLSKEV AETQHGTVLV QVKYEGTDAP    60
CKIPFSTQDE KGVTQNGRLI TANPIVTDKE KPVNIETEPP FGESYIIVGA GEKALKLSWF   120
DKLQLKGMSY SMCTGKFKIV KEIAETQHGT IVIRVQYEGD GSPCKIPFEI TDLEKRHVLG   180
RLITVNPIVT EKDSPVNIEA EPPFGDSYII VGVEPGQLKL NWFDKLKLKG MSYAMCLNTF   240
VLKKEVSETQ HGTILIKVEY KGEDAPCKIP FSTEDGQGKA HNGRLITANP VVTKKEEPVN   300
IEAEPPFGES NIVIGIGDKA LKINWYKKLR IKGMSYTMCS GKFSIDKEMA ETQHGTTVVK   360
VKYEGAGAPC KVPIEIRDVN KEKVVGRIIS STPLAENTNS VTNIELEPPF GDSYIVIGVG   420
HSALTLHWFR RDKRSVALAP HVGLGLETRT ETWKSSEGAW KQIQKVETWA LRHP         474
```

Peptide signal:           aa 1 to 17

DV1 EDIII:                aa 18 to 120
DV2 EDIII:                aa 121 to 223
DV3 EDIII:                aa 224 to 326
DV4 EDIII:                aa 327 to 429 ectoM DV1:                aa 435 to 474 binding segment:          aa 430 to 434

FIGURE 20 (SEQ ID NO : 25)

```
cgtacgatgc tcctttccgt cccgttgcta ttaggactac tcgggttggc tgtcgccgat    60
aagctgactc tgaagggaat gtcatacgtt atgtgcacag ggagcttcaa gttggagaag   120
gaggtggcag agacccagca cggaacagtc ttggtgcagg tcaagtacga gggcacggac   180
gctccttgta agatcccatt ctcaacccag gatgagaagg gcgtgaccca gaatggacgg   240
ctgatcacgg ctaatcccat cgtgactgat aaggagaagc cagtcaacat cgagacagag   300
ccaccottcg gtgagtctta cataatagtc ggggccggag agaaggctct caagctgagt   360
tggttcaggc gggataagcg aagcgtcgca cttgccccac acgttggcct cggactcgag   420
acaagaacag agacctggat gagcagcgag ggagcctgga agcagattca gaaggttgag   480
acctgggctc tccggcaccc tcgccgtgat aagagagaca agctgcagct taagggatg    540
agttattcca tgtgcacagg caagttcaag attgtcaagg agatagcaga gactcagcac   600
ggaaccatag tgatcagagt tcagtacgag ggagacggat ccccatgcaa gattccgttt   660
gagattaccg acctggagaa gcgccacgtg ctggggagac tcattactgt gaacccaatc   720
gtgactgaga aggattctcc cgtcaatatc gaggctgagc caccattcgg agattcttat   780
ataatcgttg gtgtagagcc tggccagttg aagttgaatt ggtttaggcg ggataagagg   840
agcgtggctc tcgctccaca tgttggcctg ggcctggaga cccgaacaga gacgtggatg   900
agctccgaag gtgcctggaa gcagattcag aaggttgaga cctgggccct gcgacaccct   960
agacgggata agcgcgataa gctgaagctt aagggtatgt cctacgcaat gtgcctgaac  1020
acgttcgtgc tgaagaagga ggtttcagag acccagcacg ggacaattct cattaaggtg  1080
gagtacaagg gcgaggacgc gccctgcaag atcccgttca gtactgaaga tggacagggc  1140
aaggctcaca atgggcgact cattactgct aatccagtgg tgaccaagaa ggaagagcca  1200
gtgaatatag aggcagagcc accatttgga gagagcaaca tcgtgatagg tatcggcgat  1260
aaggcactga agatcaactg gtatcgccgc gacaagcgat ccgtggcatt ggcgcctcat  1320
gtgggcctgg gtctagagac ccgcacagag acgtggatga gtagcgaagg cgcgtggaag  1380
cagatccaga aggtcgagac ttgggcactg cggcaccctc gacgtgacaa gcgagagaag  1440
ctccgaatca agggaatgag ttacacaatg tgcagcggca agttctcaat tgataaggag  1500
atggccgaga cccagcacgg cacaaccgtg gtcaaggtca agtacgaagg tgcgggcgct  1560
ccttgcaagg tcccaatcga gattagggat gtgaacaagg agaaggtcgt gggaagaatc  1620
attagttcca cgcctcttgc tgagaacact aatagtgtca ccaatatcga gctagagcca  1680
ccottcggag attcttacat tgtcattgga gttggcaatt ccgctcttac tctgcattgg  1740
tttaggagag ataagagaag cgtggccctg gcaccacacg tgggattagg gctggagaca  1800
cgaaccgaga cctggatgag cagcgaagga gcctggaagc agattcagaa ggtcgagact  1860
tgggccctca gacacccttg atgagcgcgc                                   1890
```

FIGURE 21 (SEQ ID NO : 26)

```
cgtacgatgc tgttgagcgt gccattattg ctggggctgc tgggtctggc tgtggccgac      60
aagcttaccc tgaagggtat gagctacgtg atgtgcactg gttcgttcaa gctagagaag     120
gaggtggcag agacccagca tggaactgtg ttagtacaag ttaagtatga ggggaccgac     180
gcaccctgta agattccatt ctctacccaa gacgagaagg gcgtcacgca gaatggtcgc     240
ttgattacgg ctaatccaat agtgacggac aaggagaagc cagtgaatat cgagacagaa     300
cctccatttg gagaatccta cataatagtc ggggccggcg agaaggccct gaagttgtcc     360
tggttcagcg tggccctggc tccacacgtg ggcctgggcc tggagacccg aactgagact     420
tggatgtcgt ccgagggcgc ctggaagcag atccagaagg tagagacttg ggccctgcgc     480
catcctagga gagataagag ggacaagttg cagctcaagg gcatgtccta ctccatgtgt     540
acaggtaagt tcaagattgt gaaggagatt gctgagaccc agcacggcac catcgtaata     600
cgggtgcagt acgagggcga tggcagtcca tgtaagatac ctttcgagat cactgacctt     660
gagaagcgcc acgtgcttgg gcggctcatt accgtcaatc caatcgtgac tgagaaggat     720
agtccggtga atattgaggc tgagccgccg tttggggata gttatataat cgttggcgtg     780
gagcccggac aactcaagtt gaattggttc tctgtggcct tggcaccaca cgtggggctg     840
ggcctggaga cacggaccga gacttggatg tcaagtgaag gagcctggaa gcagattcag     900
aaggtggaga cttgggccct tcggcaccct agacgtgata agcgcgacaa gctgaagctc     960
aagggaatgt cttacgccat gtgtctgaat actttcgtcc tgaagaagga ggtgtccgag    1020
actcagcatg ggactatcct gatcaaggtg gagtacaagg gtgaagacgc accatgtaag    1080
ataccattca gcacagagga cggtcagggc aaggctcata acgggcgcct tataactgcc    1140
aatccggttg tgaccaagaa ggaggagccc gtgaacatcg aggcagagcc accattcggc    1200
gagtccaaca tcgtgatagg aatcggtgat aaggccctca agattaattg gtattcagtg    1260
gccctggccc ctcacgtcgg actgggactc gagaccagga cagagacatg gatgtcttct    1320
gagggtgcat ggaagcagat acagaaggtt gagacctggg ccctcaggca cccacgtagg    1380
gacaagcggg agaagttgag gattaagggg atgtcgtaca ccatgtgcag cggcaagttc    1440
tccattgaca aggagatggc agagacgcag cacggaacaa cggtcgttaa ggtcaagtac    1500
gaaggagcgg gcgccccatg caaggtccca atcgagatta gggacgtgaa caaggagaag    1560
gttgtaggac ggattattag tagcacccca ctggcggaga atacgaatag tgtcacgaat    1620
atcgaactgg aaccaccttt cggcgatagc tacatcgtga ttggtgttgg caattccgca    1680
cttacactgc actggtttcg gagagacaag cgaagcgtgg ccctggcccc tcacgtggga    1740
cttggcctgg agacccgcac agagacttgg atgtcctctg aaggagcatg gaagcagatt    1800
cagaaggtgg agacttgggc attacgccac ccatgagcgc gc                       1842
```

FIGURE 22 (SEQ ID NO : 27)

```
cgtacgatgc tgctatctgt gccactgctc ctgggactgc tggggctggc cgtggctgac      60
aagttgacgc ttaaggggat gtcctacgta atgtgcacag gatcattcaa gctagagaag     120
gaagttgcag agacgcagca cggcaccgtg ctggttcagg tgaagtacga gggcactgat     180
gcaccctgca agatcccatt cagtactcag gacgagaagg gagtcacgca gaatgggagg     240
ctcatcacgg ccaacccaat tgttaccgac aaggagaagc ccgttaatat agagactgaa     300
ccgcccttcg gggagtcata cattattgtg ggcgcagggg agaaggctct gaagctttcc     360
tggttccgta gggataagcg cagcgtggcg ctagcccctc atgtgggtct cgggctggag     420
actcgcaccg agacatggat gtcatccgag ggtgcgtgga agcagatcca gaaggttgag     480
acatgggcac ttcgccaccc acggcgcgac aagcgtgaca agcttcagct gaaggggatg     540
tcttatagca tgtgcacagg caagttcaag atcgtcaagg agatagcaga gacacagcat     600
ggcacaatag tcatacgggt gcaatatgag ggagatggct ctccgtgtaa gatacctttc     660
gagatcaccg atctggagaa gcggcacgtc ctcgggagac taattacggt gaacccaatt     720
gtgacagaga aggatagccc agttaatatt gaggccgaac caccccttcgg agacagctac     780
attatcgtag gagtcgagcc agggcagctg aagctgaact ggttccgcag gggagaagcgt     840
tccgtcgctc ttgttccaca tgtgggaatg ggcctggaga cccgcaccga gacatggatg     900
agcagcgagg gtgcctggaa gcacgtacag agaattgaga cttggatctt aaggcatcct     960
cggcgggata agcgcgacaa gttgaagctg aagggaatgt cttacgcaat gtgtttgaac    1020
actttcgtcc tgaagaagga ggtgtcagag acccagcacg gaactatact tattaaggtt    1080
gagtacaagg gagaagacgc tccttgcaag atcccattct caactgaaga tgggcagggc    1140
aaggcacaca acggaaggct catcacagct aacccagtgg ttaccaagaa ggagagagccc    1200
gtgaacatcg aagccgagcc gcccttcgga gagagcaaca tagtgatcgg tattggggat    1260
aaggctctga agatcaattg gtatcgccgg gacaagagaa gtgtggccct ggccccacat    1320
gtcggcatgg gcttggacac acggacacag acatggatgt ccgctgaagg agcctggagg    1380
caggtggaga aggtcgagac ctgggcgctg cgccacccgc gtcgagacaa gagagagaag    1440
ttaagaatca agggtatgtc ctacacgatg tgttccggta agttctccat agacaaggag    1500
atggctgaga cccagcacgg cactacggtg gtcaaggtga agtatgaggg agccggcgca    1560
ccttgcaagg tgccgatcga gatccgcgac gtcaacaagg agaaggtggt cgggcgcatc    1620
atttccagta ccccattagc tgagaatact aatagcgtga ctaatattga gttggaacca    1680
cccttcggag actcttacat cgttatcggg gtgggcaact cagctcttac acttcactgg    1740
ttccgcaggg agaagagatc agtggcccta accctcact caggcatggg cctggagact    1800
cgggccgaga cctggatgag cagcgagggt gcctggaagc acgcccagcg agtggaatcg    1860
tggattctta ggaatccatg atgagcgcgc                                     1890
```

FIGURE 23 (SEQ ID NO : 28)

```
cgtacgatgc tgttatctgt acctctcctg ctcggcctcc ttggactggc agttgcagat      60
aagcttacac tcaagggaat gtcctatgtg atgtgtaccg ggtccttcaa gttggagaag     120
gaggtagctg agacgcagca tggcacagtg ctggtgcagg ttaagtatga aggaactgat     180
gctccgtgta agatcccgtt cagtactcag gatgagaagg gtgtgaccca gaatggccgc     240
ttaattacag ccaaccctat cgtaactgac aaggagaagc ctgtgaacat cgagactgaa     300
ccacccttcg gtgagagtta tataatagtt ggcgccggag agaaggccct caagcttagc     360
tggtttcggc gcgacaagcg agataagctc caacttaagg gaatgtcata ctcaatgtgc     420
acaggtaagt tcaagatagt gaaggagata gccgagaccc agcatggcac catcgtgatc     480
agagtccaat atgaaggaga cgggtctcct tgtaagatcc cattcgagat aacagacttg     540
gagaagaggc acgtgctggg acgtctgata acagttaatc ccatagttac cgagaaggat     600
agccctgtta acattgaggc tgaacctccc ttcggagatt cctacattat tgtcggcgtg     660
gagccaggtc agctgaagct taactggttc agacgggaca agcgcgacaa gctgaagttg     720
aagggcatgt cctatgcaat gtgtctcaat actttcgttc tcaagaagga agtgagcgag     780
acacagcatg gcaccatatt aattaaggtt gagtacaagg gtgaggatgc tccttgcaag     840
attcctttca gcaccgagga tggacagggc aaggcccaca atggtcggct gatcaccgcc     900
aaccctgtgg taaccaagaa ggaagagccc gtcaacatag aagccgagcc gccgtttggc     960
gagtccaata tagtaatcgg catcgagat aaggccttga agattaattg gtacaggcgg    1020
gataagcgcg agaagttacg gattaagggt atgtcttaca ctatgtgtag cggtaagttt    1080
agcatcgaca aggagatggc agagacccag catggcacta ccgtggtcaa ggtgaagtac    1140
gaaggagctg gagcaccatg taaggtccct atcgagatcc gcgacgtgaa caaggagaag    1200
gtggtgggaa gaatcatctc ttccacacct ctggcagaga acacgaatag cgtgactaat    1260
atcgaacttg agcctccttt cggcgattcc tacatcgtta ttggcgtggg caactccgcc    1320
ctgacactgc attggtttag acgtgacaag cgtagcgtgg cccttgcacc acacgtgggc    1380
ctaggcctgg agacgcgtac agagacatgg atgagcagtg aaggagcctg gaagcagatt    1440
cagaaggtcg agacctgggc tctcagacat ccttgagcgc gc                       1482
```

FIGURE 24 (SEQ ID NO : 29)

```
cgtacgatgc tcctaagcgt tccactgctt ctgggactgc tgggtttggc cgttgccgac     60
aagctcacgc tcaaggggat gagctacgtc atgtgcacag gctcattcaa gttggagaag    120
gaagtcgccg agacgcagca cggaacagta ctcgtgcagg tcaagtatga gggcaccgac    180
gctccatgca agatccgtt  ctccacacag gacgagaagg gcgttactca gaacggaaga    240
ttaattactg ccaatcctat agtaacagac aaggagaagc ctgtgaatat tgagactgag    300
cctcccttcg gtgaatccta catcattgta ggggctggcg agaaggcttt gaagctctcc    360
tggtttgata agctgcagct caagggaatg tcgtattcaa tgtgcactgg gaagttcaag    420
attgtgaagg agattgcaga gactcaacac ggcaccattg tgataagggt ccagtacgag    480
ggtgatgggt caccctgcaa gattcccttt gagatcacag accttgagaa gaggcacgta    540
cttgggcgat taattaccgt gaatcctatt gtgactgaga aggatagtcc cgtgaacatt    600
gaagctgagc ctccttcgg  agatagctac attatcgtgg gagtcgagcc tggccagttg    660
aagctcaact ggtttgataa gctgaagctc aagggcatgt cctacgctat gtgcttgaat    720
acatttgtgc tgaagaagga ggtgagtgag acccaacacg gaaccatcct gatcaaggtg    780
gagtacaagg gtgaagatgc accttgcaag atccctttct ccactgaaga cgggcagggc    840
aaggcccata atgggagact cataacagct aatccagtgg tcaccaagaa ggaagaacca    900
gtcaacatcg aggcggagcc accatttggg gagagtaaca tcgtgatcgg tattggcgat    960
aaggccctga agattaactg gtatgagaag ttgagaatta aggggatgag ctataccatg   1020
tgctcaggta agttcagcat cgataaggag atggccgaga cacagcacgg gaccacagtt   1080
gtgaaggtga agtacgaggg cgctggggcc ccatgcaagg tgcctatcga gattcgcgac   1140
gtgaacaagg agaaggtcgt ggggcgaatc atctcatcca ccctctcgc  agagaacacg   1200
aactctgtga ccaatattga gctggaacca cctttcggag actcatatat cgtcataggc   1260
gtcggcaatt cagctttgac attgcactgg ttcagacggg acaagcggtc cgttgccctg   1320
gctccacacg tcggcctggg ccttgagact aggacggaga cctggatgtc ctccgagggc   1380
gcctggaagc agatccagaa ggtggagacc tgggccctgc gccaccctg  ataggcgcgc   1440
```

DV-1 (FGA89)     (SEQ ID NO : 30)
SVALAPHVGLGLETRTETWMSSEGAWKQIQKVETWALRHP

DV-3 (PAH881)     (SEQ ID NO : 31)
SVALAPHVGMGLDTRTQTWMSAEGAWRQVEKVETWALRHP

DV-4 (63632)     (SEQ ID NO : 32)
SVALTPHSGMGLETRAETWMSSEGAWKHAQRVESWILRNP

DV-2 (Jam/Camb)  (SEQ ID NO : 33)
SVALVPHVGMGLETRTETWMSSEGAWKHAQRIETWILRHP

SEQUENCE LISTING

<160> NUMBER OF SEQ ID NOS: 35

<210> SEQ ID NO 1
<211> LENGTH: 119
<212> TYPE: PRT
<213> ORGANISM: Artificial Sequence
<220> FEATURE:
<223> OTHER INFORMATION: Description of Artificial Sequence: Synthetic
    fusion sequence comprising domain(s) of Flaviviridae
    strains

<400> SEQUENCE: 1

Met Leu Leu Ser Val Pro Leu Leu Leu Gly Leu Leu Gly Leu Ala Val
1               5                   10                  15

Ala Arg Ser Lys Gly Met Ser Tyr Val Met Cys Thr Gly Ser Phe Lys
            20                  25                  30

Leu Glu Lys Glu Val Ala Glu Thr Gln His Gly Thr Val Leu Val Gln
        35                  40                  45

Val Lys Tyr Glu Gly Thr Asp Ala Pro Cys Lys Ile Pro Phe Ser Thr
50                  55                  60

Gln Asp Glu Lys Gly Val Thr Gln Asn Gly Arg Leu Ile Thr Ala Asn
65                  70                  75                  80

Pro Ile Val Thr Asp Lys Glu Lys Pro Val Asn Ile Glu Thr Glu Pro
                85                  90                  95

Pro Phe Gly Glu Ser Tyr Ile Ile Val Gly Ala Gly Glu Lys Ala Leu
            100                 105                 110

Lys Leu Ser Trp Phe Lys Arg
        115

<210> SEQ ID NO 2
<211> LENGTH: 384
<212> TYPE: DNA
<213> ORGANISM: Artificial Sequence
<220> FEATURE:
<223> OTHER INFORMATION: Description of Artificial Sequence: Synthetic
    fusion sequence comprising domain(s) of Flaviviridae
    strains
<220> FEATURE:
<221> NAME/KEY: CDS
<222> LOCATION: (7)..(363)

<400> SEQUENCE: 2 cgtacg atg ctg cta tcc gtg ccg ttg ctg ctc ggc ctc ctc ggc ctg       48
       Met Leu Leu Ser Val Pro Leu Leu Leu Gly Leu Leu Gly Leu
       1               5                   10 gcc gtc gcc aga tct aaa ggg atg tca tat gtg atg tgc aca ggc tca      96
Ala Val Ala Arg Ser Lys Gly Met Ser Tyr Val Met Cys Thr Gly Ser
15                  20                  25                  30 ttt aag cta gag aag gaa gtg gct gag acc cag cat ggg act gtc cta     144
Phe Lys Leu Glu Lys Glu Val Ala Glu Thr Gln His Gly Thr Val Leu
                35                  40                  45 gtg cag gtt aaa tac gaa gga aca gat gcg cca tgc aag atc ccc ttt     192
Val Gln Val Lys Tyr Glu Gly Thr Asp Ala Pro Cys Lys Ile Pro Phe
        50                  55                  60 tcg acc caa gat gag aaa gga gtg acc cag aat ggg aga ttg ata aca     240
Ser Thr Gln Asp Glu Lys Gly Val Thr Gln Asn Gly Arg Leu Ile Thr
65                  70                  75 gcc aat ccc ata gtt act gac aaa gaa aaa cca gtc aac att gag aca     288
Ala Asn Pro Ile Val Thr Asp Lys Glu Lys Pro Val Asn Ile Glu Thr
            80                  85                  90 gaa cca cct ttt ggt gag agc tac atc ata gta ggg gca ggt gaa aaa     336
Glu Pro Pro Phe Gly Glu Ser Tyr Ile Ile Val Gly Ala Gly Glu Lys
95                  100                 105                 110 gct ttg aaa cta agc tgg ttc aag cga tagcggccgc tataagcgcg c         384
Ala Leu Lys Leu Ser Trp Phe Lys Arg
                115

<210> SEQ ID NO 3
<211> LENGTH: 162
<212> TYPE: PRT
<213> ORGANISM: Artificial Sequence
<220> FEATURE:
<223> OTHER INFORMATION: Description of Artificial Sequence: Synthetic
      fusion sequence comprising domain(s) of Flaviviridae
      strains

<400> SEQUENCE: 3

Met Leu Leu Ser Val Pro Leu Leu Gly Leu Leu Gly Leu Ala Val
1               5                   10                  15

Ala Arg Ser Lys Gly Met Ser Tyr Val Met Cys Thr Gly Ser Phe Lys
            20                  25                  30

Leu Glu Lys Glu Val Ala Glu Thr Gln His Gly Thr Val Leu Val Gln
        35                  40                  45

Val Lys Tyr Glu Gly Thr Asp Ala Pro Cys Lys Ile Pro Phe Ser Thr
    50                  55                  60

Gln Asp Glu Lys Gly Val Thr Gln Asn Gly Arg Leu Ile Thr Ala Asn
65                  70                  75                  80

Pro Ile Val Thr Asp Lys Glu Lys Pro Val Asn Ile Glu Thr Glu Pro
                85                  90                  95

Pro Phe Gly Glu Ser Tyr Ile Ile Val Gly Ala Gly Glu Lys Ala Leu
            100                 105                 110

Lys Leu Ser Trp Phe Arg Arg Asp Lys Arg Ser Val Ala Leu Ala Pro
        115                 120                 125

His Val Gly Leu Gly Leu Glu Thr Arg Thr Glu Thr Trp Met Ser Ser
    130                 135                 140

Glu Gly Ala Trp Lys Gln Ile Gln Lys Val Glu Thr Trp Ala Leu Arg
145                 150                 155                 160

His Pro

<210> SEQ ID NO 4
<211> LENGTH: 516
<212> TYPE: DNA
<213> ORGANISM: Artificial Sequence
<220> FEATURE:
<223> OTHER INFORMATION: Description of Artificial Sequence: Synthetic
      fusion sequence comprising domain(s) of Flaviviridae
      strains
<220> FEATURE:
<221> NAME/KEY: CDS
<222> LOCATION: (7)..(492)

<400> SEQUENCE: 4 cgtacg atg ctg cta tcc gtg ccg ttg ctg ctc ggc ctc ctc ggc ctg        48
       Met Leu Leu Ser Val Pro Leu Leu Leu Gly Leu Leu Gly Leu
       1               5                   10 gcc gtc gcc aga tct aaa ggg atg tca tat gtg atg tgc aca ggc tca       96
Ala Val Ala Arg Ser Lys Gly Met Ser Tyr Val Met Cys Thr Gly Ser
15                  20                  25                  30 ttt aag cta gag aag gaa gtg gct gag acc cag cat ggg act gtc cta      144
Phe Lys Leu Glu Lys Glu Val Ala Glu Thr Gln His Gly Thr Val Leu
                35                  40                  45 gtg cag gtt aaa tac gaa gga aca gat gcg cca tgc aag atc ccc ttt      192
Val Gln Val Lys Tyr Glu Gly Thr Asp Ala Pro Cys Lys Ile Pro Phe
            50                  55                  60 tcg acc caa gat gag aaa gga gtg acc cag aat ggg aga ttg ata aca      240
Ser Thr Gln Asp Glu Lys Gly Val Thr Gln Asn Gly Arg Leu Ile Thr
        65                  70                  75 gcc aat ccc ata gtt act gac aaa gaa aaa cca gtc aac att gag aca      288

```
Ala Asn Pro Ile Val Thr Asp Lys Glu Lys Pro Val Asn Ile Glu Thr
     80                  85                  90 gaa cca cct ttt ggt gag agc tac atc ata gta ggg gca ggt gaa aaa      336
Glu Pro Pro Phe Gly Glu Ser Tyr Ile Ile Val Gly Ala Gly Glu Lys
 95                 100                 105                 110 gct ttg aaa cta agc tgg ttc cga cga gac aaa cgt tcc gtg gca ctg      384
Ala Leu Lys Leu Ser Trp Phe Arg Arg Asp Lys Arg Ser Val Ala Leu
                115                 120                 125 gcc cca cac gtg gga ctt ggt cta gaa aca aga acc gaa aca tgg atg      432
Ala Pro His Val Gly Leu Gly Leu Glu Thr Arg Thr Glu Thr Trp Met
            130                 135                 140 tcc tct gaa ggc gcc tgg aaa caa ata caa aaa gtg gag act tgg gct      480
Ser Ser Glu Gly Ala Trp Lys Gln Ile Gln Lys Val Glu Thr Trp Ala
        145                 150                 155 ttg aga cac cca tgatagcggc cgctataagc gcgc                           516
Leu Arg His Pro
    160
```

```
<210> SEQ ID NO 5
<211> LENGTH: 516
<212> TYPE: DNA
<213> ORGANISM: Artificial Sequence
<220> FEATURE:
<223> OTHER INFORMATION: Description of Artificial Sequence: Synthetic
      fusion sequence comprising domain(s) of Flaviviridae
      strains

<400> SEQUENCE: 5
cgtacgatgc tgctatccgt gccgttgctg ctcggcctcc tcggcctggc cgtcgccaga     60
tctaaaggga tgtcatatgt gatgtgcaca ggctcattta agctagagaa ggaagtggct    120
gagacccagc atgggactgt cctagtgcag gttaaatacg aaggaacaga tgcgccatgc    180
aagatcccct tttcgaccca agatgagaaa ggagtgaccc agaatgggag attgataaca    240
gccaatccca tagttactga caaagaaaaa ccagtcaaca ttgagacaga accacctttt    300
ggtgagagct acatcatagt aggggcaggt gaaaaagctt tgaaactaag ctggttccga    360
cgagacaaac gttccgtggc actggcccca cacgtgggac ttggtctaga aacaagaacc    420
gaaacatgga tgtcctctga aggcgcctgg aaacaaatac aaaaagtgga gacttgggct    480
ttgagacacc catgatagcg gccgctataa gcgcgc                              516
```

```
<210> SEQ ID NO 6
<211> LENGTH: 168
<212> TYPE: PRT
<213> ORGANISM: Artificial Sequence
<220> FEATURE:
<223> OTHER INFORMATION: Description of Artificial Sequence: Synthetic
      fusion sequence comprising domain(s) of Flaviviridae
      strains

<400> SEQUENCE: 6

Arg Thr Met Leu Leu Ser Val Pro Leu Leu Leu Gly Leu Leu Gly Leu
  1               5                  10                  15

Ala Val Ala Arg Ser Lys Gly Thr Thr Tyr Gly Met Cys Thr Glu Lys
             20                  25                  30

Phe Ser Phe Ala Lys Asn Pro Ala Asp Thr Gly His Gly Thr Val Val
         35                  40                  45

Ile Glu Leu Ser Tyr Ser Gly Ser Asp Gly Pro Cys Lys Ile Pro Ile
     50                  55                  60

Val Ser Val Ala Ser Leu Asn Asp Met Thr Pro Val Gly Arg Leu Val
 65                  70                  75                  80
```

```
        Thr Val Asn Pro Phe Val Ala Thr Ser Ser Ala Asn Ser Lys Val Leu
                        85                  90                  95

Val Glu Met Glu Pro Pro Phe Gly Asp Ser Tyr Ile Val Val Gly Arg
                    100                 105                 110

Gly Asp Lys Gln Ile Asn His His Trp His Lys Lys Arg Ser Arg Arg
                    115                 120                 125

Ser Val Ser Val Gln Thr His Gly Glu Ser Ser Leu Val Asn Lys Lys
                    130                 135                 140

Glu Ala Trp Leu Asp Ser Thr Lys Ala Thr Arg Tyr Leu Met Lys Thr
        145                 150                 155                 160

Glu Asn Trp Ile Val Arg Asn Pro
                        165

<210> SEQ ID NO 7
<211> LENGTH: 528
<212> TYPE: DNA
<213> ORGANISM: Artificial Sequence
<220> FEATURE:
<223> OTHER INFORMATION: Description of Artificial Sequence: Synthetic
      fusion sequence comprising domain(s) of Flaviviridae
      strains
<220> FEATURE:
<221> NAME/KEY: CDS
<222> LOCATION: (1)..(504)

<400> SEQUENCE: 7 cgt acg atg ctg cta tcc gtg ccg ttg ctg ctc ggc ctc ctc ggc ctg      48
Arg Thr Met Leu Leu Ser Val Pro Leu Leu Leu Gly Leu Leu Gly Leu
1               5                   10                  15 gcc gtc gcc aga tct aaa ggc aca acc tat ggc atg tgc aca gaa aaa      96
Ala Val Ala Arg Ser Lys Gly Thr Thr Tyr Gly Met Cys Thr Glu Lys
            20                  25                  30 ttc tcg ttc gcg aaa aat ccg gcg gac act ggt cac gga aca gtt gtc     144
Phe Ser Phe Ala Lys Asn Pro Ala Asp Thr Gly His Gly Thr Val Val
        35                  40                  45 att gaa ctt tcc tac tct ggg agt gat ggc cct tgc aaa att ccg att     192
Ile Glu Leu Ser Tyr Ser Gly Ser Asp Gly Pro Cys Lys Ile Pro Ile
    50                  55                  60 gtc tcc gtt gcg agc ctc aat gac atg acc ccc gtc ggg cgg ctg gtg     240
Val Ser Val Ala Ser Leu Asn Asp Met Thr Pro Val Gly Arg Leu Val
65                  70                  75                  80 aca gtg aac ccc ttc gtc gcg act tcc agc gcc aac tca aag gtg cta     288
Thr Val Asn Pro Phe Val Ala Thr Ser Ser Ala Asn Ser Lys Val Leu
                85                  90                  95 gtc gag atg gaa ccc ccc ttc gga gac tcc tac atc gta gtt gga agg     336
Val Glu Met Glu Pro Pro Phe Gly Asp Ser Tyr Ile Val Val Gly Arg
            100                 105                 110 gga gac aag cag atc aac cac cat tgg cac aaa aag cga agc agg aga     384
Gly Asp Lys Gln Ile Asn His His Trp His Lys Lys Arg Ser Arg Arg
        115                 120                 125 tcc gtg tcg gtc caa aca cat ggg gag agt tca cta gtg aat aaa aaa     432
Ser Val Ser Val Gln Thr His Gly Glu Ser Ser Leu Val Asn Lys Lys
    130                 135                 140 gag gct tgg ctg gat tca acg aaa gcc aca cga tac ctc atg aaa act     480
Glu Ala Trp Leu Asp Ser Thr Lys Ala Thr Arg Tyr Leu Met Lys Thr
145                 150                 155                 160 gag aac tgg atc gta agg aat cct tgatagcggc cgctataagc gcgc           528
Glu Asn Trp Ile Val Arg Asn Pro
                165
```

```
<210> SEQ ID NO 8
<211> LENGTH: 262
<212> TYPE: PRT
<213> ORGANISM: Artificial Sequence
<220> FEATURE:
<223> OTHER INFORMATION: Description of Artificial Sequence: Synthetic
      fusion sequence comprising domain(s) of Flaviviridae
      strains

<400> SEQUENCE: 8

Arg Thr Met Leu Leu Ser Val Pro Leu Leu Gly Leu Leu Gly Leu
1               5                   10                  15

Ala Val Ala Arg Ser Lys Gly Met Ser Tyr Val Met Cys Thr Gly Ser
            20                  25                  30

Phe Lys Leu Glu Lys Glu Val Ala Glu Thr Gln His Gly Thr Val Leu
                35                  40                  45

Val Gln Val Lys Tyr Glu Gly Thr Asp Ala Pro Cys Lys Ile Pro Phe
50                  55                  60

Ser Thr Gln Asp Glu Lys Gly Val Thr Gln Asn Gly Arg Leu Ile Thr
65                  70                  75                  80

Ala Asn Pro Ile Val Thr Asp Lys Glu Lys Pro Val Asn Ile Glu Thr
                85                  90                  95

Glu Pro Pro Phe Gly Glu Ser Tyr Ile Ile Val Gly Ala Gly Glu Lys
            100                 105                 110

Ala Leu Lys Leu Ser Trp Phe Lys Lys Gly Ser Ser Ile Gly Lys Met
        115                 120                 125

Phe Glu Ala Thr Ala Gly Gly Ser Gly Gly Lys Gly Met Ser Tyr Ser
    130                 135                 140

Met Cys Thr Gly Lys Phe Lys Ile Val Lys Glu Ile Ala Glu Thr Gln
145                 150                 155                 160

His Gly Thr Ile Val Ile Arg Val Gln Tyr Glu Gly Asp Gly Ser Pro
                165                 170                 175

Cys Lys Ile Pro Phe Glu Ile Met Asp Leu Glu Lys Arg His Val Leu
            180                 185                 190

Gly Arg Leu Ile Thr Val Asn Pro Ile Val Thr Glu Lys Asp Ser Pro
        195                 200                 205

Val Asn Ile Glu Ala Glu Pro Pro Phe Gly Asp Ser Tyr Ile Ile Ile
    210                 215                 220

Gly Val Glu Pro Gly Gln Leu Lys Leu Asn Trp Phe Lys Lys Gly Ser
225                 230                 235                 240

Ser Ile Gly Gln Met Phe Glu Thr Thr Met Ser Gly Arg Val Glu Thr
                245                 250                 255

Trp Ala Leu Arg His Pro
            260

<210> SEQ ID NO 9
<211> LENGTH: 798
<212> TYPE: DNA
<213> ORGANISM: Artificial Sequence
<220> FEATURE:
<223> OTHER INFORMATION: Description of Artificial Sequence: Synthetic
      fusion sequence comprising domain(s) of Flaviviridae
      strains
<220> FEATURE:
<221> NAME/KEY: CDS
<222> LOCATION: (1)..(786)

<400> SEQUENCE: 9 cgt acg atg ctg cta tcc gtg ccg ttg ctg ctc ggc ctc ctc ggc ctg      48
Arg Thr Met Leu Leu Ser Val Pro Leu Leu Leu Gly Leu Leu Gly Leu
```

```
           1               5                      10                       15
    gcc gtc gcc aga tct aaa ggg atg tca tat gtg atg tgc aca ggc tca        96
    Ala Val Ala Arg Ser Lys Gly Met Ser Tyr Val Met Cys Thr Gly Ser
                    20                  25                  30 ttt aag cta gag aag gaa gtg gct gag acc cag cat ggg act gtc cta       144
    Phe Lys Leu Glu Lys Glu Val Ala Glu Thr Gln His Gly Thr Val Leu
                    35                  40                  45 gtg cag gtt aaa tac gaa gga aca gat gcg cca tgc aag atc ccc ttt       192
    Val Gln Val Lys Tyr Glu Gly Thr Asp Ala Pro Cys Lys Ile Pro Phe
        50                  55                  60 tcg acc caa gat gag aaa gga gtg acc cag aat ggg aga ttg ata aca       240
    Ser Thr Gln Asp Glu Lys Gly Val Thr Gln Asn Gly Arg Leu Ile Thr
    65                  70                  75                  80 gcc aat ccc ata gtt act gac aaa gaa aaa cca gtc aac att gag aca       288
    Ala Asn Pro Ile Val Thr Asp Lys Glu Lys Pro Val Asn Ile Glu Thr
                        85                  90                  95 gaa cca cct ttt ggt gag agc tac atc ata gta ggg gca ggt gaa aaa       336
    Glu Pro Pro Phe Gly Glu Ser Tyr Ile Ile Val Gly Ala Gly Glu Lys
                    100                 105                 110 gct ttg aaa cta agc tgg ttc aag aaa gga agc agc ata ggg aaa atg       384
    Ala Leu Lys Leu Ser Trp Phe Lys Lys Gly Ser Ser Ile Gly Lys Met
                115                 120                 125 ttc gaa gca acc gcc gga gga tca gga ggg aaa gga atg tca tac tct       432
    Phe Glu Ala Thr Ala Gly Gly Ser Gly Gly Lys Gly Met Ser Tyr Ser
            130                 135                 140 atg tgt aca gga aag ttt aaa att gtg aag gaa ata gca gaa aca caa       480
    Met Cys Thr Gly Lys Phe Lys Ile Val Lys Glu Ile Ala Glu Thr Gln
    145                 150                 155                 160 cat gga aca ata gtt atc aga gta caa tat gaa ggg gac ggc tct cca       528
    His Gly Thr Ile Val Ile Arg Val Gln Tyr Glu Gly Asp Gly Ser Pro
                    165                 170                 175 tgt aag atc cct ttt gag ata atg gat ttg gaa aaa aga cac gtc tta       576
    Cys Lys Ile Pro Phe Glu Ile Met Asp Leu Glu Lys Arg His Val Leu
                180                 185                 190 ggt cgc ctg att aca gtt aac ccg atc gta aca gaa aaa gat agc cca       624
    Gly Arg Leu Ile Thr Val Asn Pro Ile Val Thr Glu Lys Asp Ser Pro
            195                 200                 205 gtc aac ata gaa gca gaa cct cca ttc gga gac agc tac atc atc ata       672
    Val Asn Ile Glu Ala Glu Pro Pro Phe Gly Asp Ser Tyr Ile Ile Ile
    210                 215                 220 gga gta gag ccg gga caa ttg aaa ctc aac tgg ttt aag aaa gga agt       720
    Gly Val Glu Pro Gly Gln Leu Lys Leu Asn Trp Phe Lys Lys Gly Ser
                    225                 230                 235                 240 tcc atc ggc caa atg ttt gag aca aca atg agc ggc cgc gtg gag act       768
    Ser Ile Gly Gln Met Phe Glu Thr Thr Met Ser Gly Arg Val Glu Thr
                    245                 250                 255 tgg gct ttg aga cac cca tagtaagcgc gc                                 798
    Trp Ala Leu Arg His Pro
                260
```

<210> SEQ ID NO 10
<211> LENGTH: 262
<212> TYPE: PRT
<213> ORGANISM: Artificial Sequence
<220> FEATURE:
<223> OTHER INFORMATION: Description of Artificial Sequence: Synthetic
      fusion sequence comprising domain(s) of Flaviviridae
      strains

<400> SEQUENCE: 10

Arg Thr Met Leu Leu Ser Val Pro Leu Leu Leu Gly Leu Leu Gly Leu

```
  1               5                  10                 15
Ala Val Ala Arg Ser Lys Gly Met Ser Tyr Ala Met Cys Leu Asn Thr
            20                  25                 30
Phe Val Leu Lys Lys Glu Val Ser Glu Thr Gln His Gly Thr Ile Leu
            35                  40                 45
Ile Lys Val Glu Tyr Lys Gly Glu Asp Ala Pro Cys Lys Ile Pro Phe
 50                  55                 60
Ser Thr Glu Asp Gly Gln Gly Lys Ala His Asn Gly Arg Leu Ile Thr
 65                  70                 75                 80
Ala Asn Pro Val Val Thr Lys Lys Glu Pro Val Asn Ile Glu Ala
                85                  90                 95
Glu Pro Pro Phe Gly Glu Ser Asn Ile Val Ile Gly Ile Gly Asp Lys
            100                 105                110
Ala Leu Lys Ile Asn Trp Tyr Lys Lys Gly Ser Ser Ile Gly Lys Met
            115                 120                125
Phe Glu Ala Thr Ala Gly Gly Ser Gly Gly Lys Gly Met Ser Tyr Thr
            130                 135                140
Met Cys Ser Gly Lys Phe Ser Ile Asp Lys Glu Met Ala Glu Thr Gln
145                 150                 155                160
His Gly Thr Thr Val Val Lys Val Lys Tyr Glu Gly Ala Gly Ala Pro
                165                 170                175
Cys Lys Val Pro Ile Glu Ile Arg Asp Val Asn Lys Glu Lys Val Val
            180                 185                190
Gly Arg Ile Ile Ser Ser Thr Pro Phe Ala Glu Asn Thr Asn Ser Val
            195                 200                205
Thr Asn Ile Glu Leu Glu Pro Pro Phe Gly Asp Ser Tyr Ile Val Ile
210                 215                 220
Gly Val Gly Asp Ser Ala Leu Thr Leu His Trp Phe Arg Lys Gly Ser
225                 230                 235                240
Ser Ile Gly Lys Met Phe Glu Ser Thr Tyr Ser Gly Arg Val Glu Thr
            245                 250                255
Trp Ala Leu Arg His Pro
            260
```

<210> SEQ ID NO 11
<211> LENGTH: 798
<212> TYPE: DNA
<213> ORGANISM: Artificial Sequence
<220> FEATURE:
<223> OTHER INFORMATION: Description of Artificial Sequence: Synthetic
      fusion sequence comprising domain(s) of Flaviviridae
      strains
<220> FEATURE:
<221> NAME/KEY: CDS
<222> LOCATION: (1)..(786)

<400> SEQUENCE: 11

```
cgt acg atg ctg cta tcc gtg ccg ttg ctg ctc ggc ctc ctc ggc ctg      48
Arg Thr Met Leu Leu Ser Val Pro Leu Leu Leu Gly Leu Leu Gly Leu
 1               5                  10                 15 gcc gtc gcc aga tct aag ggg atg agc tat gca atg tgc ttg aat acc      96
Ala Val Ala Arg Ser Lys Gly Met Ser Tyr Ala Met Cys Leu Asn Thr
            20                  25                 30 ttt gtg ttg aag aaa gaa gtc tcc gaa acg cag cat ggg aca ata ctc     144
Phe Val Leu Lys Lys Glu Val Ser Glu Thr Gln His Gly Thr Ile Leu
            35                  40                 45 att aag gtt gag tac aaa ggg gaa gat gca cct tgc aag att cct ttc     192
Ile Lys Val Glu Tyr Lys Gly Glu Asp Ala Pro Cys Lys Ile Pro Phe
```

```
                  50                    55                    60
tcc aca gag gat gga caa ggg aaa gct cac aat ggt aga ctg atc aca        240
Ser Thr Glu Asp Gly Gln Gly Lys Ala His Asn Gly Arg Leu Ile Thr
 65                  70                  75                  80 gcc aac cca gtg gtg acc aag aag gag gag cct gtc aac att gag gct        288
Ala Asn Pro Val Val Thr Lys Lys Glu Glu Pro Val Asn Ile Glu Ala
                     85                  90                  95 gaa cct cct ttt ggg gaa agt aac ata gtg att gga att gga gac aaa        336
Glu Pro Pro Phe Gly Glu Ser Asn Ile Val Ile Gly Ile Gly Asp Lys
                100                 105                 110 gcc ttg aaa att aac tgg tac aag aag gga agc tcg att ggg aag atg        384
Ala Leu Lys Ile Asn Trp Tyr Lys Lys Gly Ser Ser Ile Gly Lys Met
            115                 120                 125 ttc gag gcc act gcc ggt ggt tct ggt ggt aag gga atg tca tac acg        432
Phe Glu Ala Thr Ala Gly Gly Ser Gly Gly Lys Gly Met Ser Tyr Thr
130                 135                 140 atg tgc tca gga aag ttc tca att gat aaa gag atg gca gaa aca cag        480
Met Cys Ser Gly Lys Phe Ser Ile Asp Lys Glu Met Ala Glu Thr Gln
145                 150                 155                 160 cat ggg aca aca gtg gtg aaa gtc aag tat gag ggt gct gga gct cca        528
His Gly Thr Thr Val Val Lys Val Lys Tyr Glu Gly Ala Gly Ala Pro
                165                 170                 175 tgt aaa gtt ccc ata gag ata aga gat gtg aac aag gaa aaa gtg gtt        576
Cys Lys Val Pro Ile Glu Ile Arg Asp Val Asn Lys Glu Lys Val Val
            180                 185                 190 ggg cgt atc atc tca tct acc cct ttt gct gag aat acc aac agt gtg        624
Gly Arg Ile Ile Ser Ser Thr Pro Phe Ala Glu Asn Thr Asn Ser Val
        195                 200                 205 acc aat ata gaa ttg gaa ccc cct ttt ggg gat agc tac ata gta ata        672
Thr Asn Ile Glu Leu Glu Pro Pro Phe Gly Asp Ser Tyr Ile Val Ile
210                 215                 220 ggt gta gga gac agt gca tta aca ctc cat tgg ttc agg aaa ggg agc        720
Gly Val Gly Asp Ser Ala Leu Thr Leu His Trp Phe Arg Lys Gly Ser
225                 230                 235                 240 tcc att ggc aag atg ttt gag tcc aca tac agc ggc cgc gtg gag act        768
Ser Ile Gly Lys Met Phe Glu Ser Thr Tyr Ser Gly Arg Val Glu Thr
                245                 250                 255 tgg gct ttg aga cac cca tagtaagcgc gc                                  798
Trp Ala Leu Arg His Pro
            260

<210> SEQ ID NO 12
<211> LENGTH: 132
<212> TYPE: PRT
<213> ORGANISM: Artificial Sequence
<220> FEATURE:
<223> OTHER INFORMATION: Description of Artificial Sequence: Synthetic
      fusion sequence comprising domain(s) of Flaviviridae
      strains

<400> SEQUENCE: 12

Arg Thr Met Leu Leu Ser Val Pro Leu Leu Leu Gly Leu Leu Gly Leu
1               5                   10                  15

Ala Val Ala Arg Ser Lys Gly Met Ser Tyr Val Met Cys Thr Gly Ser
            20                  25                  30

Phe Lys Leu Glu Lys Glu Val Ala Glu Thr Gln His Gly Thr Val Leu
        35                  40                  45

Val Gln Val Lys Tyr Glu Gly Thr Asp Ala Pro Cys Lys Ile Pro Phe
    50                  55                  60

Ser Thr Gln Asp Glu Lys Gly Val Thr Gln Asn Gly Arg Leu Ile Thr
```

```
                65                  70                  75                  80
Ala Asn Pro Ile Val Thr Asp Lys Glu Lys Pro Val Asn Ile Glu Thr
                    85                  90                  95

Glu Pro Pro Phe Gly Glu Ser Tyr Ile Ile Val Gly Ala Gly Glu Lys
                100                 105                 110

Ala Leu Lys Leu Ser Trp Phe Lys Arg Gly Arg Ile Glu Thr Trp Ile
            115                 120                 125

Leu Arg His Pro
        130

<210> SEQ ID NO 13
<211> LENGTH: 408
<212> TYPE: DNA
<213> ORGANISM: Artificial Sequence
<220> FEATURE:
<223> OTHER INFORMATION: Description of Artificial Sequence: Synthetic
      fusion sequence comprising domain(s) of Flaviviridae
      strains
<220> FEATURE:
<221> NAME/KEY: CDS
<222> LOCATION: (1)..(396)

<400> SEQUENCE: 13 cgt acg atg ctg cta tcc gtg ccg ttg ctg ctc ggc ctc ctc ggc ctg      48
Arg Thr Met Leu Leu Ser Val Pro Leu Leu Leu Gly Leu Leu Gly Leu
1               5                   10                  15 gcc gtc gcc aga tct aaa ggg atg tca tat gtg atg tgc aca ggc tca      96
Ala Val Ala Arg Ser Lys Gly Met Ser Tyr Val Met Cys Thr Gly Ser
            20                  25                  30 ttt aag cta gag aag gaa gtg gct gag acc cag cat ggg act gtc cta     144
Phe Lys Leu Glu Lys Glu Val Ala Glu Thr Gln His Gly Thr Val Leu
        35                  40                  45 gtg cag gtt aaa tac gaa gga aca gat gcg cca tgc aag atc ccc ttt     192
Val Gln Val Lys Tyr Glu Gly Thr Asp Ala Pro Cys Lys Ile Pro Phe
    50                  55                  60 tcg acc caa gat gag aaa gga gtg acc cag aat ggg aga ttg ata aca     240
Ser Thr Gln Asp Glu Lys Gly Val Thr Gln Asn Gly Arg Leu Ile Thr
65                  70                  75                  80 gcc aat ccc ata gtt act gac aaa gaa aaa cca gtc aac att gag aca     288
Ala Asn Pro Ile Val Thr Asp Lys Glu Lys Pro Val Asn Ile Glu Thr
                    85                  90                  95 gaa cca cct ttt ggt gag agc tac atc ata gta ggg gca ggt gaa aaa     336
Glu Pro Pro Phe Gly Glu Ser Tyr Ile Ile Val Gly Ala Gly Glu Lys
                100                 105                 110 gct ttg aaa cta agc tgg ttc aag cgc ggc cgc att gaa acc tgg atc     384
Ala Leu Lys Leu Ser Trp Phe Lys Arg Gly Arg Ile Glu Thr Trp Ile
            115                 120                 125 ttg aga cat cca tagtaagcgc gc                                        408
Leu Arg His Pro
        130

<210> SEQ ID NO 14
<211> LENGTH: 123
<212> TYPE: PRT
<213> ORGANISM: Flavivirus sp.

<400> SEQUENCE: 14

Arg Thr Met Leu Leu Ser Val Pro Leu Leu Leu Gly Leu Leu Gly Leu
1               5                   10                  15

Ala Val Ala Arg Ser Lys Gly Thr Thr Tyr Gly Met Cys Thr Glu Lys
            20                  25                  30
```

```
Phe Ser Phe Ala Lys Asn Pro Ala Asp Thr Gly His Gly Thr Val Val
         35                  40                  45

Ile Glu Leu Ser Tyr Ser Gly Ser Asp Gly Pro Cys Lys Ile Pro Ile
 50                  55                  60

Val Ser Val Ala Ser Leu Asn Asp Met Thr Pro Val Gly Arg Leu Val
 65                  70                  75                  80

Thr Val Asn Pro Phe Val Ala Thr Ser Ser Ala Asn Ser Lys Val Leu
                 85                  90                  95

Val Glu Met Glu Pro Pro Phe Gly Asp Ser Tyr Ile Val Val Gly Arg
            100                 105                 110

Gly Asp Lys Gln Ile Asn His His Trp His Lys
            115                 120
```

<210> SEQ ID NO 15
<211> LENGTH: 390
<212> TYPE: DNA
<213> ORGANISM: Flavivirus sp.
<220> FEATURE:
<221> NAME/KEY: CDS
<222> LOCATION: (1)..(369)

<400> SEQUENCE: 15

```
cgt acg atg ctg cta tcc gtg ccg ttg ctg ctc ggc ctc ctc ggc ctg    48
Arg Thr Met Leu Leu Ser Val Pro Leu Leu Leu Gly Leu Leu Gly Leu
 1               5                  10                  15 gcc gtc gcc aga tct aaa ggc aca acc tat ggc atg tgc aca gaa aaa    96
Ala Val Ala Arg Ser Lys Gly Thr Thr Tyr Gly Met Cys Thr Glu Lys
            20                  25                  30 ttc tcg ttc gcg aaa aat ccg gcg gac act ggt cac gga aca gtt gtc   144
Phe Ser Phe Ala Lys Asn Pro Ala Asp Thr Gly His Gly Thr Val Val
         35                  40                  45 att gaa ctt tcc tac tct ggg agt gat ggc cct tgc aaa att ccg att   192
Ile Glu Leu Ser Tyr Ser Gly Ser Asp Gly Pro Cys Lys Ile Pro Ile
 50                  55                  60 gtc tcc gtt gcg agc ctc aat gac atg acc ccc gtc ggg cgg ctg gtg   240
Val Ser Val Ala Ser Leu Asn Asp Met Thr Pro Val Gly Arg Leu Val
 65                  70                  75                  80 aca gtg aac ccc ttc gtc gcg act tcc agc gcc aac tca aag gtg cta   288
Thr Val Asn Pro Phe Val Ala Thr Ser Ser Ala Asn Ser Lys Val Leu
                 85                  90                  95 gtc gag atg gaa ccc ccc ttc gga gac tcc tac atc gta gtt gga agg   336
Val Glu Met Glu Pro Pro Phe Gly Asp Ser Tyr Ile Val Val Gly Arg
            100                 105                 110 gga gac aag cag atc aac cac cat tgg cac aaa tagcggccgc tataagcgcg   389
Gly Asp Lys Gln Ile Asn His His Trp His Lys
            115                 120 c                                                                  390
```

<210> SEQ ID NO 16
<211> LENGTH: 494
<212> TYPE: PRT
<213> ORGANISM: Artificial Sequence
<220> FEATURE:
<223> OTHER INFORMATION: Description of Artificial Sequence: Synthetic
      fusion sequence comprising domain(s) of Flaviviridae
      strains

<400> SEQUENCE: 16

```
Arg Thr Met Leu Leu Ser Val Pro Leu Leu Leu Gly Leu Leu Gly Leu
 1               5                  10                  15

Ala Val Ala Arg Ser Lys Gly Met Ser Tyr Val Met Cys Thr Gly Ser
            20                  25                  30
```

```
                20                  25                  30
Phe Lys Leu Glu Lys Glu Val Ala Glu Thr Gln His Gly Thr Val Leu
         35                  40                  45
Val Gln Val Lys Tyr Glu Gly Thr Asp Ala Pro Cys Lys Ile Pro Phe
 50                  55                  60
Ser Thr Gln Asp Glu Lys Gly Val Thr Gln Asn Gly Arg Leu Ile Thr
 65                  70                  75                  80
Ala Asn Pro Ile Val Thr Asp Lys Glu Lys Pro Val Asn Ile Glu Thr
                 85                  90                  95
Glu Pro Pro Phe Gly Glu Ser Tyr Ile Ile Val Gly Ala Gly Glu Lys
                100                 105                 110
Ala Leu Lys Leu Ser Trp Phe Lys Lys Gly Ser Ser Ile Gly Lys Met
            115                 120                 125
Phe Glu Ala Thr Ala Gly Ser Gly Gly Lys Gly Met Ser Tyr Ser
            130                 135                 140
Met Cys Thr Gly Lys Phe Lys Ile Val Lys Glu Ile Ala Glu Thr Gln
145                 150                 155                 160
His Gly Thr Ile Val Ile Arg Val Gln Tyr Glu Gly Asp Gly Ser Pro
                165                 170                 175
Cys Lys Ile Pro Phe Glu Ile Met Asp Leu Glu Lys Arg His Val Leu
            180                 185                 190
Gly Arg Leu Ile Thr Val Asn Pro Ile Val Thr Glu Lys Asp Ser Pro
            195                 200                 205
Val Asn Ile Glu Ala Glu Pro Pro Phe Gly Asp Ser Tyr Ile Ile Ile
            210                 215                 220
Gly Val Glu Pro Gly Gln Leu Lys Leu Asn Trp Phe Lys Lys Gly Ser
225                 230                 235                 240
Ser Ile Gly Gln Met Phe Glu Thr Thr Met Gly Gly Ser Lys Gly Met
                245                 250                 255
Ser Tyr Ala Met Cys Leu Asn Thr Phe Val Leu Lys Lys Glu Val Ser
            260                 265                 270
Glu Thr Gln His Gly Thr Ile Leu Ile Lys Val Glu Tyr Lys Gly Glu
            275                 280                 285
Asp Ala Pro Cys Lys Ile Pro Phe Ser Thr Glu Asp Gly Gln Gly Lys
            290                 295                 300
Ala His Asn Gly Arg Leu Ile Thr Ala Asn Pro Val Val Thr Lys Lys
305                 310                 315                 320
Glu Glu Pro Val Asn Ile Glu Ala Glu Pro Pro Phe Gly Glu Ser Asn
                325                 330                 335
Ile Val Ile Gly Ile Gly Asp Lys Ala Leu Lys Ile Asn Trp Tyr Lys
            340                 345                 350
Lys Gly Ser Ser Ile Gly Lys Met Phe Glu Ala Thr Ala Gly Gly Ser
            355                 360                 365
Gly Gly Lys Gly Met Ser Tyr Thr Met Cys Ser Gly Lys Phe Ser Ile
            370                 375                 380
Asp Lys Glu Met Ala Glu Thr Gln His Gly Thr Thr Val Val Lys Val
385                 390                 395                 400
Lys Tyr Glu Gly Ala Gly Ala Pro Cys Lys Val Pro Ile Glu Ile Arg
                405                 410                 415
Asp Val Asn Lys Glu Lys Val Val Gly Arg Ile Ile Ser Ser Thr Pro
            420                 425                 430
Phe Ala Glu Asn Thr Asn Ser Val Thr Asn Ile Glu Leu Glu Pro Pro
            435                 440                 445
```

```
Phe Gly Asp Ser Tyr Ile Val Ile Gly Val Gly Asp Ser Ala Leu Thr
    450                 455                 460

Leu His Trp Phe Arg Lys Gly Ser Ser Ile Gly Lys Met Phe Glu Ser
465                 470                 475                 480

Thr Tyr Ser Gly Arg Val Glu Thr Trp Ala Leu Arg His Pro
                485                 490

<210> SEQ ID NO 17
<211> LENGTH: 1494
<212> TYPE: DNA
<213> ORGANISM: Artificial Sequence
<220> FEATURE:
<223> OTHER INFORMATION: Description of Artificial Sequence: Synthetic
      fusion sequence comprising domain(s) of Flaviviridae
      strains
<220> FEATURE:
<221> NAME/KEY: CDS
<222> LOCATION: (1)..(1482)

<400> SEQUENCE: 17 cgt acg atg ctg cta tcc gtg ccg ttg ctg ctc ggc ctc ctc ggc ctg      48
Arg Thr Met Leu Leu Ser Val Pro Leu Leu Leu Gly Leu Leu Gly Leu
1               5                   10                  15 gcc gtc gcc aga tct aaa ggg atg tca tat gtg atg tgc aca ggc tca      96
Ala Val Ala Arg Ser Lys Gly Met Ser Tyr Val Met Cys Thr Gly Ser
            20                  25                  30 ttt aag cta gag aag gaa gtg gct gag acc cag cat ggg act gtc cta     144
Phe Lys Leu Glu Lys Glu Val Ala Glu Thr Gln His Gly Thr Val Leu
        35                  40                  45 gtg cag gtt aaa tac gaa gga aca gat gcg cca tgc aag atc ccc ttt     192
Val Gln Val Lys Tyr Glu Gly Thr Asp Ala Pro Cys Lys Ile Pro Phe
    50                  55                  60 tcg acc caa gat gag aaa gga gtg acc cag aat ggg aga ttg ata aca     240
Ser Thr Gln Asp Glu Lys Gly Val Thr Gln Asn Gly Arg Leu Ile Thr
65                  70                  75                  80 gcc aat ccc ata gtt act gac aaa gaa aaa cca gtc aac att gag aca     288
Ala Asn Pro Ile Val Thr Asp Lys Glu Lys Pro Val Asn Ile Glu Thr
                85                  90                  95 gaa cca cct ttt ggt gag agc tac atc ata gta ggg gca ggt gaa aaa     336
Glu Pro Pro Phe Gly Glu Ser Tyr Ile Ile Val Gly Ala Gly Glu Lys
            100                 105                 110 gct ttg aaa cta agc tgg ttc aag aaa gga agc agc ata ggg aaa atg     384
Ala Leu Lys Leu Ser Trp Phe Lys Lys Gly Ser Ser Ile Gly Lys Met
        115                 120                 125 ttc gaa gca acc gcc gga gga tca gga ggg aaa gga atg tca tac tct     432
Phe Glu Ala Thr Ala Gly Gly Ser Gly Gly Lys Gly Met Ser Tyr Ser
    130                 135                 140 atg tgt aca gga aag ttt aaa att gtg aag gaa ata gca gaa aca caa     480
Met Cys Thr Gly Lys Phe Lys Ile Val Lys Glu Ile Ala Glu Thr Gln
145                 150                 155                 160 cat gga aca ata gtt atc aga gta caa tat gaa ggg gac ggc tct cca     528
His Gly Thr Ile Val Ile Arg Val Gln Tyr Glu Gly Asp Gly Ser Pro
                165                 170                 175 tgt aag atc cct ttt gag ata atg gat ttg gaa aaa aga cac gtc tta     576
Cys Lys Ile Pro Phe Glu Ile Met Asp Leu Glu Lys Arg His Val Leu
            180                 185                 190 ggt cgc ctg att aca gtt aac ccg atc gta aca gaa aaa gat agc cca     624
Gly Arg Leu Ile Thr Val Asn Pro Ile Val Thr Glu Lys Asp Ser Pro
        195                 200                 205 gtc aac ata gaa gca gaa cct cca ttc gga gac agc tac atc atc ata     672
Val Asn Ile Glu Ala Glu Pro Pro Phe Gly Asp Ser Tyr Ile Ile Ile
```

```
                    210                 215                 220
gga gta gag ccg gga caa ttg aaa ctc aac tgg ttt aag aaa gga agt        720
Gly Val Glu Pro Gly Gln Leu Lys Leu Asn Trp Phe Lys Lys Gly Ser
225                 230                 235                 240 tcc atc ggc caa atg ttt gag aca aca atg gga gga tct aag ggg atg        768
Ser Ile Gly Gln Met Phe Glu Thr Thr Met Gly Gly Ser Lys Gly Met
                245                 250                 255 agc tat gca atg tgc ttg aat acc ttt gtg ttg aag aaa gaa gtc tcc        816
Ser Tyr Ala Met Cys Leu Asn Thr Phe Val Leu Lys Lys Glu Val Ser
            260                 265                 270 gaa acg cag cat ggg aca ata ctc att aag gtt gag tac aaa ggg gaa        864
Glu Thr Gln His Gly Thr Ile Leu Ile Lys Val Glu Tyr Lys Gly Glu
        275                 280                 285 gat gca cct tgc aag att cct ttc tcc aca gag gat gga caa ggg aaa        912
Asp Ala Pro Cys Lys Ile Pro Phe Ser Thr Glu Asp Gly Gln Gly Lys
    290                 295                 300 gct cac aat ggt aga ctg atc aca gcc aac cca gtg gtg acc aag aag        960
Ala His Asn Gly Arg Leu Ile Thr Ala Asn Pro Val Val Thr Lys Lys
305                 310                 315                 320 gag gag cct gtc aac att gag gct gaa cct cct ttt ggg gaa agt aac       1008
Glu Glu Pro Val Asn Ile Glu Ala Glu Pro Pro Phe Gly Glu Ser Asn
                325                 330                 335 ata gtg att gga att gga gac aaa gcc ttg aaa att aac tgg tac aag       1056
Ile Val Ile Gly Ile Gly Asp Lys Ala Leu Lys Ile Asn Trp Tyr Lys
            340                 345                 350 aag gga agc tcg att ggg aag atg ttc gag gcc act gcc ggt ggt tct       1104
Lys Gly Ser Ser Ile Gly Lys Met Phe Glu Ala Thr Ala Gly Gly Ser
        355                 360                 365 ggt ggt aag gga atg tca tac acg atg tgc tca gga aag ttc tca att       1152
Gly Gly Lys Gly Met Ser Tyr Thr Met Cys Ser Gly Lys Phe Ser Ile
    370                 375                 380 gat aaa gag atg gca gaa aca cag cat ggg aca aca gtg gtg aaa gtc       1200
Asp Lys Glu Met Ala Glu Thr Gln His Gly Thr Thr Val Val Lys Val
385                 390                 395                 400 aag tat gag ggt gct gga gct cca tgt aaa gtt ccc ata gag ata aga       1248
Lys Tyr Glu Gly Ala Gly Ala Pro Cys Lys Val Pro Ile Glu Ile Arg
                405                 410                 415 gat gtg aac aag gaa aaa gtg gtt ggg cgt atc atc tca tct acc cct       1296
Asp Val Asn Lys Glu Lys Val Val Gly Arg Ile Ile Ser Ser Thr Pro
            420                 425                 430 ttt gct gag aat acc aac agt gtg acc aat ata gaa ttg gaa ccc cct       1344
Phe Ala Glu Asn Thr Asn Ser Val Thr Asn Ile Glu Leu Glu Pro Pro
        435                 440                 445 ttt ggg gat agc tac ata gta ata ggt gta gga gac agt gca tta aca       1392
Phe Gly Asp Ser Tyr Ile Val Ile Gly Val Gly Asp Ser Ala Leu Thr
    450                 455                 460 ctc cat tgg ttc agg aaa ggg agc tcc att ggc aag atg ttt gag tcc       1440
Leu His Trp Phe Arg Lys Gly Ser Ser Ile Gly Lys Met Phe Glu Ser
465                 470                 475                 480 aca tac agc ggc cgc gtg gag act tgg gct ttg aga cac cca                1482
Thr Tyr Ser Gly Arg Val Glu Thr Trp Ala Leu Arg His Pro
                485                 490 tagtaagcgc gc                                                          1494

<210> SEQ ID NO 18
<211> LENGTH: 390
<212> TYPE: DNA
<213> ORGANISM: Flavivirus sp.

<400> SEQUENCE: 18
```

```
cgtacgatgc tgctatccgt gccgttgctg ctcggcctcc tcggcctggc cgtcgccaga    60
tctaagggaa caacctatgg cgtctgttca aaggctttca g

```
Met Ser Ser Glu Gly Ala Trp Lys Gln Ile Gln Lys Val Glu Thr Trp
145                 150                 155                 160

Ala Leu Arg His Pro Arg Arg Asp Lys Arg Asp Lys Leu Gln Leu Lys
                165                 170                 175

Gly Met Ser Tyr Ser Met Cys Thr Gly Lys Phe Lys Ile Val Lys Glu
            180                 185                 190

Ile Ala Glu Thr Gln His Gly Thr Ile Val Ile Arg Val Gln Tyr Glu
        195                 200                 205

Gly Asp Gly Ser Pro Cys Lys Ile Pro Phe Glu Ile Thr Asp Leu Glu
    210                 215                 220

Lys Arg His Val Leu Gly Arg Leu Ile Thr Val Asn Pro Ile Val Thr
225                 230                 235                 240

Glu Lys Asp Ser Pro Val Asn Ile Glu Ala Glu Pro Pro Phe Gly Asp
                245                 250                 255

Ser Tyr Ile Ile Val Gly Val Glu Pro Gly Gln Leu Lys Leu Asn Trp
            260                 265                 270

Phe Arg Arg Asp Lys Arg Ser Val Ala Leu Ala Pro His Val Gly Leu
        275                 280                 285

Gly Leu Glu Thr Arg Thr Glu Thr Trp Met Ser Ser Glu Gly Ala Trp
    290                 295                 300

Lys Gln Ile Gln Lys Val Glu Thr Trp Ala Leu Arg His Pro Arg Arg
305                 310                 315                 320

Asp Lys Arg Asp Lys Leu Lys Leu Lys Gly Met Ser Tyr Ala Met Cys
                325                 330                 335

Leu Asn Thr Phe Val Leu Lys Lys Glu Val Ser Glu Thr Gln His Gly
            340                 345                 350

Thr Ile Leu Ile Lys Val Glu Tyr Lys Gly Glu Asp Ala Pro Cys Lys
        355                 360                 365

Ile Pro Phe Ser Thr Glu Asp Gly Gln Gly Lys Ala His Asn Gly Arg
    370                 375                 380

Leu Ile Thr Ala Asn Pro Val Val Thr Lys Lys Glu Glu Pro Val Asn
385                 390                 395                 400

Ile Glu Ala Glu Pro Pro Phe Gly Glu Ser Asn Ile Val Ile Gly Ile
                405                 410                 415

Gly Asp Lys Ala Leu Lys Ile Asn Trp Tyr Arg Arg Asp Lys Arg Ser
            420                 425                 430

Val Ala Leu Ala Pro His Val Gly Leu Gly Leu Glu Thr Arg Thr Glu
        435                 440                 445

Thr Trp Met Ser Ser Glu Gly Ala Trp Lys Gln Ile Gln Lys Val Glu
    450                 455                 460

Thr Trp Ala Leu Arg His Pro Arg Arg Asp Lys Arg Glu Lys Leu Arg
465                 470                 475                 480

Ile Lys Gly Met Ser Tyr Thr Met Cys Ser Gly Lys Phe Ser Ile Asp
                485                 490                 495

Lys Glu Met Ala Glu Thr Gln His Gly Thr Thr Val Val Lys Val Lys
            500                 505                 510

Tyr Glu Gly Ala Gly Ala Pro Cys Lys Val Pro Ile Glu Ile Arg Asp
        515                 520                 525

Val Asn Lys Glu Lys Val Val Gly Arg Ile Ile Ser Ser Thr Pro Leu
    530                 535                 540

Ala Glu Asn Thr Asn Ser Val Thr Asn Ile Glu Leu Glu Pro Pro Phe
545                 550                 555                 560
```

-continued

```
Gly Asp Ser Tyr Ile Val Ile Gly Val Gly Asn Ser Ala Leu Thr Leu
                565                 570                 575

His Trp Phe Arg Arg Asp Lys Arg Ser Val Ala Leu Ala Pro His Val
            580                 585                 590

Gly Leu Gly Leu Glu Thr Arg Thr Glu Thr Trp Met Ser Ser Glu Gly
        595                 600                 605

Ala Trp Lys Gln Ile Gln Lys Val Glu Thr Trp Ala Leu Arg His Pro
610                 615                 620

<210> SEQ ID NO 21
<211> LENGTH: 609
<212> TYPE: PRT
<213> ORGANISM: Artificial Sequence
<220> FEATURE:
<223> OTHER INFORMATION: Description of Artificial Sequence: Synthetic
      fusion sequence comprising domain(s) of Flaviviridae
      strains

<400> SEQUENCE: 21

Met Leu Leu Ser Val Pro Leu Leu Gly Leu Leu Gly Leu Ala Val
1               5                   10                  15

Ala Asp Lys Leu Thr Leu Lys Gly Met Ser Tyr Val Met Cys Thr Gly
                20                  25                  30

Ser Phe Lys Leu Glu Lys Glu Val Ala Glu Thr Gln His Gly Thr Val
            35                  40                  45

Leu Val Gln Val Lys Tyr Glu Gly Thr Asp Ala Pro Cys Lys Ile Pro
        50                  55                  60

Phe Ser Thr Gln Asp Glu Lys Gly Val Thr Gln Asn Gly Arg Leu Ile
65                  70                  75                  80

Thr Ala Asn Pro Ile Val Thr Asp Lys Glu Lys Pro Val Asn Ile Glu
                85                  90                  95

Thr Glu Pro Pro Phe Gly Glu Ser Tyr Ile Ile Val Gly Ala Gly Glu
            100                 105                 110

Lys Ala Leu Lys Leu Ser Trp Phe Ser Val Ala Leu Ala Pro His Val
        115                 120                 125

Gly Leu Gly Leu Glu Thr Arg Thr Glu Thr Trp Met Ser Ser Glu Gly
    130                 135                 140

Ala Trp Lys Gln Ile Gln Lys Val Glu Thr Trp Ala Leu Arg His Pro
145                 150                 155                 160

Arg Arg Asp Lys Arg Asp Lys Leu Gln Leu Lys Gly Met Ser Tyr Ser
                165                 170                 175

Met Cys Thr Gly Lys Phe Lys Ile Val Lys Glu Ile Ala Glu Thr Gln
            180                 185                 190

His Gly Thr Ile Val Ile Arg Val Gln Tyr Glu Gly Asp Gly Ser Pro
        195                 200                 205

Cys Lys Ile Pro Phe Glu Ile Thr Asp Leu Glu Lys Arg His Val Leu
    210                 215                 220

Gly Arg Leu Ile Thr Val Asn Pro Ile Val Thr Glu Lys Asp Ser Pro
225                 230                 235                 240

Val Asn Ile Glu Ala Glu Pro Pro Phe Gly Asp Ser Tyr Ile Ile Val
                245                 250                 255

Gly Val Glu Pro Gly Gln Leu Lys Leu Asn Trp Phe Ser Val Ala Leu
            260                 265                 270

Ala Pro His Val Gly Leu Gly Leu Glu Thr Arg Thr Glu Thr Trp Met
        275                 280                 285

Ser Ser Glu Gly Ala Trp Lys Gln Ile Gln Lys Val Glu Thr Trp Ala
```

```
            290                 295                 300
Leu Arg His Pro Arg Arg Asp Lys Arg Asp Lys Leu Lys Leu Lys Gly
305                 310                 315                 320

Met Ser Tyr Ala Met Cys Leu Asn Thr Phe Val Leu Lys Lys Glu Val
                325                 330                 335

Ser Glu Thr Gln His Gly Thr Ile Leu Ile Lys Val Glu Tyr Lys Gly
            340                 345                 350

Glu Asp Ala Pro Cys Lys Ile Pro Phe Ser Thr Glu Asp Gly Gln Gly
        355                 360                 365

Lys Ala His Asn Gly Arg Leu Ile Thr Ala Asn Pro Val Val Thr Lys
    370                 375                 380

Lys Glu Glu Pro Val Asn Ile Glu Ala Glu Pro Pro Phe Gly Glu Ser
385                 390                 395                 400

Asn Ile Val Ile Gly Ile Gly Asp Lys Ala Leu Lys Ile Asn Trp Tyr
                405                 410                 415

Ser Val Ala Leu Ala Pro His Val Gly Leu Gly Leu Glu Thr Arg Thr
            420                 425                 430

Glu Thr Trp Met Ser Ser Glu Gly Ala Trp Lys Gln Ile Gln Lys Val
        435                 440                 445

Glu Thr Trp Ala Leu Arg His Pro Arg Arg Asp Lys Arg Glu Lys Leu
    450                 455                 460

Arg Ile Lys Gly Met Ser Tyr Thr Met Cys Ser Gly Lys Phe Ser Ile
465                 470                 475                 480

Asp Lys Glu Met Ala Glu Thr Gln His Gly Thr Thr Val Val Lys Val
                485                 490                 495

Lys Tyr Glu Gly Ala Gly Ala Pro Cys Lys Val Pro Ile Glu Ile Arg
            500                 505                 510

Asp Val Asn Lys Glu Lys Val Val Gly Arg Ile Ile Ser Ser Thr Pro
        515                 520                 525

Leu Ala Glu Asn Thr Asn Ser Val Thr Asn Ile Glu Leu Glu Pro Pro
    530                 535                 540

Phe Gly Asp Ser Tyr Ile Val Ile Gly Val Gly Asn Ser Ala Leu Thr
545                 550                 555                 560

Leu His Trp Phe Arg Arg Asp Lys Arg Ser Val Ala Leu Ala Pro His
                565                 570                 575

Val Gly Leu Gly Leu Glu Thr Arg Thr Glu Thr Trp Met Ser Ser Glu
            580                 585                 590

Gly Ala Trp Lys Gln Ile Gln Lys Val Glu Thr Trp Ala Leu Arg His
        595                 600                 605

Pro

<210> SEQ ID NO 22
<211> LENGTH: 624
<212> TYPE: PRT
<213> ORGANISM: Artificial Sequence
<220> FEATURE:
<223> OTHER INFORMATION: Description of Artificial Sequence: Synthetic
      fusion sequence comprising domain(s) of Flaviviridae
      strains

<400> SEQUENCE: 22

Met Leu Leu Ser Val Pro Leu Leu Gly Leu Leu Gly Leu Ala Val
1               5                   10                  15

Ala Asp Lys Leu Thr Leu Lys Gly Met Ser Tyr Val Met Cys Thr Gly
            20                  25                  30
```

```
Ser Phe Lys Leu Glu Lys Glu Val Ala Glu Thr Gln His Gly Thr Val
     35                  40                  45

Leu Val Gln Val Lys Tyr Glu Gly Thr Asp Ala Pro Cys Lys Ile Pro
 50                  55                  60

Phe Ser Thr Gln Asp Glu Lys Gly Val Thr Gln Asn Gly Arg Leu Ile
 65                  70                  75                  80

Thr Ala Asn Pro Ile Val Thr Asp Lys Glu Lys Pro Val Asn Ile Glu
                 85                  90                  95

Thr Glu Pro Pro Phe Gly Glu Ser Tyr Ile Ile Val Gly Ala Gly Glu
             100                 105                 110

Lys Ala Leu Lys Leu Ser Trp Phe Arg Arg Asp Lys Arg Ser Val Ala
         115                 120                 125

Leu Ala Pro His Val Gly Leu Gly Leu Glu Thr Arg Thr Glu Thr Trp
 130                 135                 140

Met Ser Ser Glu Gly Ala Trp Lys Gln Ile Gln Lys Val Glu Thr Trp
145                 150                 155                 160

Ala Leu Arg His Pro Arg Arg Asp Lys Arg Asp Lys Leu Gln Leu Lys
                165                 170                 175

Gly Met Ser Tyr Ser Met Cys Thr Gly Lys Phe Lys Ile Val Lys Glu
            180                 185                 190

Ile Ala Glu Thr Gln His Gly Thr Ile Val Ile Arg Val Gln Tyr Glu
        195                 200                 205

Gly Asp Gly Ser Pro Cys Lys Ile Pro Phe Glu Ile Thr Asp Leu Glu
    210                 215                 220

Lys Arg His Val Leu Gly Arg Leu Ile Thr Val Asn Pro Ile Val Thr
225                 230                 235                 240

Glu Lys Asp Ser Pro Val Asn Ile Glu Ala Glu Pro Pro Phe Gly Asp
                245                 250                 255

Ser Tyr Ile Ile Val Gly Val Glu Pro Gly Gln Leu Lys Leu Asn Trp
            260                 265                 270

Phe Arg Arg Glu Lys Arg Ser Val Ala Leu Val Pro His Val Gly Met
        275                 280                 285

Gly Leu Glu Thr Arg Thr Glu Thr Trp Met Ser Ser Glu Gly Ala Trp
    290                 295                 300

Lys His Val Gln Arg Ile Glu Thr Trp Ile Leu Arg His Pro Arg Arg
305                 310                 315                 320

Asp Lys Arg Asp Lys Leu Lys Leu Lys Gly Met Ser Tyr Ala Met Cys
                325                 330                 335

Leu Asn Thr Phe Val Leu Lys Lys Glu Val Ser Glu Thr Gln His Gly
            340                 345                 350

Thr Ile Leu Ile Lys Val Glu Tyr Lys Gly Glu Asp Ala Pro Cys Lys
        355                 360                 365

Ile Pro Phe Ser Thr Glu Asp Gly Gln Gly Lys Ala His Asn Gly Arg
    370                 375                 380

Leu Ile Thr Ala Asn Pro Val Val Thr Lys Lys Glu Glu Pro Val Asn
385                 390                 395                 400

Ile Glu Ala Glu Pro Pro Phe Gly Glu Ser Asn Ile Val Ile Gly Ile
                405                 410                 415

Gly Asp Lys Ala Leu Lys Ile Asn Trp Tyr Arg Arg Asp Lys Arg Ser
            420                 425                 430

Val Ala Leu Ala Pro His Val Gly Met Gly Leu Asp Thr Arg Thr Gln
        435                 440                 445

Thr Trp Met Ser Ala Glu Gly Ala Trp Arg Gln Val Glu Lys Val Glu
```

```
                  450                 455                 460
Thr Trp Ala Leu Arg His Pro Arg Arg Asp Lys Arg Glu Lys Leu Arg
465                 470                 475                 480

Ile Lys Gly Met Ser Tyr Thr Met Cys Ser Gly Lys Phe Ser Ile Asp
                485                 490                 495

Lys Glu Met Ala Glu Thr Gln His Gly Thr Thr Val Val Lys Val Lys
                500                 505                 510

Tyr Glu Gly Ala Gly Ala Pro Cys Lys Val Pro Ile Glu Ile Arg Asp
                515                 520                 525

Val Asn Lys Glu Lys Val Val Gly Arg Ile Ile Ser Ser Thr Pro Leu
530                 535                 540

Ala Glu Asn Thr Asn Ser Val Thr Asn Ile Glu Leu Glu Pro Pro Phe
545                 550                 555                 560

Gly Asp Ser Tyr Ile Val Ile Gly Val Gly Asn Ser Ala Leu Thr Leu
                565                 570                 575

His Trp Phe Arg Arg Glu Lys Arg Ser Val Ala Leu Thr Pro His Ser
                580                 585                 590

Gly Met Gly Leu Glu Thr Arg Ala Glu Thr Trp Met Ser Ser Glu Gly
                595                 600                 605

Ala Trp Lys His Ala Gln Arg Val Glu Ser Trp Ile Leu Arg Asn Pro
610                 615                 620

<210> SEQ ID NO 23
<211> LENGTH: 489
<212> TYPE: PRT
<213> ORGANISM: Artificial Sequence
<220> FEATURE:
<223> OTHER INFORMATION: Description of Artificial Sequence: Synthetic
      fusion sequence comprising domain(s) of Flaviviridae
      strains

<400> SEQUENCE: 23

Met Leu Leu Ser Val Pro Leu Leu Leu Gly Leu Leu Gly Leu Ala Val
1               5                   10                  15

Ala Asp Lys Leu Thr Leu Lys Gly Met Ser Tyr Val Met Cys Thr Gly
                20                  25                  30

Ser Phe Lys Leu Glu Lys Glu Val Ala Glu Thr Gln His Gly Thr Val
                35                  40                  45

Leu Val Gln Val Lys Tyr Glu Gly Thr Asp Ala Pro Cys Lys Ile Pro
                50                  55                  60

Phe Ser Thr Gln Asp Glu Lys Gly Val Thr Gln Asn Gly Arg Leu Ile
65                  70                  75                  80

Thr Ala Asn Pro Ile Val Thr Asp Lys Glu Lys Pro Val Asn Ile Glu
                85                  90                  95

Thr Glu Pro Pro Phe Gly Glu Ser Tyr Ile Ile Val Gly Ala Gly Glu
                100                 105                 110

Lys Ala Leu Lys Leu Ser Trp Phe Arg Arg Asp Lys Arg Asp Lys Leu
                115                 120                 125

Gln Leu Lys Gly Met Ser Tyr Ser Met Cys Thr Gly Lys Phe Lys Ile
                130                 135                 140

Val Lys Glu Ile Ala Glu Thr Gln His Gly Thr Ile Val Ile Arg Val
145                 150                 155                 160

Gln Tyr Glu Gly Asp Gly Ser Pro Cys Lys Ile Pro Phe Glu Ile Thr
                165                 170                 175

Asp Leu Glu Lys Arg His Val Leu Gly Arg Leu Ile Thr Val Asn Pro
                180                 185                 190
```

Ile Val Thr Glu Lys Asp Ser Pro Val Asn Ile Glu Ala Glu Pro Pro
        195                 200                 205

Phe Gly Asp Ser Tyr Ile Ile Val Gly Val Glu Pro Gly Gln Leu Lys
210                 215                 220

Leu Asn Trp Phe Arg Arg Asp Lys Arg Asp Lys Leu Lys Leu Lys Gly
225                 230                 235                 240

Met Ser Tyr Ala Met Cys Leu Asn Thr Phe Val Leu Lys Lys Glu Val
                245                 250                 255

Ser Glu Thr Gln His Gly Thr Ile Leu Ile Lys Val Glu Tyr Lys Gly
                260                 265                 270

Glu Asp Ala Pro Cys Lys Ile Pro Phe Ser Thr Glu Asp Gly Gln Gly
                275                 280                 285

Lys Ala His Asn Gly Arg Leu Ile Thr Ala Asn Pro Val Val Thr Lys
                290                 295                 300

Lys Glu Glu Pro Val Asn Ile Glu Ala Glu Pro Pro Phe Gly Glu Ser
305                 310                 315                 320

Asn Ile Val Ile Gly Ile Gly Asp Lys Ala Leu Lys Ile Asn Trp Tyr
                325                 330                 335

Arg Arg Asp Lys Arg Glu Lys Leu Arg Ile Lys Gly Met Ser Tyr Thr
                340                 345                 350

Met Cys Ser Gly Lys Phe Ser Ile Asp Lys Glu Met Ala Glu Thr Gln
                355                 360                 365

His Gly Thr Thr Val Val Lys Val Lys Tyr Glu Gly Ala Gly Ala Pro
                370                 375                 380

Cys Lys Val Pro Ile Glu Ile Arg Asp Val Asn Lys Glu Lys Val Val
385                 390                 395                 400

Gly Arg Ile Ile Ser Ser Thr Pro Leu Ala Glu Asn Thr Asn Ser Val
                405                 410                 415

Thr Asn Ile Glu Leu Glu Pro Pro Phe Gly Asp Ser Tyr Ile Val Ile
                420                 425                 430

Gly Val Gly Asn Ser Ala Leu Thr Leu His Trp Phe Arg Arg Asp Lys
                435                 440                 445

Arg Ser Val Ala Leu Ala Pro His Val Gly Leu Gly Leu Glu Thr Arg
                450                 455                 460

Thr Glu Thr Trp Met Ser Ser Glu Gly Ala Trp Lys Gln Ile Gln Lys
465                 470                 475                 480

Val Glu Thr Trp Ala Leu Arg His Pro
                485

<210> SEQ ID NO 24
<211> LENGTH: 474
<212> TYPE: PRT
<213> ORGANISM: Artificial Sequence
<220> FEATURE:
<223> OTHER INFORMATION: Description of Artificial Sequence: Synthetic
      fusion sequence comprising domain(s) of Flaviviridae
      strains

<400> SEQUENCE: 24

Met Leu Leu Ser Val Pro Leu Leu Gly Leu Leu Gly Leu Ala Val
1               5                   10                  15

Ala Asp Lys Leu Thr Leu Lys Gly Met Ser Tyr Val Met Cys Thr Gly
                20                  25                  30

Ser Phe Lys Leu Glu Lys Glu Val Ala Glu Thr Gln His Gly Thr Val
                35                  40                  45

```
Leu Val Gln Val Lys Tyr Glu Gly Thr Asp Ala Pro Cys Lys Ile Pro
 50                  55                  60

Phe Ser Thr Gln Asp Glu Lys Gly Val Thr Gln Asn Gly Arg Leu Ile
 65                  70                  75                  80

Thr Ala Asn Pro Ile Val Thr Asp Lys Glu Lys Pro Val Asn Ile Glu
                 85                  90                  95

Thr Glu Pro Pro Phe Gly Glu Ser Tyr Ile Ile Val Gly Ala Gly Glu
                100                 105                 110

Lys Ala Leu Lys Leu Ser Trp Phe Asp Lys Leu Gln Leu Lys Gly Met
            115                 120                 125

Ser Tyr Ser Met Cys Thr Gly Lys Phe Lys Ile Val Lys Glu Ile Ala
130                 135                 140

Glu Thr Gln His Gly Thr Ile Val Ile Arg Val Gln Tyr Glu Gly Asp
145                 150                 155                 160

Gly Ser Pro Cys Lys Ile Pro Phe Glu Ile Thr Asp Leu Glu Lys Arg
                165                 170                 175

His Val Leu Gly Arg Leu Ile Thr Val Asn Pro Ile Val Thr Glu Lys
                180                 185                 190

Asp Ser Pro Val Asn Ile Glu Ala Glu Pro Pro Phe Gly Asp Ser Tyr
            195                 200                 205

Ile Ile Val Gly Val Glu Pro Gly Gln Leu Lys Leu Asn Trp Phe Asp
210                 215                 220

Lys Leu Lys Leu Lys Gly Met Ser Tyr Ala Met Cys Leu Asn Thr Phe
225                 230                 235                 240

Val Leu Lys Lys Glu Val Ser Glu Thr Gln His Gly Thr Ile Leu Ile
                245                 250                 255

Lys Val Glu Tyr Lys Gly Glu Asp Ala Pro Cys Lys Ile Pro Phe Ser
                260                 265                 270

Thr Glu Asp Gly Gln Gly Lys Ala His Asn Gly Arg Leu Ile Thr Ala
            275                 280                 285

Asn Pro Val Val Thr Lys Lys Glu Glu Pro Val Asn Ile Glu Ala Glu
290                 295                 300

Pro Pro Phe Gly Glu Ser Asn Ile Val Ile Gly Ile Gly Asp Lys Ala
305                 310                 315                 320

Leu Lys Ile Asn Trp Tyr Glu Lys Leu Arg Ile Lys Gly Met Ser Tyr
                325                 330                 335

Thr Met Cys Ser Gly Lys Phe Ser Ile Asp Lys Glu Met Ala Glu Thr
                340                 345                 350

Gln His Gly Thr Thr Val Val Lys Val Lys Tyr Glu Gly Ala Gly Ala
            355                 360                 365

Pro Cys Lys Val Pro Ile Glu Ile Arg Asp Val Asn Lys Glu Lys Val
370                 375                 380

Val Gly Arg Ile Ile Ser Ser Thr Pro Leu Ala Glu Asn Thr Asn Ser
385                 390                 395                 400

Val Thr Asn Ile Glu Leu Glu Pro Pro Phe Gly Asp Ser Tyr Ile Val
                405                 410                 415

Ile Gly Val Gly Asn Ser Ala Leu Thr Leu His Trp Phe Arg Arg Asp
                420                 425                 430

Lys Arg Ser Val Ala Leu Ala Pro His Val Gly Leu Gly Leu Glu Thr
            435                 440                 445

Arg Thr Glu Thr Trp Met Ser Ser Glu Gly Ala Trp Lys Gln Ile Gln
450                 455                 460

Lys Val Glu Thr Trp Ala Leu Arg His Pro
```

465            470

<210> SEQ ID NO 25
<211> LENGTH: 1890
<212> TYPE: DNA
<213> ORGANISM: Artificial Sequence
<220> FEATURE:
<223> OTHER INFORMATION: Description of Artificial Sequence: Synthetic
      fusion sequence comprising domain(s) of Flaviviridae
      strains

<400> SEQUENCE: 25

```
cgtacgatgc tcctttccgt cccgttgcta ttaggactac tcgggttggc tgtcgccgat      60
aagctgactc tgaagggaat gtcatacgtt atgtgcacag ggagcttcaa gttggagaag     120
gaggtggcag agacccagca cggaacagtc ttggtgcagg tcaagtacga gggcacggac     180
gctccttgta agatcccatt ctcaacccag gatgagaagg gcgtgaccca gaatggacgg     240
ctgatcacgg ctaatcccat cgtgactgat aaggagaagc cagtcaacat cgagacagag     300
ccacccttcg gtgagtctta cataatagtc ggggccggag agaaggctct caagctgagt     360
tggttcaggc gggataagcg aagcgtcgca cttgccccac acgttggcct cggactcgag     420
acaagaacag agacctggat gagcagcgag ggagcctgga gcagattca gaaggttgag     480
acctgggctc tccggcaccc tcgccgtgat aagagagaca gctgcagct aaggggatg      540
agttattcca tgtgcacagg caagttcaag attgtcaagg atagcagag actcagcac      600
ggaaccatag tgatcagagt tcagtacgag ggagacggat ccccatgcaa gattccgttt     660
gagattaccg acctggagaa cgccacgtg ctggggagac tcattactgt gaacccaatc     720
gtgactgaga aggattctcc cgtcaatatc gaggctgagc caccattcgg agattcttat     780
ataatcgttg gtgtagagcc tggccagtta aagttgaatt ggtttaggcg ggataagagg     840
agcgtggctc tcgctccaca tgttggcctg ggcctggaga cccgaacaga gacgtggatg     900
agctccgaag gtgcctggaa gcagattcag aaggttgaga cctgggccct gcgacacct     960
agacgggata gcgcgataa gctgaagctt aagggtatgt cctacgcaat gtgcctgaac    1020
acgttcgtgc tgaagaagga ggtttcagag acccagcacg ggacaattct cattaaggtg    1080
gagtacaagg gcgaggacgc gccctgcaag atcccgttca gtactgaaga tggacagggc    1140
aaggctcaca tgggcgact cattactgct aatccagtgg tgaccaagaa ggaagagcca    1200
gtgaatatag aggcagagcc accatttgga gagagcaaca tcgtgatagg tatcggcgat    1260
aaggcactga gatcaactg gtatcgccgc gacaagcgat ccgtggcatt ggcgcctcat    1320
gtgggcctgg gtctagagac ccgcacagag acgtggatga gtagcgaagg cgcgtggaag    1380
cagatccaga aggtcgagac ttgggcactg cggcaccctc gacgtgacaa gcagagaag    1440
ctccgaatca agggaatgag ttacacaatg tgcagcggca agttctcaat tgataaggag    1500
atggccgaga cccagcacgg cacaaccgtg gtcaaggtca agtacgaagg tgcgggcgct    1560
ccttgcaagg tcccaatcga gattagggat gtgaacaagg agaaggtcgt gggaagaatc    1620
attagttcca cgcctcttgc tgagaacact aatagtgtca ccaatatcga gctagagcca    1680
cccttcggag attcttacat tgtcattgga gttggcaatt ccgctcttac tctgcattgg    1740
tttaggagag ataagagaag cgtggccctg gcaccacacg tgggattagg gctggagaca    1800
cgaaccgaga cctggatgag cagcgaagga gcctggaagc agattcagaa ggtcgagact    1860
tgggcccctca gacacccttg atgagcgcgc                                    1890
```

<210> SEQ ID NO 26
<211> LENGTH: 1842
<212> TYPE: DNA
<213> ORGANISM: Artificial Sequence
<220> FEATURE:
<223> OTHER INFORMATION: Description of Artificial Sequence: Synthetic
       fusion sequence comprising domain(s) of Flaviviridae
       strains

<400> SEQUENCE: 26

```
cgtacgatgc tgttgagcgt gccattattg ctggggctgc tgggtctggc tgtggccgac      60
aagcttaccc tgaagggtat gagctacgtg atgtgcactg gttcgttcaa gctagagaag     120
gaggtggcag agacccagca tggaactgtg ttagtacaag ttaagtatga ggggaccgac     180
gcaccctgta agattccatt ctctacccaa gacgagaagg gcgtcacgca gaatggtcgc     240
ttgattacgg ctaatccaat agtgacggac aaggagaagc cagtgaatat cgagacagaa     300
cctccatttg agaatccta cataatagtc ggggccggcg agaaggccct gaagttgtcc      360
tggttcagcg tggccctggc tccacacgtg gccctgggcc tggagacccg aactgagact     420
tggatgtcgt ccgagggcgc ctggaagcag atccagaagg tagagacttg gcccctgcgc     480
catcctagga gagataagag ggacaagttg cagctcaagg gcatgtccta ctccatgtgt     540
acaggtaagt tcaagattgt gaaggagatt gctgagaccc agcacggcac catcgtaata     600
cgggtgcagt acgagggcga tggcagtcca tgtaagatac ctttcgagat cactgacctt     660
gagaagcgcc acgtgcttgg gcggctcatt accgtcaatc caatcgtgac tgagaaggat     720
agtccggtga atattgaggc tgagccgccg tttggggata gttatataat cgttggcgtg     780
gagcccggac aactcaagtt gaattggttc tctgtggcct ggcaccaca cgtggggctg      840
ggcctggaga cacggaccga gacttggatg tcaagtgaag gagcctggaa gcagattcag     900
aaggtggaga cttgggccct tcggcaccct agacgtgata agcgcgacaa gctgaagctc     960
aagggaatgt cttacgccat gtgtctgaat actttcgtcc tgaagaagga ggtgtccgag    1020
actcagcatg ggactatcct gatcaaggtg gagtacaagg gtgaagacgc accatgtaag    1080
ataccattca gcacagagga cggtcagggc aaggctcata cgggcgcct tataactgcc     1140
aatccggttg tgaccaagaa ggaggagccc gtgaacatcg aggcagagcc accattcggc    1200
gagtccaaca tcgtgatagg aatcggtgat aaggccctca agattaattg gtattcagtg    1260
gccctggccc ctcacgtcgg actgggactc gagaccagga cagagacatg gatgtcttct    1320
gagggtgcat ggaagcagat acagaaggtt gagacctggg ccctcaggca cccacgtagg    1380
gacaagcggg agaagttgag gattaagggg atgtcgtaca ccatgtgcag cggcaagttc    1440
tccattgaca ggagatggc agagacgcag cacggaacaa cggtcgttaa ggtcaagtac    1500
gaaggagcgc gcgccccatg caaggtccca atcgagatta gggacgtgaa caaggagaag    1560
gttgtaggac ggattattag tagcaccca ctggcggaga atacgaatag tgtcacgaat     1620
atcgaactgg aaccaccttt cggcgatagc tacatcgtga ttggtgttgg caattccgca    1680
cttacactgc actggtttcg gagagacaag cgaagcgtgg ccctggcccc tcacgtggga    1740
cttggcctgg agacccgcac agagacttgg atgtcctctg aaggagcatg gaagcagatt    1800
cagaaggtgg agacttgggc attacgccac ccatgagcgc gc                       1842
```

<210> SEQ ID NO 27
<211> LENGTH: 1890
<212> TYPE: DNA
<213> ORGANISM: Artificial Sequence
<220> FEATURE:

<223> OTHER INFORMATION: Description of Artificial Sequence: Synthetic
fusion sequence comprising domain(s) of Flaviviridae
strains

<400> SEQUENCE: 27

```
cgtacgatgc tgctatctgt gccactgctc ctgggactgc tggggctggc cgtggctgac      60
aagttgacgc ttaaggggat gtcctacgta atgtgcacag gatcattcaa gctagagaag     120
gaagttgcag agacgcagca cggcaccgtg ctggttcagg tgaagtacga gggcactgat     180
gcaccctgca agatcccatt cagtactcag gacgagaagg gagtcacgca gaatgggagg     240
ctcatcacgg ccaacccaat tgttaccgac aaggagaagc ccgttaatat agagactgaa     300
ccgcccttcg gggagtcata cattattgtg ggcgcagggg agaaggctct gaagctttcc     360
tggttccgta gggataagcg cagcgtggcg ctagcccctc atgtgggtct cgggctggag     420
actcgcaccg agacatggat gtcatccgag ggtgcgtgga agcagatcca gaaggttgag     480
acatgggcac ttcgccaccc acggcgcgac aagcgtgaca agcttcagct gaaggggatg     540
tcttatagca tgtgcacagg caagttcaag atcgtcaagg agatagcaga gacacagcat     600
ggcacaatag tcatacgggt gcaatatgag ggagatggct ctccgtgtaa gatacctttc     660
gagatcaccg atctggagaa gcggcacgtc ctcgggagac taattacggt gaacccaatt     720
gtgacagaga aggatagccc agttaatatt gaggccgaac cacccttcgg agacagctac     780
attatcgtag gagtcgagcc agggcagctg aagctgaact ggttccgcag ggagaagcgt     840
tccgtcgctc ttgttccaca tgtgggaatg ggcctggaga cccgcaccga gacatggatg     900
agcagcgagg gtgcctggaa gcacgtacag agaattgaga cttggatctt aaggcatcct     960
cggcgggata gcgcgacaa gttgaagctg aagggaatgt cttacgcaat gtgtttgaac    1020
actttcgtcc tgaagaagga ggtgtcagag acccagcacg gaactatact tattaaggtt    1080
gagtacaagg gagaagacgc tccttgcaag atcccattct caactgaaga tgggcagggc    1140
aaggcacaca acggaaggct catcacagct aacccagtgg ttaccaagaa ggaggagccc    1200
gtgaacatcg aagccgagcc gccccttcgga gagagcaaca tagtgatcgg tattgggat    1260
aaggctctga gatcaattg gtatcgccgg gacaagagaa gtgtggccct ggccccacat    1320
gtcggcatgg gcttggacac acggacacag acatggatgt ccgctgaagg agcctggagg    1380
caggtggaga aggtcgagac ctgggcgctg cgccacccgc gtcgagacaa gagagagaag    1440
ttaagaatca agggtatgtc ctacacgatg tgttccggta agttctccat agacaaggag    1500
atggctgaga cccagcacgg cactacggtg gtcaaggtga agtatgaggg agccggcgca    1560
ccttgcaagg tgccgatcga gatccgcgac gtcaacaagg agaaggtggt cggggcgcatc    1620
atttccagta ccccattagc tgagaatact aatagcgtga ctaatattga gttggaacca    1680
cccttcggag actcttacat cgttatcggg gtgggcaact cagctcttac acttcactgg    1740
ttccgcaggg agaagagatc agtggcccta accctcact caggcatggg cctggagact    1800
cgggccgaga cctggatgag cagcgagggt gcctggaagc acgcccagcg agtggaatcg    1860
tggattctta ggaatccatg atgagcgcgc                                    1890
```

<210> SEQ ID NO 28
<211> LENGTH: 1482
<212> TYPE: DNA
<213> ORGANISM: Artificial Sequence
<220> FEATURE:
<223> OTHER INFORMATION: Description of Artificial Sequence: Synthetic
fusion sequence comprising domain(s) of Flaviviridae
strains

<400> SEQUENCE: 28

```
cgtacgatgc tgttatctgt acctctcctg ctcggcctcc ttggactggc agttgcagat      60
aagcttacac tcaagggaat gtcctatgtg atgtgtaccg ggtccttcaa gttggagaag     120
gaggtagctg agacgcagca tggcacagtg ctggtgcagg ttaagtatga aggaactgat     180
gctccgtgta agatcccgtt cagtactcag gatgagaagg gtgtgaccca gaatggccgc     240
ttaattacag ccaaccctat cgtaactgac aaggagaagc tgtgaacat cgagactgaa      300
ccacccttcg gtgagagtta tataatagtt ggcgccggag agaaggccct caagcttagc     360
tggtttcggc gcgacaagcg agataagctc aacttaagg gaatgtcata ctcaatgtgc      420
acaggtaagt tcaagatagt gaaggagata gccgagaccc agcatggcac catcgtgatc     480
agagtccaat atgaaggaga cgggtctcct tgtaagatcc cattcgagat aacagacttg     540
gagaagaggc acgtgctggg acgtctgata acagttaatc ccatagttac cgagaaggat     600
agccctgtta acattgaggc tgaacctccc ttcggagatt cctacattat tgtcggcgtg     660
gagccaggtc agctgaagct taactggttc agacgggaca gcgcgacaa gctgaagttg      720
aagggcatgt cctatgcaat gtgtctcaat actttcgttc tcaagaagga agtgagcgag     780
acacagcatg gcaccatatt aattaaggtt gagtacaagg gtgaggatgc tccttgcaag     840
attcctttca gcaccgagga tggacagggc aaggcccaca atggtcggct gatcaccgcc     900
aaccctgtgg taaccaagaa ggaagagccc gtcaacatag aagccgagcc gccgtttggc     960
gagtccaata tagtaatcgg catcggagat aaggccttga agattaattg gtacaggcgg    1020
gataagcgcg agaagttacg gattaagggt atgtcttaca ctatgtgtag cggtaagttt    1080
agcatcgaca aggagatggc agagacccag catggcacta ccgtggtcaa ggtgaagtac    1140
gaaggagctg gagcaccatg taaggtccct atcgagatcc gcgacgtgaa caaggagaag    1200
gtggtgggaa gaatcatctc ttccacacct ctggcagaga acacgaatag cgtgactaat    1260
atcgaacttg agcctccttt cggcgattcc tacatcgtta ttggcgtggg caactccgcc    1320
ctgacactgc attggtttag acgtgacaag cgtagcgtgg cccttgcacc acacgtgggc    1380
ctaggcctgg agacgcgtac agagacatgg atgagcagtg aaggagcctg gaagcagatt    1440
cagaaggtcg agacctgggc tctcagacat ccttgagcgc gc                       1482
```

<210> SEQ ID NO 29
<211> LENGTH: 1440
<212> TYPE: DNA
<213> ORGANISM: Artificial Sequence
<220> FEATURE:
<223> OTHER INFORMATION: Description of Artificial Sequence: Synthetic fusion sequence comprising domain(s) of Flaviviridae strains

<400> SEQUENCE: 29

```
cgtacgatgc tcctaagcgt tccactgctt ctgggactgc tgggtttggc cgttgccgac      60
aagctcacgc tcaaggggat gagctacgtc atgtgcacag gctcattcaa gttggagaag     120
gaagtcgccg agacgcagca cggaacagta ctcgtgcagg tcaagtatga gggcaccgac     180
gctccatgca agatcccgtt ctccacacag gacgagaagg gcgttactca gaacggaaga     240
ttaattactg ccaatcctat agtaacagac aaggagaagc tgtgaatat tgagactgag      300
cctcccttcg gtgaatccta catcattgta ggggctggcg agaaggcttt gaagctctcc     360
tggtttgata agctgcagct caagggaatg tcgtattcaa tgtgcactgg aagttcaag       420
```

-continued

```
attgtgaagg agattgcaga gactcaacac ggcaccattg tgataagggt ccagtacgag    480
ggtgatgggt caccctgcaa gattcccttt gagatcacag accttgagaa gaggcacgta    540
cttgggcgat taattaccgt gaatcctatt gtgactgaga aggatagtcc cgtgaacatt    600
gaagctgagc ctcctttcgg agatagctac attatcgtgg gagtcgagcc tggccagttg    660
aagctcaact ggtttgataa gctgaagctc aagggcatgt cctacgctat gtgcttgaat    720
acatttgtgc tgaagaagga ggtgagtgag acccaacacg gaaccatcct gatcaaggtg    780
gagtacaagg gtgaagatgc accttgcaag atccctttct ccactgaaga cgggcagggc    840
aaggcccata atgggagact cataacagct aatccagtgg tcaccaagaa ggaagaacca    900
gtcaacatcg aggcggagcc accatttggg gagagtaaca tcgtgatcgg tattggcgat    960
aaggccctga agattaactg gtatgagaag ttgagaatta aggggatgag ctataccatg   1020
tgctcaggta agttcagcat cgataaggag atggccgaga cacagcacgg gaccacagtt   1080
gtgaaggtga agtacgaggg cgctggggcc ccatgcaagg tgcctatcga gattcgcgac   1140
gtgaacaagg agaaggtcgt ggggcgaatc atctcatcca cccctctcgc agagaacacg   1200
aactctgtga ccaatattga gctggaacca cctttcggag actcatatat cgtcataggc   1260
gtcggcaatt cagctttgac attgcactgg ttcagacggg acaagcggtc cgttgccctg   1320
gctccacacg tcggcctggg ccttgagact aggacggaga cctggatgtc ctccgagggc   1380
gcctggaagc agatccagaa ggtggagacc tgggccctgc gccacccctg ataggcgcgc   1440
```

```

<210> SEQ ID NO 30
<211> LENGTH: 40
<212> TYPE: PRT
<213> ORGANISM: Flavivirus sp.

<400> SEQUENCE: 30

Ser Val Ala Leu Ala Pro His Val Gly Leu Gly Leu Glu Thr Arg Thr
1               5                   10                  15

Glu Thr Trp Met Ser Ser Glu Gly Ala Trp Lys Gln Ile Gln Lys Val
            20                  25                  30

Glu Thr Trp Ala Leu Arg His Pro
        35                  40

<210> SEQ ID NO 31
<211> LENGTH: 40
<212> TYPE: PRT
<213> ORGANISM: Flavivirus sp.

<400> SEQUENCE: 31

Ser Val Ala Leu Ala Pro His Val Gly Met Gly Leu Asp Thr Arg Thr
1               5                   10                  15

Gln Thr Trp Met Ser Ala Glu Gly Ala Trp Arg Gln Val Glu Lys Val
            20                  25                  30

Glu Thr Trp Ala Leu Arg His Pro
        35                  40

<210> SEQ ID NO 32
<211> LENGTH: 40
<212> TYPE: PRT
<213> ORGANISM: Flavivirus sp.

<400> SEQUENCE: 32

Ser Val Ala Leu Thr Pro His Ser Gly Met Gly Leu Glu Thr Arg Ala
1               5                   10                  15
```

```
Glu Thr Trp Met Ser Ser Glu Gly Ala Trp Lys His Ala Gln Arg Val
                20                  25                  30

Glu Ser Trp Ile Leu Arg Asn Pro
        35                  40

<210> SEQ ID NO 33
<211> LENGTH: 40
<212> TYPE: PRT
<213> ORGANISM: Flavivirus sp.

<400> SEQUENCE: 33

Ser Val Ala Leu Val Pro His Val Gly Met Gly Leu Glu Thr Arg Thr
1               5                   10                  15

Glu Thr Trp Met Ser Ser Glu Gly Ala Trp Lys His Ala Gln Arg Ile
                20                  25                  30

Glu Thr Trp Ile Leu Arg His Pro
        35                  40

<210> SEQ ID NO 34
<211> LENGTH: 5
<212> TYPE: PRT
<213> ORGANISM: Artificial Sequence
<220> FEATURE:
<223> OTHER INFORMATION: Description of Artificial Sequence: Synthetic
      pentapeptide binding segment

<400> SEQUENCE: 34

Arg Arg Asp Lys Arg
1               5

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence: Synthetic
      pentapeptide binding segment

<400> SEQUENCE: 35

Arg Arg Glu Lys Arg
1               5
```

CHIMERIC POLY PEPTIDES AND THE THERAPEUTIC USE THEREOF AGAINST A FLAVIVIRIDAE INFECTION

This application is a divisional of application Ser. No. 14/477,223, filed Sep. 4, 2014, which is a continuation of application Ser. No. 13/089,705, filed Apr. 19, 2011 (now U.S. Pat. No. 8,853,379), which is a continuation of application Ser. No. 11/917,907 (now U.S. Pat. No. 8,337,857), which is the national stage of International Application No. PCT/FR2006/001396, filed Mar. 20, 2006, and which claims priority to Canadian Application No. CA 2 508 266, filed Jun. 20, 2005.

SEQUENCE LISTING

The instant application contains a Sequence Listing which has been submitted in ASCII format via EFS-Web and is hereby incorporated by reference in its entirety. Said ASCII copy, created on Apr. 20, 2012, is named DI20521A.txt and is 85,853 bytes in size.

FIELD OF THE INVENTION

The present invention relates to the construction of a chimeric polypeptide for use in the prevention or treatment of a Flaviviridae infection. The present invention also relates to the use of the chimeric polypeptide in the production of recombinant viral vectors, such as a live measles viral vector to act as a vaccine.

BRIEF DESCRIPTION OF THE PRIOR ART

Flaviviruses (the Flaviviridae family) are envelope viruses the genome of which is a RNA molecule with a positive polarity. The flavivirion is composed of three structural proteins designated C (core protein), M (membrane protein) and E (envelope protein). The E protein, which is exposed on the virus surface, is responsible for the principal biological functions of the virion, including attachment of the virus and specific membrane fusion. Translation of genomic RNA produces a precursor polyprotein which is simultaneously cleaved by cellular and viral proteases to generate individual viral proteins: three structural proteins C, prM (the glycosylated precursor of the M protein), E, and seven non-structural proteins NS1 to NS5. Replication of flaviviruses occurs in the cytoplasm of infected cells. Flaviviruses have complex natural transmission cycles which involve several natural hosts (mainly mammals and birds) and vectors, the latter being hematophage arthropods such as ticks and mosquitoes. These viruses are the principal cause of severe human diseases such as hemorrhagic manifestations or meningo-encephalitic syndromes. The dengue virus (DEN) is one of the two major flaviviruses known to be the cause of severe hemorrhagic diseases across the world.

Dengue is an emerging disease and a bane to public health. Development of live-attenuated vaccine candidates against the four serotypes of the dengue virus has been carried out for more than 50 years. The search for a vaccine is hindered by the absence of an animal model which mimics the disease caused by the dengue virus, namely the hemorrhagic fever of dengue and the shock syndrome associated therewith. Vaccine effectiveness can be evaluated in the mouse using a neurovirulent strain of DEN virus adapted to the mouse, which kills adult animals after intracerebral inoculation. However, studies based on that type of murine model do not reflect the activity of the dengue virus in man. In the monkey, protection can only be demonstrated by measuring the reduction in viremia after an experimental infectious challenge. Thus, the ultimate test for a vaccine against dengue must be based on clinical trials carried out in man. The majority of attenuated vaccine candidates which have been developed over the last 50 years have been either too reactogenic or insufficiently immunogenic in clinical trials. Several attenuated tetravalent candidates are currently in phase I or II clinical trials. The difficulty in the development of this type of live-attenuated tetravalent vaccines appears to be in obtaining a balanced mixture of four valencies in order to generate protective immunity against the four serotypes.

Various live chimeric vaccine candidates are also being developed. They are based on the exchange of homologous structural genes between different flaviviruses. Several types of intertype chimeric viruses have been constructed and tested in the mouse or monkey. Chimeric viruses have been constructed with Chimerivax® techniques based on the yellow fever vaccinal virus (YF-17D). Tetravalent mixtures of those YF-17D/DEN chimeras have been tested in the rhesus monkey. Here again, the balance between the four chimeric viruses is difficult to obtain for uniform immunization. A phase I/II clinical test is currently being prepared to test a chimerivax-dengue 2 vaccines. Other approaches include subunit candidate vaccines produced from an expression vector, and naked DNA type candidates which are in pre-clinical development. Thus, the development of a tetravalent vaccine against the dengue virus is still an unresolved problem, one of the most important on the list of the World Health Organization.

Thus, there is a need to develop novel effective vaccine candidates which are easy to produce and to formulate, for the prevention or treatment of an infection by a virus of the Flaviviridae family such as the dengue virus.

SUMMARY OF THE INVENTION

The present invention relates to a chimeric polypeptide and its applications in the prevention or treatment of an infection by Flaviviridae.

More particularly, an object of the present invention is a chimeric polypeptide comprising a peptide of a subdomain the E protein of Flaviviridae bound to a peptide of a subdomain of the Membrane M protein of Flaviviridae.

An object of the present invention is also an isolated or purified polynucleotide coding for a chimeric polypeptide of the invention.

An object of the present invention is also a recombinant measles viral vector into the genome of which a polynucleotide of the invention has been inserted.

An object of the invention also pertains to purified monoclonal or polyclonal antibodies specifically recognizing at least one polynucleotide as defined above and/or the chimeric polypeptide of the invention.

The invention also relates to the use of a viral vector of the invention for the preparation of an immunogenic composition intended for the prevention or treatment of a Flaviviridae infection in a sensitive species.

The present invention also relates to cloning or expression vectors comprising a polynucleotide of the invention.

Another object of the present invention is to provide an immunogenic composition intended for the prevention and/or treatment of a Flaviviridae infection in a sensitive species, characterized in that it comprises at least one of the following elements:

a chimeric polypeptide as defined above;

a polynucleotide according to the invention;
a recombinant viral vector according to the invention;
an antibody according to the invention; and
a cloning and/or expression vector according to the invention.

The present invention also proposes a method for preventing and/or treating a Flaviviridae infection in a sensitive species, comprising administering a pharmaceutically effective amount of at least one of the following elements:
a chimeric polypeptide as defined above;
a polynucleotide according to the invention;
a recombinant viral vector according to the invention;
an antibody according to the invention; and
a cloning and/or expression vector according to the invention.

BRIEF DESCRIPTION OF THE FIGURES

FIG. 1 shows the 384 nucleotide (nt) sequence coding for the [EDIII]$_{DV-1}$ domain of the FGA/89 viral strain fused via the Arg-Ser dipeptide to the signal peptide of calreticulin (ssCRT) flanked by the two BsiWI (5') and BssHII (3') sites necessary for insertion into the MVA$_{Schw}$ vector;

FIG. 2 shows the 516 nucleotide (nt) sequence coding for the [EDIII+M$^{1-40}$]$_{Dv-1}$ fusion protein of the FGA/89 viral strain fused via the Arg-Ser dipeptide to the signal peptide of calreticulin (ssCRT) flanked by the two BsiWI (5') and BssHII (3') sites necessary for insertion into the MV$_{Schw}$ vector;

FIG. 3 shows Vero cells infected with recombinant measles viral vectors according to the invention. Multiplicity of infection 10 TCIP50/cell for 30 h. Immunofluorescence carried out with a specific anti-DV-1 HMAF antibody;

FIG. 4 shows the expression and secretion of the [EDIII] DV-1 and [EDIII+M$^{1-40}$]$_{DV-1}$ antigenic domains in cytoplasmatic lysates (C) and supernatants (S) from Vero cells infected with recombined MVSchw-DV-1 viruses;

FIG. 5 shows the expression and secretion of the [EDIII] DV-1 and [EDIII+M$^{1-40}$]$_{DV-1}$ antigenic domains in filtered and concentrated supernatants from drosophila S2 cells inducibly expressing these antigens;

FIG. 6 shows a nucleotide sequence coding for a chimeric polypeptide according to a preferred mode of the invention;

FIG. 7 shows an amino acid sequence of a chimeric polypeptide according to a preferred mode of the invention and the nucleotide sequence coding for it;

FIG. 8 shows an amino acid sequence of a dimer of the ectodomain III (EDIII) according to a preferred mode of the invention, and the nucleotide sequence coding for it;

FIG. 9 shows an amino acid sequence of a dimer of the ectodomain III (EDIII) according to a preferred mode of the invention, and the nucleotide sequence coding for it;

FIG. 10 shows an amino acid sequence of a chimeric polypeptide according to a preferred mode of the invention, and the nucleotide sequence coding for it;

FIG. 11 shows an amino acid sequence of the ectodomain III (EDIII) according to a preferred mode of the invention, and the nucleotide sequence coding for it;

FIG. 12 shows an amino acid sequence of a dimer of the ectodomain III (EDIII) according to a preferred mode of the invention, and the nucleotide sequence coding for it;

FIG. 13 shows a nucleic acid sequence coding for a peptide of the ectodomain III (EDIII) peptide according to a preferred mode of the invention;

FIG. 14 shows a nucleotide sequence coding for a chimeric polypeptide according to a preferred mode of the invention;

FIGS. 15 to 19 show an amino acid sequence of chimeric polypeptides according to a preferred mode of the invention;

FIGS. 20 to 24 show a nucleotide sequence coding respectively for the chimeric polypeptides of FIGS. 15 to 19;

FIGS. 25 to 29 respectively show a representative diagram of the chimeric polypeptides of FIGS. 15 to 19;

FIG. 30 shows the peptide sequence of the apoptoM sequence of four serotypes of the dengue virus used in the construction of a chimeric precursor according to the invention.

DETAILED DESCRIPTION OF THE INVENTION

Figure 25:
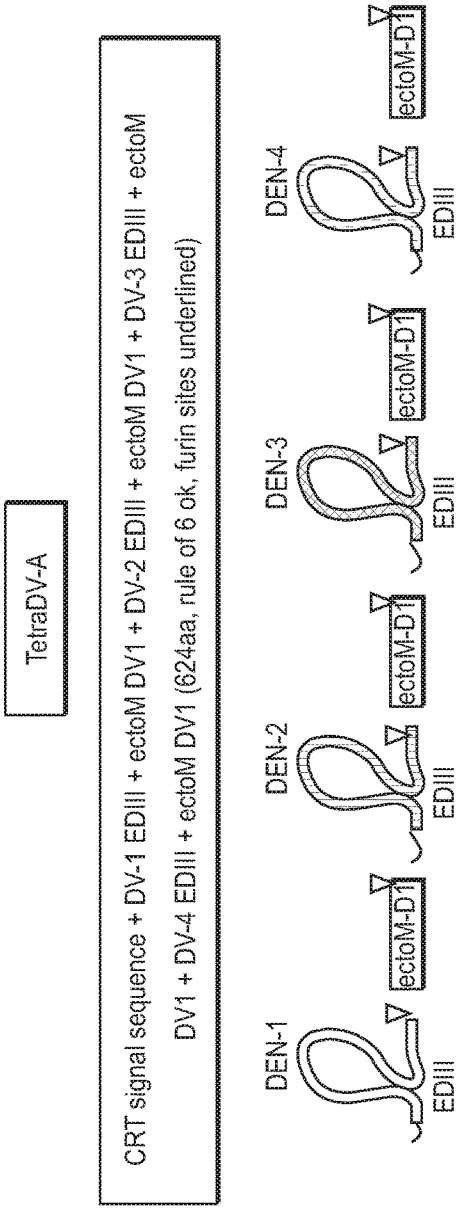

The originality of the present invention is based on the construction of a chimeric polypeptide and its applications in the prevention or treatment of an Flaviviridae infection. The term "Flaviviridae" means a virus selected from the group constituted by the West Nile virus, dengue virus, Japanese encephalitis virus and yellow fever virus.

1. Polypeptide and Polynucleotide

In a first aspect, the present invention relates to a chimeric polypeptide comprising a peptide of a subdomain of the E protein of Flaviviridae linked to a peptide of a subdomain of the membrane M protein of Flaviviridae. The invention also pertains to a polypeptide which consists of said peptides.

The term "polypeptide" as used in the present invention means both proteins and peptides. By "chimeric polypeptide" it is meant any protein or peptide comprising sub-portions of different origins, for example a polypeptide A deriving from a first species and a polypeptide (protein or peptide) deriving from a second species. A protein or peptide is also considered to be a chimeric polypeptide if it includes sub-portions deriving from different proteins or peptides from the same species, or even from the same protein or peptide from different species.

Preferably, the peptide of a subdomain of the E protein consists of the ectodomain III comprising an amino acid sequence as defined in any one of the following sequences:
   amino acids 19 to 120 of SEQ ID NO: 1;
   amino acids 19 to 119 of SEQ ID NO: 3;
   amino acids 21 to 123 of SEQ ID NO: 6;
   amino acids 21 to 121 of SEQ ID NO: 12; and
   amino acids 21 to 123 of SEQ ID NO: 14.

More particularly, the peptide of a subdomain of the E protein consists of a dimer of the ectodomain III of the dengue 1, 2, 3 or 4 virus comprising an amino acid sequence as defined in any one of the following sequences:
   amino acids 21 to 262 of SEQ ID NO: 8; and
   amino acids 21 to 262 of SEQ ID NO: 10;
   or a tetramer of the ectodomain III of the dengue 1, 2, 3, 4 virus comprising a sequence ranging from amino acid 21 to 494 of SEQ ID NO: 16 or ranging from amino acid 18 to 429 of 5 SEQ ID NO: 24.

Regarding the peptide of a subdomain of the M protein, this in particular consists of the ectodomain 1-40 comprising an amino acid sequence ranging from position 123 to 170 of SEQ ID NO: 3 or in the apoptoM sequence comprising an amino acid sequence ranging from position 154 to 170 of SEQ ID NO: 3 or ranging from position 122 to 132 of SEQ ID NO: 12.

In a preferred mode, the chimeric polypeptide of the invention further comprises a binding segment binding the peptide of a subdomain of the E protein to the peptide of a subdomain of the M protein. Said binding segment is preferably a pentapeptide with sequence: RRDKR (SEQ ID NO: 34) or RREKR (SEQ ID NO: 35).

Highly preferably, the chimeric polypeptide of the invention comprises an amino acid sequence as defined in any one of the following sequences:
  a) amino acids 19 to 162 of SEQ ID NO: 3;
  b) amino acids 21 to 168 of SEQ ID NO: 6;
  c) amino acids 21 to 132 of SEQ ID NO: 12;
  d) amino acids 18 to 624 of SEQ ID NO: 20;
  e) amino acids 18 to 609 of SEQ ID NO: 21;
  f) amino acids 18 to 624 of SEQ ID NO: 22;
  g) amino acids 18 to 489 of SEQ ID NO: 23; and
  h) amino acids 21 to 474 of SEQ ID NO: 24.

The invention also relates to polypeptides (and fragments thereof) which are coded by the nucleotide sequences mentioned below.

Highly preferably, the polypeptide of the invention has a percentage identity of at least 80% after optimum alignment with a sequence as defined in any one of amino acid sequences a) to h) defined above, preferably at least 90%, more preferably at least 98% and still more preferably at least 100%.

In a connected aspect, the invention relates to an isolated or purified polynucleotide coding for a chimeric polypeptide as defined above.

By "isolated or purified", it is meant molecules which have been altered by man from their native state, i.e. if such molecules exist in nature, they have been changed and/or removed from their initial environment. As an example, a polynucleotide or a polypeptide naturally present and found in the biological environment of a living organism which naturally expresses it is not "isolated" in this context. However, the same polynucleotide or polypeptide when separated from its natural environment and/or obtained by cloning, amplification and/or chemical synthesis is considered in the present invention to be "isolated". Further, a polynucleotide or polypeptide which is introduced into an organism by transformation, gene manipulation or any other recombination method is "isolated" even if it is present in said organism.

By the terms "nucleotide sequence", "nucleic acid", "nucleic sequence or nucleic acid sequence", "polynucleotide", oligo nucleotide", "polynucleotide sequence", which will be used indiscriminately in the present description, it is meant a precise chain of nucleotides, which may or may not be modified, which allows to define a fragment or a region of a nucleic acid, which may or may not comprise non-natural nucleotides and which can correspond both to a double-stranded DNA, a single-stranded DNA or to transcription products of said DNAs. Thus, the nucleic sequences of the invention also encompass PNAs (peptide nucleic acid) or the like. The polynucleotide fragments of the invention comprise at least 15 consecutive nucleotides. Preferably, they comprise at least 20 consecutive nucleotides and more preferably they comprise at least 30 consecutive nucleotides.

The invention also pertains to fragments of polynucleotides, which consist of fragments of 15, 20 or 30 successive nucleotides.

Any polynucleotide which has been chemically, enzymatically or metabolically modified but which has retained the biochemical properties of the original chimeric polypeptide is included within the scope of the present invention.

In a preferred embodiment, the polynucleotide of the present invention, when it codes for a chimeric polypeptide of the invention, advantageously comprises a nucleotide sequence as defined in any one of the following sequences:
  a) nucleotides 7 to 492 of SEQ ID NO: 4;
  b) SEQ ID NO: 5;
  c) Nucleotides 7 to 504 of SEQ ID NO: 7;
  d) Nucleotides 7 to 504 of SEQ ID NO: 13; and
  e) SEQ ID NOs: 25 to 29.

Highly preferably, the polynucleotide of the invention has a percentage identity of at least 80% after optimum alignment with a sequence as defined in any one of the nucleotide sequences a) to e) defined above, preferably at least 90%, more preferably at least 98% and most preferably at least 100% identity.

The term "percentage identity" between two nucleic acid or amino acid sequences as used in the present invention means a percentage of identical nucleotides or amino acid residues between the two sequences to be compared, obtained after best alignment, that percentage being purely statistical and the differences between the two sequences being randomly distributed and over their entire length. By "best alignment" or "optimum alignment", it is meant the alignment at which the percentage identity determined as below is the highest. Sequence comparisons between two nucleic acid or amino acid sequences are traditionally carried out by comparing these sequences after having aligned them in an optimum manner, said comparison being carried out using comparison segments or windows to identify and compare local regions with sequence similarity. The optimum sequence alignment for comparison may be carried out manually or using a Smith and Waterman (1981) local homology algorithm, using the Neddleman and Wunsch (1970) local homology algorithm, using the Pearson and Lipman (1988) sequence similarity search method, or using software employing these algorithms (GAP, BESTFIT, BLAST P, BLAST N, FASTA and TFASTA in the Wisconsin Genetics Software Package, Genetics Computer Group, 575 Science Dr, Madison, Wis.). To obtain an optimal alignment, the BLAST program is preferably used, with the BLOSUM 62 matrix. It is also possible to use PAM or PAM250 matrices.

The percentage identity between two nucleic acid or amino acid sequences is determined by comparing these two sequences aligned in an optimum manner, the nucleic acid or amino acid sequence to be compared possibly comprising additions or deletions compared with the reference sequence for optimum alignment between these two sequences. The percentage identity is calculated by determining the number of identical positions for which the nucleotide or amino acid residue is identical between the two sequences, dividing this number of identical positions by the total number of compared positions and multiplying the result obtained by 100 to obtain the percentage identity between these two sequences.

The term "nucleic sequences having a percentage identity of at least 80%, preferably at least 90%, more preferably at least 98% after optimum alignment with a reference sequence", is intended to designate nucleic sequences having, with respect to the reference nucleic acid, certain modifications, in particular a deletion, truncation, extension, chimeric fusion, and/or a substitution, in particular a point substitution, and for which the nucleic sequence has at least 80%, preferably at least 90%, more preferably at least 98% identity after optimum alignment with the reference nucleic sequence. Preferably, the specific hybridization conditions or high stringency conditions will be such that they ensure at least 80%, preferably at least 90%, more preferably at least 98% identity after optimum alignment between one of the two sequences and the complementary sequence of the other.

A hybridization under high stringency conditions means that the temperature and ionic strength conditions are selected so that they can maintain the hybridization between two complementary nucleic acid fragments. By way of illustration, the highly stringent conditions for the hybridization step with the aim of defining the nucleotide sequences described above are advantageously as follows.

DNA-DNA or DNA-RNA hybridization is carried out in two steps: (1) pre-hybridization at 42° C. for 3 hours in a phosphate buffer (20 mM, ph 7.5) containing 5×SSC (1×SSC corresponds to a solution of 0.15 M NaCl+0.015 M of sodium citrate), 50% formamide, 7% sodium dodecyl sulphate (SDS), 10×Denhardt's solution, 5% dextran sulphate and 1% salmon sperm DNA; (2) hybridization proper for 20 hours at a temperature depending on the probe size (i.e.: 42° C. for a probe size>100 nucleotides), followed by 2 washings of 20 minutes at 20° C. in 2×SSC+2% SDS, 1 washing of 20 minutes at 20° C. in 0.1×SSC+0.1% SDS. The final washing is carried out in 0.1×SSC+0.1% SDS for 30 minutes at 60° C. for a probe size>100 nucleotides. The high stringency hybridization conditions described above for a polynucleotide of a defined size may be adapted by the skilled person for larger or smaller oligonucleotides, as discussed by Sambrook et al, 1989.

The polypeptides and polynucleotides of the present invention may be prepared using any appropriate process. They may in particular be obtained by chemical synthesis, but it is also possible to obtain them via a biological route pathway, especially using different vectors in appropriate cell cultures. The peptides of the present invention may, if necessary, be in the deglycosylated or glycosylated form. A person skilled in the field of the invention will be able to obtain different polynucleotides/polypeptides and will also be able to determine which of the polynucleotides/polypeptides obtained have a suitable biological activity.

2. Recombinant Viral Vector

In a further aspect, the invention concerns a recombinant measles viral vector with a polynucleotide of the invention inserted into the genome thereof. Such vectors are prepared using methods which are routinely used by the skilled person and the resulting clones may be introduced into a suitable host using standard methods which are known to the skilled person.

In a preferred mode, the recombinant viral vector of the invention is advantageously a live measles (Schwarz strain) viral vector, such as those selected from the group of viral vectors constituted by those deposited at the CNCM under numbers I-3440, I-3442, I-3452, I-3453, I-3454, I-3455, I-3619, I-3620, I-3621, I-3622 and I-3623. The complete antigenome sequence of the measles Schwarz strain virus can, for example, be obtained from pTM plasmids of strains deposited under numbers I-3440 and I-3442.

The vector pTM-MVSchw2-[EDIII+M$^{1-40}$]WNV(IS-98-ST1) was deposited at the CNCM (Paris, France) on 26 May 2005 under number I-3440.

This vector is a pTM plasmid containing the complete antigenome of the measles virus, Schwarz strain, and an additional expression unit placed between the P and M genes containing the sequence of the domain III of the envelope E protein of West Nile virus (WNV IS-98-ST1) fused to the sequence 1-40 of the membrane protein.

The vector may be cultivated in 100 µ/ml LB ampicillin medium after inoculating small colonies.

It is preserved long-term by freezing at −80° C.

The vector pTM-MVSchw2-[EDIII+ApoptoM]DV-1 (FGA89) was deposited at the CNCM (Paris, France) on 26 May 2005 under number I-3442.

This vector is a pTM plasmid containing the complete antigenome of the measles virus, Schwarz strain, and an additional expression unit placed between the P and M genes containing the sequence of the domain III of the envelope E protein of the dengue 1 virus, FGA89 strain, fused to the apoptotic sequence of the Membrane M protein.

The vector may be cultivated in 100 µ/ml LB ampicillin medium after inoculating small colonies.

It is preserved long-term by freezing at −80° C.

The vector pTRE2-SSCRT-ApoptoMdenl/DIII-Hα1-2 was deposited at the CNCM (Paris, France) on 16 Jun. 2006 under number I-3452.

This vector is a pTRE$_2$ plasmid containing the sequence of the signal peptide of human calreticulin fused to the pro-apoptotic sequences of the M protein and to the ectodomains III of the E protein with the a-helice sequences of the dengue 1 and 2 viruses.

The sequence of the insert contained in the plasmid and constituting a polynucleotide of the invention is SEQ ID NO: 9 shown in FIG. 8.

The vector may be cultivated in 100 g/ml LB ampicillin medium.

It is preserved long-term by freezing at −80° C.

The vector pTRE$_2$-ssCRT-ApoptoMdenl/DIII-Hα3-4 was deposited at the CNCM (Paris, France) on 16 Jun. 2006 under number I-3453.

This vector is a pTRE$_2$ plasmid containing the sequence of the signal peptide of human calreticulin fused to the pro-apoptotic sequences of the M protein of the dengue 1 virus and to the sequences of the ectodomains III Hα of the dengue 3-4 viruses The sequence of the insert contained in the plasmid and constituting a polynucleotide of the invention is SEQ ID NO: 9 shown in FIG. 9.

The vector may be cultivated in LB ampicillin 100 µ/ml medium.

It is preserved long-term by freezing at −80° C.

The vector pTRE2-ssCRT-ApoptoMdenl/DIII-Hα1-2-3-4 was deposited at the CNCM (Paris, France) on 16 Jun. 2006 under number I-3454.

This vector is a pTRE$_2$ plasmid containing the sequence of the signal peptide of human calreticulin fused to the pro-apoptotic sequences of the M protein of dengue 1 virus and to the sequences of the ectodomains III with a helices (Hα) of the E proteins of the dengue 1-2-3-4 viruses.

The sequence of the insert contained in the plasmid and constituting a polynucleotide of the invention is SEQ ID NO: 4 shown in FIG. 2.

The vector may be cultivated in LB ampicillin 100 µ/ml medium.

It is preserved long-term by freezing at −80° C.

The vector pTRE2-ssCRT-ApoptoM40den1/DIII-Hα1-2-3-4 was deposited at the CNCM (Paris, France) on 16 Jun. 2005 under number I-3455.

This vector is a pTRE2 plasmid containing the signal peptide sequence of human calreticulin fused to the pro-apoptotic sequences of the M protein of dengue 1 virus and to the sequences of the ectodomains III with a helices (Ha) of the E proteins of the dengue 1, 2, 3, 4 viruses.

The sequence of the insert contained in the plasmid and constituting a polynucleotide of the invention is SEQ ID NO: 17 shown in FIG. 12.

The vector may be cultivated in 100 g/ml LB ampicillin medium.

It is preserved long-term by freezing at −80° C.

The vector pUC57-TetraDVA (introduced into an *E. coli* strain) was deposited at the CNCM (Paris, France) on 14 Jun. 2006 under number 1-3619.

This vector is a pUC plasmid containing a nucleotide sequence optimized for the expression in mammalian cells of a tetrameric construct of the ectodomains III of the envelope E protein of the 4 serotypes (1, 2, 3, 4) of the dengue virus, fused to the ectodoinain of the Membrane M protein.

The insert contained in the plasmid vector is shown in FIG. 25.

The strain containing the vector may be cultivated in 100 μ/ml LB ampicillin medium.

The vector pUC57-TetraDVB (introduced into an *E. coli* strain) was deposited at the CNCM (Paris, France) on 14 Jun. 2006 under number 1-3620.

This vector is a pUC plasmid containing a nucleotide sequence optimized for the expression in mammalian cells of a tetrameric construct of the ectodomains III of the envelope E protein of the 4 serotypes (1, 2, 3, 4) of the dengue virus, fused to the ectodomain of the Membrane M protein.

Figure 26:
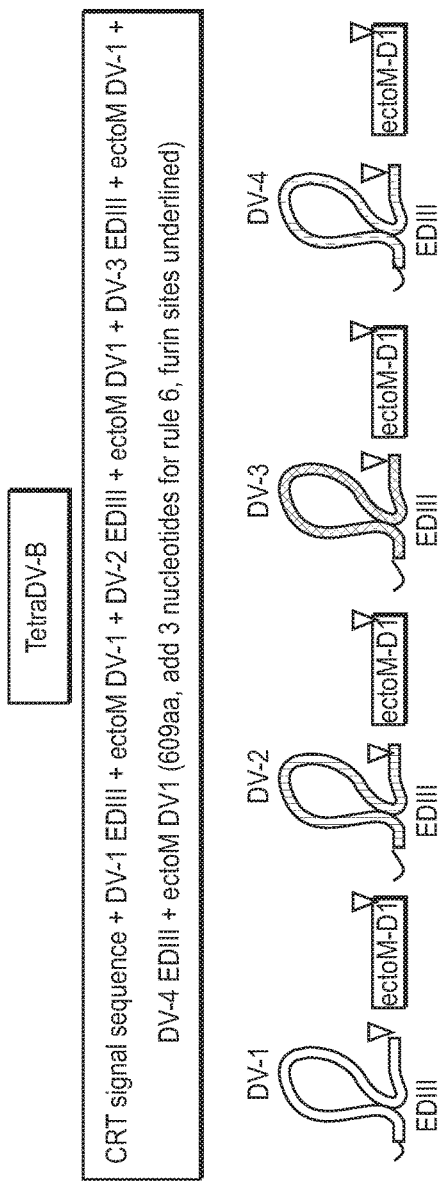

The insert contained in the plasmid vector is shown in FIG. 26.

The strain containing the vector may be cultivated in 100 μ/ml LB ampicillin medium.

The vector pUC57-TetraDVC (introduced into an *E. coli* strain) was deposited at the CNCM (Paris, France) on 14 Jun. 2006 under number 1-3621.

This vector is a pUC plasmid containing a nucleotide sequence optimized for the expression in mammalian cells of a tetrameric construct of the ectodomains III of the Envelope E protein of the 4 serotypes (1, 2, 3, 4) of the dengue virus, fused to the ectodomain of the Membrane M protein.

Figure 27:
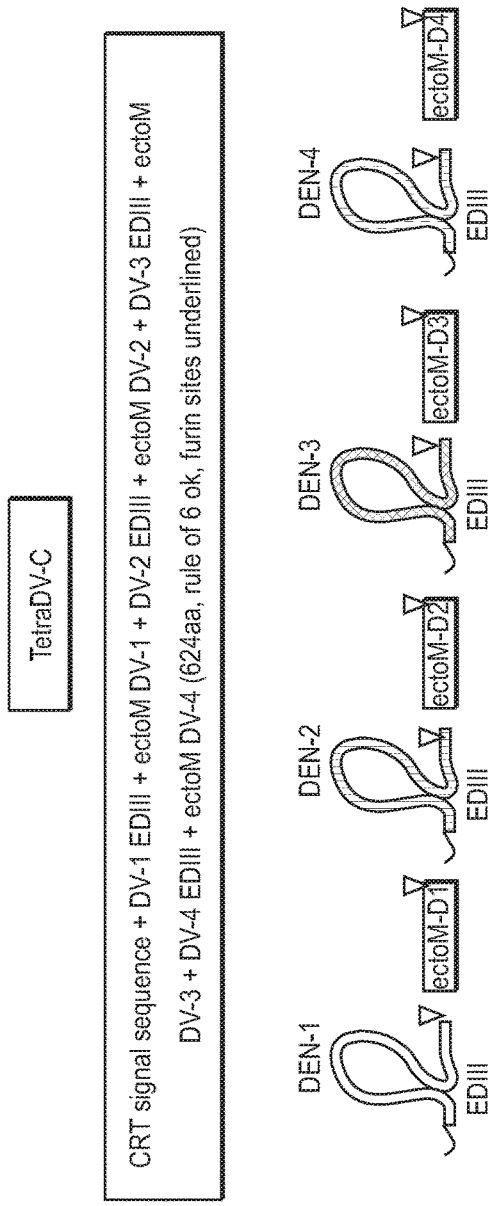

The insert contained in the plasmid vector is shown in FIG. 27.

The strain containing the vector may be cultivated in 100 μ/ml LB ampicillin medium.

The vector pUC57-TetraDVD (introduced into an *E. coli* strain) was deposited at the CNCM (Paris, France) on 14 Jun. 2006 under number 1-3622.

This vector is a pUC plasmid containing a nucleotide sequence optimized for the expression in mammalian cells of a tetrameric construct of the ectodomains III of the Envelope E protein of the 4 serotypes (1, 2, 3, 4) of the dengue virus, fused to the ectodomain of the Membrane M protein.

The insert contained in the plasmid vector is shown in FIG. 28.

The strain containing the vector may be cultivated in 100 μ/ml LB ampicillin medium.

The vector pUC57-TetraDVE (introduced into an *E. coli* strain) was deposited at the CNCM (Paris, France) on 14 Jun. 2006 under number 1-3623.

This vector is a pUC plasmid containing a nucleotide sequence optimized for the expression in mammalian cells of a tetrameric construct of the ectodomains III of the Envelope E protein of the 4 serotypes (1, 2, 3, 4) of the dengue virus, fused to the ectodomain of the Membrane M protein.

Figure 29:
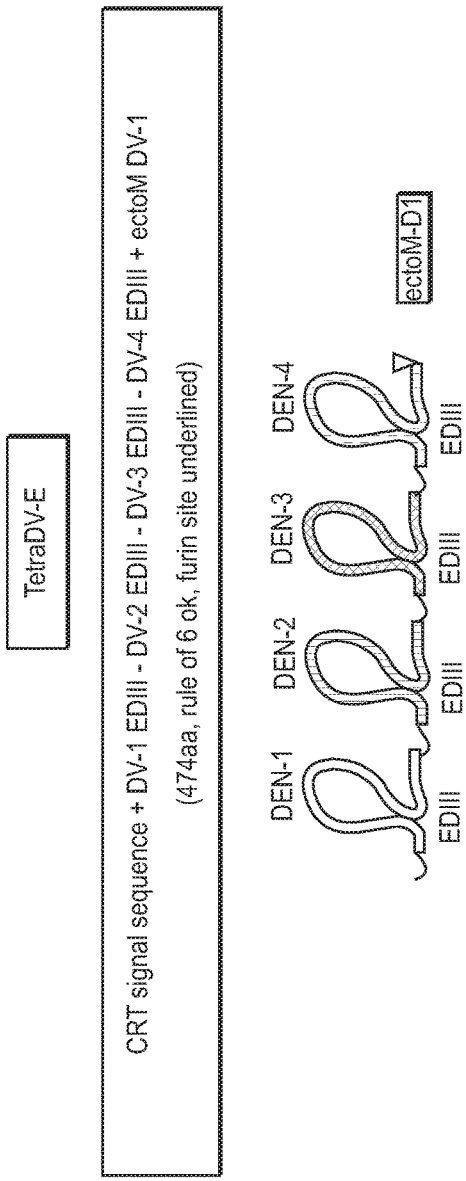

The insert contained in the plasmid vector is shown in FIG. 29.

The strain containing the vector may be cultivated in 100 μ/ml LB ampicillin medium.

3. Cloning and/or Expression Vectors and Antibodies

In a further aspect, the invention concerns any cloning and/or expression vector and any cell host (prokaryotic or eukaryotic) transformed by such a vector, and comprising regulation elements allowing the expression of the nucleotide sequence coding for a chimeric polypeptide of the invention. Such vectors are prepared using methods which are routinely used by the skilled person, and the resulting clones may be introduced into an appropriate host using standard methods such as, for example, lipofection, electroporation, thermal shock, transformation after chemical permeabilization of the membrane, or cell fusion.

The invention also encompasses host cells, in particular eukaryotic and prokaryotic cells, transformed by the vectors of the invention as well as transgenic animals, preferably mammals, with the exception of man, comprising one of said transformed cells of the invention. These animals may be used as models, to study the etiology of inflammatory and/or immune diseases, and in particular inflammatory diseases of the digestive tract, or in the study of cancers.

Of the cells which may be used in the present invention, the following may be cited: bacterial cells (Olins and Lee (1993), Curr Op Biotechnology 4: 520), but also yeast cells (Buckholz (1993), Curr Op Biotechnology 4, 538), as well as animal cells, in particular mammalian cell cultures (Edwards and Aruffo (1993), Curr Op Biotechnology 4, 558).

In the context of the present invention, the term "cloning and/or expression vector" refers to a polynucleotide construct designed to be transfected into different cell types. For this reason, these vectors encompass expression vectors designed for the expression of a nucleotide sequence in a host cell; cloning vectors designed for the isolation, propagation and replication of inserted nucleotides or shuttle vectors which comprise the attributes of more than one vector.

4. Polyclonal or Monoclonal Antibodies

The polypeptides and polynucleotides of the present invention may also be used to prepared polyclonal or monoclonal antibodies capable of binding (preferably in a specific manner) to at least one chimeric polypeptide/polynucleotide of the invention. The present invention thus also relates to such purified antibodies which may be obtained by very well known techniques such as, for example, the technique described by Kolher and Milstein (continuous cultures of fused cells secreting antibody of predefined specificity, Nature (1975), 262: 495-497). In a preferred embodiment of the invention, the antibodies are of the "humanized" type. A person skilled in the art would be able to use his general knowledge to prepare these types of antibodies.

5. Methods and Use

In a further aspect, the invention concerns the prevention and/or treatment of a Flaviviridae infection in a sensitive species. More particularly, the invention relates to the use of a recombinant viral vector of the invention for the preparation of an immunogenic composition intended for the prevention or treatment of a Flaviviridae infection in a sensitive species. The term "sensitive species" means any animal which is susceptible to a Flaviviridae infection, for example a human being.

The invention also relates to a method for preventing and/or treating a Flaviviridae infection in a sensitive species, comprising administering a pharmaceutically effective amount of at least one of the following elements:
a chimeric polypeptide of the invention;
a polynucleotide of the invention;
a recombinant viral vector of the invention;

an antibody of the invention; and a cloning and/or expression vector of the invention.

The term "Flaviviridae infection" means, for example, flaviviroses such as dengue, yellow fever, Japanese encephalitis and West Nile fever. The means for preparing and administering the elements of the present invention will not be described in more detail as they are already known to the skilled person 6. Compositions The present invention also concerns immunogenic compositions useful in the prevention and/or treatment of a Flaviviridae infection. The term "immunogenic composition" means a composition which contains elements having the capacity to induce, in vivo or in vitro, a cellular and/or humoral type immune response.

In a preferred embodiment, the composition of the present invention further contains a pharmaceutically acceptable vehicle and an element selected from the group constituted by:

a polynucleotide of the invention;

a chimeric polypeptide of the invention;

a recombinant viral vector of the invention;

an antibody of the invention; and a cloning and/or expression vector of the invention.

The compositions of the present invention may be in any solid or liquid form which is normal for pharmaceutical administration, examples of forms of administration being a liquid, a gel, or any other support which can allow controlled release, for example. Examples of compositions which may be used which may be cited are compositions which can be injected into human beings.

The compositions of the invention may also comprise components which increase or are capable of increasing the immunogenicity of the chimeric polypeptides of the invention, in particular other immunogenic peptides, specific or non-specific immunity adjuvants such as alun, QS21, Freund's adjuvant, $SBA_2$ adjuvant, montanide, polysaccharides or equivalent compounds.

A person versed in the art will be able to prepare pharmaceutically acceptable compositions and to determine, as a function of several factors, the preferred mode of administration and the amount which has to be administered. Factors which may influence the choice include: the nature of the treatment, the exact nature of the ingredients, active or non active, in the composition; the stage of the disease; the condition, age and weight of the patient, etc.

EXAMPLES

The following examples demonstrate other characteristics and advantages of the present invention and serve to illustrate rather than limit the scope of the present invention. Modifications and variations may be made without departing from the spirit and scope of the invention. Although other methods or products equivalent to those discussed below may be used to test or implement the present invention, preferred equipment and methods are described.

Example 1: The Recombined Measles Virus MVschw-$[EDIII+M^{1-40}]_{DV-1}$ as a Prototype for a Candidate Vaccine Against Dengue (PTR156)

Described in FIGS. 1 and 2, two immunogenic constructs based on the one hand on the capacity of domain III of the envelope E glycoprotein of the dengue virus to induce neutralizing antibodies and on the other hand on the involvement of the ectodomain of the membrane M protein ($M^{1-40}$) in viral pathogenicity (apoptosis) were inserted into the genome of the attenuated measles virus (Schwarz strain) (MVSchw). The viral sequences were under the dependency of the signal peptide of calreticulin to allow them to be targeted into the secretion pathway. The expression of the $[EDIII]_{DV-1}$ and $[EDIII+M^{1-40}]_{DV-1}$ sequences by the recombined viruses MVSchw was verified in infected Vero cells by indirect immunofluorescence using a polyclonal HMAF mouse serum directed against DV-1 (FIG. 3). Secretion of the EDIII and EDIII antigenic domains fused to the $M^{1-40}$ sequence (with the intercalating pentapeptide RRDKR) of the dengue virus, type-1 (DV-1) of the FGA/89 strain (Holmes E C et al, Mol Biol Evol 16(3): 405-409, 1999 and Despres P et al, Virology 196: 209-219) was observed by Western blot analysis in the supernatants of cells infected with the MVSchw$[EDIII]_{DV-1}$ and $MV_{schw}$-$[EDIII+M^{1-40}]_{DV-1}$ virus respectively (FIG. 4). Similarly, the production and secretion in the culture supernatants of a S2/$[EDIII+M^{1-40}]_{DV-1}$ drosophila cell line induced for expression of these proteins has been demonstrated (FIG. 5).

Two groups of four adult CD46/FNAR mice were immunized with $10^4$ TCID50 of each of the recombined MVSchw viruses (Tables 1 and 2). The empty MVSchw virus was used as a negative control. We determined the production of antibodies directed against the MVSchw virus (MV Ag) and the DV-1 virus (DV-1 Ag) including those which were specific to EDIII (Thullier P et al, 2001, J Gen Virol 82: 1885-1892) and neutralizing (Anti-DV-1 FRNT75) in immunized mice (Tables 1 and 2). We observed that the MVSchw$[EDIII]_{DV-1}$ virus is less effective at producing specific antibodies to DV-1 or EDIII alone after two inoculations spaced by one month (Table 1). Using the same immunization protocol, we observed that the MVSchw-$[EDIII+M^{1-}40]_{DV-1}$ virus induced significant titers of antibodies directed against DV-1 and against EDIII alone (Table 2). Anti-DV-1 antibodies including those which were neutralizing were still detected four months after the end of immunization.

When mice immunized more than 6 months previously with MVSchw-$[EDIII+M^{1-}40]_{DV-1}$ were given a booster with a single dose of 5 μg of total proteins of a concentrate of supernatant of S2/$[EDIII+M^{1-40}]_{DV-1}$ drosophila cells induced for expression of the fusion protein $[EDIII+M^{1-40}]_{DV-1}$ and in the presence of Alugel as an adjuvant, large amounts of anti-DV-1, anti-EDIII and neutralizing DV-1 antibodies were observed, which means that there was a well established humoral memory response in the vaccinated animals (Table 2). The anti-DV-1 antibodies were still present several months after the antigenic booster (Table 2).

Three months after the antigenic booster with r$[EDIII+M^{1-40}]_{DV-1}$, mice immunized with MVSchw-$[EDIII+M^{1-}40]_{DV-1}$ were inoculated intraperitoneally with $10^7$ FFU of FGA/NA did strain DV-1 (DV-1 is responsible for an asymptomatic infection in the IFNAR mouse). Large titers of anti-DV-1 antibody (in particular directed against EDIII) including those which neutralized DV-1 Hawaii strain (neutralizing titer # 4000) were observed after 3 weeks of viral challenge (Table 2). It should be noted that mice immunized 9 months previously with $MV_{schw}[EDIII+M^{1-}40]_{DV-1}$ (this construct not inducing anti-EDIII antibody or neutralizing DV-1 antibody) then challenged intraperitoneally with $10^7$ FFU of FGA/NA did strain DV-1 produced andi DV-1 produced anti-DV-1, anti-EDIII and neutralizing titers of 20000, 5000, and 80 respectively; these were values equivalent to those observed in BALB/c mice or IFNAR mice challenged under the same experimental conditions.

In conclusion, the fusion sequence [EDIII+M$^{1-40}$]$_{DV-1}$ secreted by the MV$_{Schw}$[EDIII+M$^{1-40}$]$_{DV-1}$ virus is capable of generating neutralizing anti-DV-1 antibodies and of inducing a long term humoral memory response which is effectively stimulated on the one hand by the soluble antigen r[EDIII+M$^{1-40}$]$_{DV-1}$ and on the other hand in response to a viral infection. In contrast, the only antigenic EDIII domain secreted by the MV$_{schw}$[EDIII+M$^{1-40}$]$_{DV-1}$ virus is of low immunogenicity in CD46$^+$-FINAR mice. Our complementary work demonstrates that the pro-apoptotic ApoptoM (M$^{32-40}$) peptide at the C-terminal end of M determines the immunogenic power of the [EDIII+$^{M-}$40]$_{DV1}$ fusion sequence since the MV$_{Schw-}$[EDIII+M$^{1-30}$]$_{DV-1}$ virus without ApoptoM induces a production of anti-DV-1 antibody equivalent to that obtained after immunization with the MV$_{Schw-}$[EDIII]$_{DV-1}$ virus.

As a general methodology for pediatric vaccination against dengue, we propose to immunize young individuals with the [EDIII+M$^{1-40}$]$_{DV-1}$ virus using a double inoculation spaced by one month, then to restimulate them later with the r[EDIII+M$^{1-40}$]$_{DV-1}$ antigen as a vaccine booster or prophylactically against the risk of an infection by the dengue virus. This immunization strategy is being validated for the four serotypes of dengue based on an antigen composed of a tetramer of the four EDIII domains of DV-1, -2, -3 and -4 fused to the cytotoxic ApoptoM sequence.

Our first experimental results underline the importance of a reduced size immunogen derived from the envelope protein of the DV-1 virus in combination with the immunostimulating capacity of the live measles vector, a strategy which allows the induction of a neutralizing humoral response which is effective against the dengue virus. They define a proof of concept for the design of the tetrameric constructs of the antigenic domains of DV which will allow simultaneous and long term immunization against the four dengue serotypes.

Example 2: Construction of Chimeric Polypeptides Optimized for Expression in Mammals In the present example, the inventors have developed novel antigenic constructs useful against a Flaviviridae infection.

These novel chimeric polypeptides are based on an antigen composed of a tetramer of the four EDIII domains of the four serotypes of the dengue virus, fused together and to one or the other of the cytotoxic apoptoM sequences shown in FIG. 30.

Thereafter, these chimeric polypeptides optimized for expression in a mammal were inserted into the genome of the attenuated measles virus, Schwarz strain, (MVSchw) viral strain. FIGS. 15 to 29 show the amino acid sequences of five preferred chimeric polypeptides and the polynucleotides encoding them.

These chimeric polypeptides were constructed using the following optimization conditions:

Optimization information for these sequences:

(Cai No=0.806, mean % GC=53.46, GC distribution: homogeneous about 50%);

elimination of internal "TATA box" sequences, a portion rich in AT or GC, elements with sequences ARE, INS and CRS, repeat sequences, sequences with secondary RNA structure, cryptic splicing sequences;

elimination of the following restriction sites: NheI, BamHI, XhoI, EcoRI, KpnI, SalI, BspEI, BglII, NotI, BssHII, BsiWI, with the exception of BsiWI in the first position and BssHII in the last position;

Elimination of TTTT, TTTAA, AAAGGG, AAAAGG, GGGAAA, GGGGAA motifs and their complements TTCCCC, TTTCCC, CCTTTT, CCCTTT.

TABLE 1

Antibody response directed against the MVSchw virus in CD46$^+$/IFNAR mice inoculated i.p. with MV$_{Schw-}$[EDIII]$_{DV-1}$

| Immunization (month) | MV Ag titer[c] | DV-1 Ag titer[d] | DV-1 rEDIII titer[e] | Anti-DV-1 FRNT75[f] |
|---|---|---|---|---|
| 1[a] | 15000 | <100 | <100 | ND |
| 2[b] | 40000 | 100 | 10 | <10 |

[a]10$^4$ TCIP50 of MV-DV-1 [EDIII + M$^{1-40}$]$_{DV1}$ was given i.p. to four adult mice;
[b]The individuals received a booster injection with 10$^4$ TCIP$_{50}$ of MV-DV-1 [EDIII + M$^{1-40}$]$_{DV-1}$;
[c]Determined by ELISA (Trinity Biotech) on pooled serums inactivated by heating;
[d]Determined by ELISA on pooled serums inactivated by heating. Microtitration plates were coated with 5 × 10$^5$ FFU of purified sucrose, FGA/NA d1d as viral antigen;
[e]Determined by ELISA on pooled serums inactivated by heating. Microtitration plates were coated with 50 ng of highly purified recombinant DV-1 EDIII as viral antigen;
[f]Anti-DV-1 neutralization antibodies were detected using a focus reduction neutralization test (FRNT). Pooled serums inactivated by heating were incubated with the DV-1 Hawaii line and titrating the virus on Vero cells using the plaque immunoassay test. FRNT75, the highest serum dilution tested, reduced the number of FFU by at least 75%.

TABLE 2

Antibody response directed against the MVSchw virus in CD46$^+$/IFNAR mice inoculated i.p. with MV$_{Schw-}$[EDIII + M$^{1-40}$]$_{DV-1}$

| Immunization (months) | MV Ag titer[e] | DV-1 Ag titer[f] | DV-1 rEDIII titer[g] | Anti-DV-1 FRNT75[h] |
|---|---|---|---|---|
| 1[a] | 15000 | <100 | </=100 | ND |
| 2[b] | 40000 | 1600 | 400 | 10 |
| 3 | 30000 | 1000 | 600 | 10 |
| 6 | 20000 | 500 | 100 | 40 |
| 7[c] | 20000 | 20000 | 100000 | 800 |
| 9 | 10000 | 2000 | 10000 | 100 |
| 10[d] | 10000 | 200000 | 800000 | 4000 |

[a]10$^4$ TCIP$_{50}$ of MV-DV-1 [EDIII + M$^{1-40}$]$_{DV-1}$ was given i.p. to four adult mice;
[b]The individuals received a booster injection with 10$^4$ TCIP$_{50}$ of MV-DV-1 [EDIII + M$^{1-40}$]$_{DV-1}$;
[c]The immunized mice received a booster injection of 5 μg of total secreted proteins deriving from a supernatant of S2 cells expressing rDV1[EDIII + M$^{1-40}$]$_{DV-1}$ in the presence of Alugel adjuvant;
[d]The immunized mice were inoculated i.p. with 10$^7$ FFU of FGA/NA d1d from the DV-1 line for three weeks;
[e]Determined by ELISA (Trinity Biotech) on pooled serums inactivated by heating;
[f]Determined by ELISA on pooled serums inactivated by heating. Microtitration plates were coated with 5 × 10$^5$ FFU of purified sucrose, FGA/NA d1d as viral antigen;
[g]Determined by ELISA on pooled serums inactivated by heating. Microtitration plates were coated with 50 ng of highly purified recombinant DV-1 EDIII as viral antigen;
[h]Anti-DV-1 neutralization antibodies were detected using FRNT. Pooled serums inactivated by heating were incubated with the DV-1 Hawaii line and titrating the virus on Vero cells using the plaque immunoassay test. FRNT75, the highest serum dilution tested, reduced the number of FFU by at least 75%.

The invention claimed is:

1. A chimeric polypeptide comprising a subdomain of the E protein of a Flavivirus bound to a peptide of a subdomain of the membrane M protein of a Flavivirus;
    wherein the subdomain of the E protein comprises a dengue virus ectodomain III dimer, in which each dengue virus ectodomain III in the dimer is independently selected from the ectodomain III of dengue virus serotype 1, the ectodomain III of dengue virus serotype 2, the ectodomain III of dengue virus serotype 3, and the ectodomain III of dengue virus serotype 4; and
    wherein the subdomain of the E protein further comprises at least one amino acid sequence selected from the group consisting of: amino acids 21 to 262 of SEQ ID NO: 8 and amino acids 21 to 262 of SEQ ID NO: 10.

2. The chimeric polypeptide of claim 1, wherein the subdomain of the M protein comprises amino acids 1-40 of the M protein.

3. The chimeric polypeptide of claim 1, wherein the subdomain of the M protein comprises an apoptoM sequence.

4. The chimeric polypeptide of claim 1, wherein the chimeric polypeptide further comprises a binding segment binding the subdomain of the E protein to the peptide of the subdomain of the M protein.

5. The chimeric polypeptide of claim 4, wherein the binding segment is a pentapeptide having the amino acid sequence RRDKR (SEQ ID NO: 33) or RREKR (SEQ ID NO: 34).

6. An immunogenic composition comprising the chimeric polypeptide of claim 1 and a pharmaceutically acceptable vehicle.

7. A method for inducing an immune response against a Flavivirus in a sensitive species, comprising: administering a pharmaceutically effective amount of an immunogenic composition according to claim 6 to the sensitive species.

8. The method according to claim 7, wherein the immunogenic composition is administered in the presence of an adjuvant.

9. The method according to claim 7, further comprising administering a booster immunization of the immunogenic composition.

10. The method according to claim 8, further comprising administering a booster immunization of the immunogenic composition.

11. The method according to claim 7, wherein the Flavivirus is selected from a dengue virus, a yellow fever virus, a Japanese encephalitis virus and a West Nile fever virus.

12. The method according to claim 8, wherein the Flavivirus is selected from a dengue virus, a yellow fever virus, a Japanese encephalitis virus and a West Nile fever virus.

* * * * *